US010206709B2

(12) United States Patent
Griffith et al.

(10) Patent No.: US 10,206,709 B2
(45) Date of Patent: Feb. 19, 2019

(54) APPARATUS FOR INTRODUCING AN OBJECT INTO A PATIENT

(71) Applicant: Ethicon Endo-Surgery, Inc., Cincinnati, OH (US)

(72) Inventors: David B. Griffith, Cincinnati, OH (US); Sean P. Conlon, Loveland, OH (US); William B. Weisenburgh, II, Maineville, OH (US); Christopher J. Hess, Blue Ash, OH (US); Kempton K. Carroll, II, San Clemente, CA (US)

(73) Assignee: Ethicon LLC, Guaynabo, PR (US)

( * ) Notice: Subject to any disclaimer, the term of this patent is extended or adjusted under 35 U.S.C. 154(b) by 200 days.

(21) Appl. No.: 15/226,588

(22) Filed: Aug. 2, 2016

(65) Prior Publication Data

US 2016/0338731 A1 Nov. 24, 2016

Related U.S. Application Data

(62) Division of application No. 13/470,781, filed on May 14, 2012, now Pat. No. 9,427,255.

(51) Int. Cl.
*A61B 17/34* (2006.01)
*A61B 1/00* (2006.01)
(Continued)

(52) U.S. Cl.
CPC ...... *A61B 17/3423* (2013.01); *A61B 1/00154* (2013.01); *A61B 1/00158* (2013.01);
(Continued)

(58) Field of Classification Search
CPC ........ A61B 2017/3445; A61B 17/3423; A61B 1/00154; A61B 1/00158; A61B 1/041;
(Continued)

(56) References Cited

U.S. PATENT DOCUMENTS

| 112,794 A | 3/1871 | Felton |
|---|---|---|
| 645,576 A | 3/1900 | Tesla |

(Continued)

FOREIGN PATENT DOCUMENTS

| AU | 666310 B2 | 2/1996 |
|---|---|---|
| DE | 3008120 A1 | 9/1980 |

(Continued)

OTHER PUBLICATIONS

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

(Continued)

*Primary Examiner* — Manuel A Mendez

(57) ABSTRACT

A cannula assembly including a housing, a rotatable member, a first plurality of membranes, and a second plurality of membranes is disclosed. The housing may include a distal end defining a distal opening, wherein the distal end is configured to couple to a cannula tube aligned with the distal opening, and a proximal end defining a proximal opening. The rotatable member may be positioned within the housing and may define a passage in fluid communication with the distal opening, a first opening in fluid communication with the passage, and a second opening in fluid communication with the passage. The first plurality of membranes may be arranged as a stack at the first opening, wherein each of the first plurality of membranes defines an aperture. The second plurality of membranes may be arranged as a stack at the second opening, wherein each of the second plurality of membranes defines an aperture. The rotatable member may be configured to rotate within the housing between a first position and a second position, wherein in the first position, the first opening aligns with the distal opening of the (Continued)

housing, and wherein in the second position, the second opening aligns with the distal opening of the housing.

20 Claims, 33 Drawing Sheets

(51) Int. Cl.
*A61B 1/04* (2006.01)
*A61B 1/313* (2006.01)
*A61B 17/00* (2006.01)

(52) U.S. Cl.
CPC ............ *A61B 1/041* (2013.01); *A61B 1/3132* (2013.01); *A61B 17/3421* (2013.01); *A61B 17/3462* (2013.01); *A61B 17/3474* (2013.01); *A61B 2017/00283* (2013.01); *A61B 2017/3445* (2013.01)

(58) Field of Classification Search
CPC .............. A61B 1/3132; A61B 17/3421; A61B 17/3462; A61B 17/3474; A61B 2017/00283
USPC .................. 600/114, 118, 153–159, 138; 604/167.01–167.06
See application file for complete search history.

(56) References Cited

U.S. PATENT DOCUMENTS

| | | |
|---|---|---|
| 649,621 A | 5/1900 | Tesla |
| 787,412 A | 4/1905 | Tesla |
| 1,039,354 A | 9/1912 | Bonadio |
| 1,127,948 A | 2/1915 | Wappler |
| 1,482,653 A | 2/1924 | Lilly |
| 1,581,706 A | 4/1926 | White |
| 1,581,707 A | 4/1926 | White |
| 1,581,708 A | 4/1926 | White |
| 1,581,709 A | 4/1926 | White |
| 1,581,710 A | 4/1926 | White |
| 1,625,602 A | 4/1927 | Gould |
| 1,916,722 A | 7/1933 | Ende |
| 2,028,635 A | 1/1936 | Wappler |
| 2,031,682 A | 2/1936 | Wappler |
| 2,113,246 A | 4/1938 | Wappler |
| 2,137,710 A | 11/1938 | Anderson |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,451,077 A | 10/1948 | Emsig |
| 2,493,108 A | 1/1950 | Casey |
| 2,504,152 A | 4/1950 | Riker |
| 2,938,382 A | 5/1960 | De Graaf |
| 2,952,206 A | 9/1960 | Becksted |
| 3,044,461 A | 7/1962 | Murdock |
| 3,069,195 A | 12/1962 | Buck |
| 3,070,088 A | 12/1962 | Brahos |
| 3,110,956 A | 11/1963 | Fischer, Jr. |
| 3,170,471 A | 2/1965 | Schnitzer |
| 3,435,824 A | 4/1969 | Gamponia |
| 3,470,876 A | 10/1969 | Barchilon |
| 3,481,325 A | 12/1969 | Glassman |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,854,743 A | 12/1974 | Hansen |
| 3,929,123 A | 12/1975 | Jamshidi |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,043,342 A | 8/1977 | Morrison, Jr. |
| 4,071,028 A | 1/1978 | Perkins |
| 4,085,743 A | 4/1978 | Yoon |
| 4,164,225 A | 8/1979 | Johnson et al. |
| 4,170,997 A | 10/1979 | Pinnow et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,281,646 A | 8/1981 | Kinoshita |
| 4,285,344 A | 8/1981 | Marshall |
| 4,311,143 A | 1/1982 | Komiya |
| 4,329,980 A | 5/1982 | Terada |
| 4,393,872 A | 7/1983 | Reznik et al. |
| 4,396,021 A | 8/1983 | Baumgartner |
| 4,396,139 A | 8/1983 | Hall et al. |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,492,232 A | 1/1985 | Green |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,649,904 A | 3/1987 | Krauter et al. |
| 4,653,476 A | 3/1987 | Bonnet |
| 4,655,219 A | 4/1987 | Petruzzi |
| 4,657,016 A | 4/1987 | Garito et al. |
| 4,657,018 A | 4/1987 | Hakky |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,239 A | 12/1987 | Sorochenko et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,742,817 A | 5/1988 | Kawashima et al. |
| 4,753,223 A | 6/1988 | Bremer |
| 4,763,669 A | 8/1988 | Jaeger |
| 4,770,188 A | 9/1988 | Chikama |
| 4,790,624 A | 12/1988 | Van Hoye et al. |
| 4,791,707 A | 12/1988 | Tucker |
| 4,796,627 A | 1/1989 | Tucker |
| 4,807,593 A | 2/1989 | Ito |
| 4,815,450 A | 3/1989 | Patel |
| 4,819,620 A | 4/1989 | Okutsu |
| 4,823,794 A | 4/1989 | Pierce |
| 4,829,999 A | 5/1989 | Auth |
| 4,836,188 A | 6/1989 | Berry |
| 4,846,573 A | 7/1989 | Taylor et al. |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,904,048 A | 2/1990 | Sogawa et al. |
| 4,911,148 A | 3/1990 | Sosnowski et al. |
| 4,926,860 A | 5/1990 | Stice et al. |
| 4,934,364 A | 6/1990 | Green |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |

(56) References Cited

U.S. PATENT DOCUMENTS

| | | | |
|---|---|---|---|
| 4,979,496 | A | 12/1990 | Komi |
| 4,979,950 | A | 12/1990 | Transue et al. |
| 4,984,581 | A | 1/1991 | Stice |
| 4,990,152 | A | 2/1991 | Yoon |
| 4,991,565 | A | 2/1991 | Takahashi et al. |
| 4,994,079 | A | 2/1991 | Genese et al. |
| 5,007,917 | A | 4/1991 | Evans |
| 5,010,876 | A | 4/1991 | Henley et al. |
| 5,015,249 | A | 5/1991 | Nakao et al. |
| 5,020,514 | A | 6/1991 | Heckele |
| 5,020,535 | A | 6/1991 | Parker et al. |
| 5,025,778 | A | 6/1991 | Silverstein et al. |
| 5,026,379 | A | 6/1991 | Yoon |
| 5,033,169 | A | 7/1991 | Bindon |
| 5,037,433 | A | 8/1991 | Wilk et al. |
| 5,041,129 | A | 8/1991 | Hayhurst et al. |
| 5,046,513 | A | 9/1991 | Gatturna et al. |
| 5,049,153 | A | 9/1991 | Nakao et al. |
| 5,050,585 | A | 9/1991 | Takahashi |
| 5,052,372 | A | 10/1991 | Shapiro |
| 5,065,516 | A | 11/1991 | Dulebohn |
| 5,066,295 | A | 11/1991 | Kozak et al. |
| 5,098,378 | A | 3/1992 | Piontek et al. |
| 5,099,827 | A | 3/1992 | Melzer et al. |
| 5,108,421 | A | 4/1992 | Fowler |
| 5,123,913 | A | 6/1992 | Wilk et al. |
| 5,123,914 | A | 6/1992 | Cope |
| 5,133,727 | A | 7/1992 | Bales et al. |
| 5,147,374 | A | 9/1992 | Fernandez |
| 5,156,609 | A | 10/1992 | Nakao et al. |
| 5,174,300 | A | 12/1992 | Bales et al. |
| 5,176,126 | A | 1/1993 | Chikama |
| 5,190,050 | A | 3/1993 | Nitzsche |
| 5,190,555 | A | 3/1993 | Wetter et al. |
| 5,192,284 | A | 3/1993 | Pleatman |
| 5,192,300 | A | 3/1993 | Fowler |
| 5,197,963 | A | 3/1993 | Parins |
| 5,201,752 | A | 4/1993 | Brown et al. |
| 5,201,908 | A | 4/1993 | Jones |
| 5,203,785 | A | 4/1993 | Slater |
| 5,203,787 | A | 4/1993 | Noblitt et al. |
| 5,209,747 | A | 5/1993 | Knoepfler |
| 5,217,003 | A | 6/1993 | Wilk |
| 5,217,453 | A | 6/1993 | Wilk |
| 5,219,357 | A | 6/1993 | Honkanen et al. |
| 5,219,358 | A | 6/1993 | Bendel et al. |
| 5,222,362 | A | 6/1993 | Maus et al. |
| 5,222,961 | A | 6/1993 | Nakao et al. |
| 5,222,965 | A | 6/1993 | Haughton |
| 5,234,437 | A | 8/1993 | Sepetka |
| 5,234,453 | A | 8/1993 | Smith et al. |
| 5,235,964 | A | 8/1993 | Abenaim |
| 5,242,456 | A | 9/1993 | Nash et al. |
| 5,245,460 | A | 9/1993 | Allen et al. |
| 5,246,424 | A | 9/1993 | Wilk |
| 5,257,999 | A | 11/1993 | Slanetz, Jr. |
| 5,259,366 | A | 11/1993 | Reydel et al. |
| 5,263,958 | A | 11/1993 | deGuillebon et al. |
| 5,273,524 | A | 12/1993 | Fox et al. |
| 5,275,607 | A | 1/1994 | Lo et al. |
| 5,275,614 | A | 1/1994 | Haber et al. |
| 5,275,616 | A | 1/1994 | Fowler |
| 5,284,128 | A | 2/1994 | Hart |
| 5,284,162 | A | 2/1994 | Wilk |
| 5,287,845 | A | 2/1994 | Faul et al. |
| 5,287,852 | A | 2/1994 | Arkinstall |
| 5,290,299 | A | 3/1994 | Fain et al. |
| 5,290,302 | A | 3/1994 | Pericic |
| 5,295,977 | A | 3/1994 | Cohen et al. |
| 5,297,536 | A | 3/1994 | Wilk |
| 5,297,687 | A | 3/1994 | Freed |
| 5,301,061 | A | 4/1994 | Nakada et al. |
| 5,312,023 | A | 5/1994 | Green et al. |
| 5,312,333 | A | 5/1994 | Churinetz et al. |
| 5,312,351 | A | 5/1994 | Gerrone |
| 5,312,416 | A | 5/1994 | Spaeth et al. |
| 5,312,423 | A | 5/1994 | Rosenbluth et al. |
| 5,318,589 | A | 6/1994 | Lichtman |
| 5,320,636 | A | 6/1994 | Slater |
| 5,324,261 | A | 6/1994 | Amundson et al. |
| 5,325,845 | A | 7/1994 | Adair |
| 5,330,471 | A | 7/1994 | Eggers |
| 5,330,486 | A | 7/1994 | Wilk |
| 5,330,488 | A | 7/1994 | Goldrath |
| 5,330,496 | A | 7/1994 | Alferness |
| 5,330,502 | A | 7/1994 | Hassler et al. |
| 5,331,971 | A | 7/1994 | Bales et al. |
| 5,334,168 | A | 8/1994 | Hemmer |
| 5,334,198 | A | 8/1994 | Hart et al. |
| 5,336,192 | A | 8/1994 | Palestrant |
| 5,336,222 | A | 8/1994 | Durgin, Jr. et al. |
| 5,339,805 | A | 8/1994 | Parker |
| 5,341,815 | A | 8/1994 | Cofone et al. |
| 5,342,396 | A | 8/1994 | Cook |
| 5,344,428 | A | 9/1994 | Griffiths |
| 5,345,927 | A | 9/1994 | Bonutti |
| 5,348,259 | A | 9/1994 | Blanco et al. |
| 5,350,391 | A | 9/1994 | Iacovelli |
| 5,352,184 | A | 10/1994 | Goldberg et al. |
| 5,352,222 | A | 10/1994 | Rydell |
| 5,354,302 | A | 10/1994 | Ko |
| 5,354,311 | A | 10/1994 | Kambin et al. |
| 5,356,381 | A | 10/1994 | Ensminger et al. |
| 5,356,408 | A | 10/1994 | Rydell |
| 5,360,428 | A | 11/1994 | Hutchinson, Jr. |
| 5,364,408 | A | 11/1994 | Gordon |
| 5,364,410 | A | 11/1994 | Failla et al. |
| 5,366,466 | A | 11/1994 | Christian et al. |
| 5,366,467 | A | 11/1994 | Lynch et al. |
| 5,368,605 | A | 11/1994 | Miller, Jr. |
| 5,368,606 | A | 11/1994 | Marlow et al. |
| 5,370,647 | A | 12/1994 | Graber et al. |
| 5,370,679 | A | 12/1994 | Atlee, III |
| 5,374,273 | A | 12/1994 | Nakao et al. |
| 5,374,275 | A | 12/1994 | Bradley et al. |
| 5,374,277 | A | 12/1994 | Hassler |
| 5,374,953 | A | 12/1994 | Sasaki et al. |
| 5,376,077 | A * | 12/1994 | Gomringer .... A61B 17/320758 604/167.06 |
| 5,377,695 | A | 1/1995 | An Haack |
| 5,378,234 | A | 1/1995 | Hammerslag et al. |
| 5,383,877 | A | 1/1995 | Clarke |
| 5,383,888 | A | 1/1995 | Zvenyatsky et al. |
| 5,386,817 | A | 2/1995 | Jones |
| 5,387,259 | A | 2/1995 | Davidson |
| 5,391,174 | A | 2/1995 | Weston |
| 5,392,789 | A | 2/1995 | Slater et al. |
| 5,395,367 | A | 3/1995 | Wilk |
| 5,395,381 | A | 3/1995 | Green et al. |
| 5,395,386 | A | 3/1995 | Slater |
| 5,397,332 | A | 3/1995 | Kammerer et al. |
| 5,401,248 | A | 3/1995 | Bencini |
| 5,403,311 | A | 4/1995 | Abele et al. |
| 5,403,326 | A | 4/1995 | Harrison et al. |
| 5,403,328 | A | 4/1995 | Shallman |
| 5,403,342 | A | 4/1995 | Tovey et al. |
| 5,403,348 | A | 4/1995 | Bonutti |
| 5,405,073 | A | 4/1995 | Porter |
| 5,405,359 | A | 4/1995 | Pierce |
| 5,409,478 | A | 4/1995 | Gerry et al. |
| 5,417,699 | A | 5/1995 | Klein et al. |
| 5,423,821 | A | 6/1995 | Pasque |
| 5,431,635 | A | 7/1995 | Yoon |
| 5,433,721 | A | 7/1995 | Hooven et al. |
| 5,433,735 | A | 7/1995 | Zanakis et al. |
| 5,439,471 | A | 8/1995 | Kerr |
| 5,439,478 | A | 8/1995 | Palmer |
| 5,441,059 | A | 8/1995 | Dannan |
| 5,441,494 | A | 8/1995 | Ortiz |
| 5,441,498 | A | 8/1995 | Perkins |
| 5,441,499 | A | 8/1995 | Fritzsch |
| 5,443,463 | A | 8/1995 | Stern et al. |
| 5,445,638 | A | 8/1995 | Rydell et al. |
| 5,445,648 | A | 8/1995 | Cook |

(56) References Cited

U.S. PATENT DOCUMENTS

| | | |
|---|---|---|
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,472,441 A | 12/1995 | Edwards et al. |
| 5,478,347 A | 12/1995 | Aranyi |
| 5,478,352 A | 12/1995 | Fowler |
| 5,480,404 A | 1/1996 | Kammerer et al. |
| 5,482,029 A | 1/1996 | Sekiguchi et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schulken et al. |
| 5,499,992 A | 3/1996 | Meade et al. |
| 5,499,997 A | 3/1996 | Sharpe et al. |
| 5,500,012 A | 3/1996 | Brucker et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |
| 5,536,234 A | 7/1996 | Newman |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,590,660 A | 1/1997 | MacAulay et al. |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,574 A | 2/1997 | Stefanchik et al. |
| 5,601,588 A | 2/1997 | Tonomura et al. |
| 5,601,602 A | 2/1997 | Fowler |
| 5,604,531 A | 2/1997 | Iddan et al. |
| 5,607,386 A | 3/1997 | Flam |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,613,977 A | 3/1997 | Weber et al. |
| 5,614,943 A | 3/1997 | Nakamura et al. |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,519 A | 7/1997 | Lee et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,276 A | 10/1997 | Lundquist |
| 5,681,279 A | 10/1997 | Roper et al. |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,725,542 A | 3/1998 | Yoon |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,759,150 A | 6/1998 | Konou et al. |
| 5,759,151 A | 6/1998 | Sturges |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,776,188 A | 7/1998 | Shepherd et al. |
| 5,779,701 A | 7/1998 | McBrayer et al. |
| 5,779,716 A | 7/1998 | Cano et al. |
| 5,779,720 A | 7/1998 | Walder-Utz et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |

(56) References Cited

U.S. PATENT DOCUMENTS

| | | |
|---|---|---|
| 5,797,939 A | 8/1998 | Yoon |
| 5,797,941 A | 8/1998 | Schulze et al. |
| 5,797,959 A | 8/1998 | Castro et al. |
| 5,797,960 A | 8/1998 | Stevens et al. |
| 5,800,449 A | 9/1998 | Wales |
| 5,800,451 A | 9/1998 | Buess et al. |
| 5,803,903 A | 9/1998 | Athas et al. |
| 5,807,395 A | 9/1998 | Mulier et al. |
| 5,808,665 A | 9/1998 | Green |
| 5,810,805 A | 9/1998 | Sutcu et al. |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,026 A | 9/1998 | Yoon |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,818,527 A | 10/1998 | Yamaguchi et al. |
| 5,819,736 A | 10/1998 | Avny et al. |
| 5,823,947 A | 10/1998 | Yoon et al. |
| 5,824,071 A | 10/1998 | Nelson et al. |
| 5,827,190 A | 10/1998 | Palcic et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,221 A | 11/1998 | Stein et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,833,715 A | 11/1998 | Vachon et al. |
| 5,836,960 A | 11/1998 | Kolesa et al. |
| 5,843,017 A | 12/1998 | Yoon |
| 5,843,097 A | 12/1998 | Mayenberger et al. |
| 5,843,121 A | 12/1998 | Yoon |
| 5,849,022 A | 12/1998 | Sakashita et al. |
| 5,853,374 A | 12/1998 | Hart et al. |
| 5,855,569 A | 1/1999 | Komi |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,873,849 A | 2/1999 | Bernard |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,906,625 A | 5/1999 | Bito et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,919,207 A | 7/1999 | Taheri |
| 5,921,892 A | 7/1999 | Easton |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,938,661 A | 8/1999 | Hahnen |
| 5,941,815 A | 8/1999 | Chang |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,933 A | 11/1999 | Yoon |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,033,401 A | 3/2000 | Edwards et al. |
| 6,036,640 A | 3/2000 | Corace et al. |
| 6,036,685 A | 3/2000 | Mueller |
| 6,050,992 A | 4/2000 | Nichols |
| 6,053,927 A | 4/2000 | Hamas |
| 6,053,937 A | 4/2000 | Edwards et al. |
| 6,059,719 A | 5/2000 | Yamamoto et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | MacK |
| 6,086,600 A | 7/2000 | Kortenbach |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,123,718 A | 9/2000 | Tu et al. |
| 6,131,790 A | 10/2000 | Piraka |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |

(56) References Cited

U.S. PATENT DOCUMENTS

| | | | |
|---|---|---|---|
| 6,149,662 | A | 11/2000 | Pugliesi et al. |
| 6,152,871 | A | 11/2000 | Foley et al. |
| 6,152,920 | A | 11/2000 | Thompson et al. |
| 6,156,006 | A | 12/2000 | Brosens et al. |
| 6,159,200 | A | 12/2000 | Verdura et al. |
| 6,165,175 | A | 12/2000 | Wampler et al. |
| 6,165,184 | A | 12/2000 | Verdura et al. |
| 6,168,570 | B1 | 1/2001 | Ferrera |
| 6,168,605 | B1 | 1/2001 | Measamer et al. |
| 6,169,269 | B1 | 1/2001 | Maynard |
| 6,170,130 | B1 | 1/2001 | Hamilton et al. |
| 6,173,872 | B1 | 1/2001 | Cohen |
| 6,179,776 | B1 | 1/2001 | Adams et al. |
| 6,179,832 | B1 | 1/2001 | Jones et al. |
| 6,179,837 | B1 | 1/2001 | Hooven |
| 6,183,420 | B1 | 2/2001 | Douk et al. |
| 6,190,353 | B1 | 2/2001 | Makower et al. |
| 6,190,383 | B1 | 2/2001 | Schmaltz et al. |
| 6,190,384 | B1 | 2/2001 | Ouchi |
| 6,190,399 | B1 | 2/2001 | Palmer et al. |
| 6,203,533 | B1 | 3/2001 | Ouchi |
| 6,206,872 | B1 | 3/2001 | Lafond et al. |
| 6,206,877 | B1 | 3/2001 | Kese et al. |
| 6,206,904 | B1 | 3/2001 | Ouchi |
| 6,210,409 | B1 | 4/2001 | Ellman et al. |
| 6,214,007 | B1 | 4/2001 | Anderson |
| 6,214,028 | B1 | 4/2001 | Yoon et al. |
| 6,216,043 | B1 | 4/2001 | Swanson et al. |
| 6,228,096 | B1 | 5/2001 | Marchand |
| 6,231,506 | B1 | 5/2001 | Hu et al. |
| 6,234,958 | B1 | 5/2001 | Snoke et al. |
| 6,240,312 | B1 | 5/2001 | Alfano et al. |
| 6,245,079 | B1 | 6/2001 | Nobles et al. |
| 6,246,914 | B1 | 6/2001 | de la Rama et al. |
| 6,248,124 | B1 | 6/2001 | Pedros et al. |
| 6,258,064 | B1 | 7/2001 | Smith et al. |
| 6,261,242 | B1 | 7/2001 | Roberts et al. |
| 6,264,664 | B1 | 7/2001 | Avellanet |
| 6,270,497 | B1 | 8/2001 | Sekino et al. |
| 6,270,505 | B1 | 8/2001 | Yoshida et al. |
| 6,277,136 | B1 | 8/2001 | Bonutti |
| 6,283,963 | B1 | 9/2001 | Regula |
| 6,287,304 | B1 | 9/2001 | Eggers et al. |
| 6,293,909 | B1 | 9/2001 | Chu et al. |
| 6,293,952 | B1 | 9/2001 | Brosens et al. |
| 6,296,630 | B1 | 10/2001 | Altman et al. |
| 6,314,963 | B1 | 11/2001 | Vaska et al. |
| 6,322,578 | B1 | 11/2001 | Houle et al. |
| 6,325,534 | B1 | 12/2001 | Hawley et al. |
| 6,326,177 | B1 | 12/2001 | Schoenbach et al. |
| 6,328,730 | B1 | 12/2001 | Harkrider, Jr. |
| 6,350,267 | B1 | 2/2002 | Stefanchik |
| 6,350,269 | B1 | 2/2002 | Shipp et al. |
| 6,350,278 | B1 | 2/2002 | Lenker et al. |
| 6,352,503 | B1 | 3/2002 | Matsui et al. |
| 6,352,541 | B1 | 3/2002 | Kienzle et al. |
| 6,352,543 | B1 | 3/2002 | Cole |
| 6,355,013 | B1 | 3/2002 | van Muiden |
| 6,355,035 | B1 | 3/2002 | Manushakian |
| 6,361,534 | B1 | 3/2002 | Chen et al. |
| 6,364,879 | B1 | 4/2002 | Chen et al. |
| 6,368,340 | B2 | 4/2002 | Malecki et al. |
| 6,371,956 | B1 | 4/2002 | Wilson et al. |
| 6,379,366 | B1 | 4/2002 | Fleischman et al. |
| 6,383,195 | B1 | 5/2002 | Richard |
| 6,383,197 | B1 | 5/2002 | Conlon et al. |
| 6,387,671 | B1 | 5/2002 | Rubinsky et al. |
| 6,391,029 | B1 | 5/2002 | Hooven et al. |
| 6,398,708 | B1 | 6/2002 | Hastings et al. |
| 6,402,735 | B1 | 6/2002 | Langevin |
| 6,402,746 | B1 | 6/2002 | Whayne et al. |
| 6,406,440 | B1 | 6/2002 | Stefanchik |
| 6,409,727 | B1 | 6/2002 | Bales et al. |
| 6,409,733 | B1 | 6/2002 | Conlon et al. |
| 6,419,639 | B2 | 7/2002 | Walther et al. |
| 6,419,641 | B1 | 7/2002 | Mark et al. |
| 6,427,089 | B1 | 7/2002 | Knowlton |
| 6,431,500 | B1 | 8/2002 | Jacobs et al. |
| 6,436,107 | B1 | 8/2002 | Wang et al. |
| 6,443,970 | B1 | 9/2002 | Schulze et al. |
| 6,443,988 | B2 | 9/2002 | Felt et al. |
| 6,447,444 | B1 | 9/2002 | Avni et al. |
| 6,447,511 | B1 | 9/2002 | Slater |
| 6,447,523 | B1 | 9/2002 | Middleman et al. |
| 6,454,783 | B1 | 9/2002 | Piskun |
| 6,454,785 | B2 | 9/2002 | De Hoyos Garza |
| 6,458,074 | B1 | 10/2002 | Matsui et al. |
| 6,458,076 | B1 | 10/2002 | Pruitt |
| 6,464,701 | B1 | 10/2002 | Hooven et al. |
| 6,464,702 | B2 | 10/2002 | Schulze et al. |
| 6,470,218 | B1 | 10/2002 | Behl |
| 6,475,104 | B1 | 11/2002 | Lutz et al. |
| 6,485,411 | B1 | 11/2002 | Konstorum et al. |
| 6,489,745 | B1 | 12/2002 | Koreis |
| 6,491,626 | B1 | 12/2002 | Stone et al. |
| 6,491,627 | B1 | 12/2002 | Komi |
| 6,491,691 | B1 | 12/2002 | Morley et al. |
| 6,493,590 | B1 | 12/2002 | Wessman et al. |
| 6,494,893 | B2 | 12/2002 | Dubrul et al. |
| 6,500,176 | B1 | 12/2002 | Truckai et al. |
| 6,503,192 | B1 | 1/2003 | Ouchi |
| 6,506,190 | B1 | 1/2003 | Walshe |
| 6,508,827 | B1 | 1/2003 | Manhes |
| 6,514,239 | B2 | 2/2003 | Shimmura et al. |
| 6,517,534 | B1 | 2/2003 | McGovern et al. |
| 6,520,954 | B2 | 2/2003 | Ouchi |
| 6,526,320 | B2 | 2/2003 | Mitchell |
| 6,527,753 | B2 | 3/2003 | Sekine et al. |
| 6,527,782 | B2 | 3/2003 | Hogg et al. |
| 6,530,880 | B2 | 3/2003 | Pagliuca |
| 6,530,922 | B2 | 3/2003 | Cosman et al. |
| 6,535,764 | B2 | 3/2003 | Imran et al. |
| 6,537,200 | B2 | 3/2003 | Leysieffer et al. |
| 6,543,456 | B1 | 4/2003 | Freeman |
| 6,551,270 | B1 | 4/2003 | Bimbo et al. |
| 6,551,356 | B2 | 4/2003 | Rousseau |
| 6,554,766 | B2 | 4/2003 | Maeda et al. |
| 6,554,823 | B2 | 4/2003 | Palmer et al. |
| 6,554,829 | B2 | 4/2003 | Schulze et al. |
| 6,558,384 | B2 | 5/2003 | Mayenberger |
| 6,562,034 | B2 | 5/2003 | Edwards et al. |
| 6,562,035 | B1 | 5/2003 | Levin |
| 6,562,052 | B2 | 5/2003 | Nobles et al. |
| 6,569,085 | B2 | 5/2003 | Kortenbach et al. |
| 6,569,091 | B2 | 5/2003 | Diokno et al. |
| 6,569,120 | B1 * | 5/2003 | Green .................. A61B 17/34 137/849 |
| 6,569,159 | B1 | 5/2003 | Edwards et al. |
| 6,572,629 | B2 | 6/2003 | Kalloo et al. |
| 6,572,635 | B1 | 6/2003 | Bonutti |
| 6,575,988 | B2 | 6/2003 | Rousseau |
| 6,579,311 | B1 | 6/2003 | Makower |
| 6,581,889 | B2 | 6/2003 | Carpenter et al. |
| 6,585,642 | B2 | 7/2003 | Christopher |
| 6,585,717 | B1 | 7/2003 | Wittenberger et al. |
| 6,587,750 | B2 | 7/2003 | Gerbi et al. |
| 6,592,559 | B1 | 7/2003 | Pakter et al. |
| 6,592,603 | B2 | 7/2003 | Lasner |
| 6,594,971 | B1 | 7/2003 | Addy et al. |
| 6,602,262 | B2 | 8/2003 | Griego et al. |
| 6,605,105 | B1 | 8/2003 | Cuschieri et al. |
| 6,610,072 | B1 | 8/2003 | Christy et al. |
| 6,610,074 | B2 | 8/2003 | Santilli |
| 6,613,038 | B2 | 9/2003 | Bonutti et al. |
| 6,613,068 | B2 | 9/2003 | Ouchi |
| 6,616,632 | B2 | 9/2003 | Sharp et al. |
| 6,620,193 | B1 | 9/2003 | Lau et al. |
| 6,623,448 | B2 | 9/2003 | Slater |
| 6,626,919 | B1 | 9/2003 | Swanstrom |
| 6,632,171 | B2 | 10/2003 | Iddan et al. |
| 6,632,229 | B1 | 10/2003 | Yamanouchi |
| 6,632,234 | B2 | 10/2003 | Kieturakis et al. |
| 6,638,275 | B1 | 10/2003 | McGaffigan et al. |
| 6,638,286 | B1 | 10/2003 | Burbank et al. |

(56) References Cited

U.S. PATENT DOCUMENTS

| | | |
|---|---|---|
| 6,645,225 B1 | 11/2003 | Atkinson |
| 6,652,518 B2 | 11/2003 | Wellman et al. |
| 6,652,521 B2 | 11/2003 | Schulze |
| 6,652,545 B2 | 11/2003 | Shipp et al. |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,070 B2 | 1/2004 | Edwards et al. |
| 6,673,087 B1 | 1/2004 | Chang et al. |
| 6,673,092 B1 | 1/2004 | Bacher |
| 6,676,685 B2 | 1/2004 | Pedros et al. |
| 6,679,882 B1 | 1/2004 | Kornerup |
| 6,684,938 B2 | 2/2004 | Tsujita et al. |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,695,867 B2 | 2/2004 | Ginn et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,740,082 B2 | 5/2004 | Shadduck |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,767,356 B2 | 7/2004 | Kanner et al. |
| 6,773,434 B2 | 8/2004 | Ciarrocca |
| 6,776,165 B2 | 8/2004 | Jin |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,814,697 B2 | 11/2004 | Ouchi |
| 6,817,974 B2 | 11/2004 | Cooper et al. |
| 6,818,007 B1 | 11/2004 | Dampney et al. |
| 6,821,285 B2 | 11/2004 | Laufer et al. |
| 6,824,548 B2 | 11/2004 | Smith et al. |
| 6,830,545 B2 | 12/2004 | Bendall |
| 6,835,200 B2 | 12/2004 | Laufer et al. |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,852,078 B2 | 2/2005 | Ouchi |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,869,395 B2 | 3/2005 | Page et al. |
| 6,869,398 B2 | 3/2005 | Obenchain et al. |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,911,019 B2 | 6/2005 | Mulier et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,906 B2 | 7/2005 | Long |
| 6,918,908 B2 | 7/2005 | Bonner et al. |
| 6,926,723 B1 | 8/2005 | Mulhauser et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |
| 6,939,347 B2 | 9/2005 | Thompson |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,949,096 B2 | 9/2005 | Davison et al. |
| 6,955,641 B2 | 10/2005 | Lubock |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,960,183 B2 | 11/2005 | Nicolette |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,980,858 B2 | 12/2005 | Fuimaono et al. |
| 6,984,203 B2 | 1/2006 | Tartaglia et al. |
| 6,984,205 B2 | 1/2006 | Gazdzinski |
| 6,986,738 B2 | 1/2006 | Glukhovsky et al. |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,602 B2 | 1/2006 | Nakazawa et al. |
| 6,991,627 B2 | 1/2006 | Madhani et al. |
| 6,991,631 B2 | 1/2006 | Woloszko et al. |
| 6,994,706 B2 | 2/2006 | Chornenky et al. |
| 6,994,708 B2 | 2/2006 | Manzo |
| 6,997,870 B2 | 2/2006 | Couvillon, Jr. |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |

(56) References Cited

U.S. PATENT DOCUMENTS

| | | |
|---|---|---|
| 7,011,669 B2 | 3/2006 | Kimblad |
| 7,018,373 B2 | 3/2006 | Suzuki |
| 7,020,531 B1 | 3/2006 | Colliou et al. |
| 7,025,580 B2 | 4/2006 | Heagy et al. |
| 7,025,721 B2 | 4/2006 | Cohen et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,454 B2 | 5/2006 | Taylor |
| 7,052,489 B2 | 5/2006 | Griego et al. |
| 7,056,330 B2 | 6/2006 | Gayton |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,559 B2 | 7/2006 | Adams et al. |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,010 B2 | 8/2006 | Ootawara et al. |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,115,785 B2 | 10/2006 | Guggenheim et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,122,605 B2 | 10/2006 | Ohrbom et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,156,845 B2 | 1/2007 | Mulier et al. |
| 7,160,296 B2 | 1/2007 | Pearson et al. |
| 7,163,525 B2 | 1/2007 | Franer |
| 7,169,104 B2 | 1/2007 | Ueda et al. |
| 7,169,115 B2 | 1/2007 | Nobis et al. |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,186,265 B2 | 3/2007 | Sharkawy et al. |
| 7,188,627 B2 | 3/2007 | Nelson et al. |
| 7,189,231 B2 | 3/2007 | Clague et al. |
| 7,195,612 B2 | 3/2007 | van Sloten et al. |
| 7,195,631 B2 | 3/2007 | Dumbauld |
| 7,204,804 B2 | 4/2007 | Zirps et al. |
| 7,204,820 B2 | 4/2007 | Akahoshi |
| 7,204,840 B2 | 4/2007 | Skakoon et al. |
| 7,207,997 B2 | 4/2007 | Shipp et al. |
| 7,208,005 B2 | 4/2007 | Frecker et al. |
| 7,211,089 B2 | 5/2007 | Kear et al. |
| 7,211,092 B2 | 5/2007 | Hughett |
| 7,220,227 B2 | 5/2007 | Sasaki et al. |
| 7,223,271 B2 | 5/2007 | Muramatsu et al. |
| 7,223,272 B2 | 5/2007 | Francese et al. |
| 7,226,458 B2 | 6/2007 | Kaplan et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,084 B2 | 6/2007 | Skakoon et al. |
| 7,235,089 B1 | 6/2007 | McGuckin, Jr. |
| 7,241,290 B2 | 7/2007 | Doyle et al. |
| 7,241,295 B2 | 7/2007 | Maguire |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,261,728 B2 | 8/2007 | Long et al. |
| 7,270,663 B2 | 9/2007 | Nakao |
| 7,288,075 B2 | 10/2007 | Parihar et al. |
| 7,290,615 B2 | 11/2007 | Christanti et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,311,107 B2 | 12/2007 | Harel et al. |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,331,968 B2 | 2/2008 | Arp et al. |
| 7,335,220 B2 | 2/2008 | Khosravi et al. |
| 7,341,554 B2 | 3/2008 | Sekine et al. |
| 7,344,536 B1 | 3/2008 | Lunsford et al. |
| 7,349,223 B2 | 3/2008 | Haemer et al. |
| 7,352,387 B2 | 4/2008 | Yamamoto |
| 7,357,806 B2 | 4/2008 | Rivera et al. |
| 7,364,582 B2 | 4/2008 | Lee |
| 7,367,939 B2 | 5/2008 | Smith et al. |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,431,694 B2 | 10/2008 | Stefanchik et al. |
| 7,435,229 B2 | 10/2008 | Wolf |
| 7,435,257 B2 | 10/2008 | Lashinski et al. |
| 7,441,507 B2 | 10/2008 | Teraura et al. |
| 7,442,166 B2 | 10/2008 | Huang et al. |
| 7,452,327 B2 | 11/2008 | Durgin et al. |
| 7,455,208 B2 | 11/2008 | Wales et al. |
| 7,455,675 B2 | 11/2008 | Schur et al. |
| 7,468,066 B2 | 12/2008 | Vargas et al. |
| 7,476,237 B2 | 1/2009 | Taniguchi et al. |
| 7,479,104 B2 | 1/2009 | Lau et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |

(56) References Cited

U.S. PATENT DOCUMENTS

| | | |
|---|---|---|
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,514,568 B2 | 4/2009 | Freeman |
| 7,515,953 B2 | 4/2009 | Madar et al. |
| 7,520,876 B2 | 4/2009 | Ressemann et al. |
| 7,520,950 B2 | 4/2009 | Saadat et al. |
| 7,524,281 B2 | 4/2009 | Chu et al. |
| 7,524,302 B2 | 4/2009 | Tower |
| 7,534,228 B2 | 5/2009 | Williams |
| 7,535,570 B2 | 5/2009 | Muraishi |
| 7,536,217 B2 | 5/2009 | Minai et al. |
| 7,540,872 B2 | 6/2009 | Schechter et al. |
| 7,542,807 B2 | 6/2009 | Bertolero et al. |
| 7,544,195 B2 | 6/2009 | Lunsford et al. |
| 7,544,203 B2 | 6/2009 | Chin et al. |
| 7,547,310 B2 | 6/2009 | Whitfield |
| 7,548,040 B2 | 6/2009 | Lee et al. |
| 7,549,564 B2 | 6/2009 | Boudreaux |
| 7,549,990 B2 | 6/2009 | Canady |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,300 B2 | 7/2009 | Devierre et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,578,832 B2 | 8/2009 | Johnson et al. |
| 7,579,005 B2 | 8/2009 | Keeler et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,591,781 B2 | 9/2009 | Hirata |
| 7,591,783 B2 | 9/2009 | Boulais et al. |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,612,084 B2 | 11/2009 | James et al. |
| 7,615,002 B2 | 11/2009 | Rothweiler et al. |
| 7,615,003 B2 | 11/2009 | Stefanchik et al. |
| 7,615,005 B2 | 11/2009 | Stefanchik et al. |
| 7,615,058 B2 | 11/2009 | Sixto, Jr. et al. |
| 7,615,067 B2 | 11/2009 | Lee et al. |
| 7,618,398 B2 | 11/2009 | Holman et al. |
| 7,618,437 B2 | 11/2009 | Nakao |
| 7,621,927 B2 | 11/2009 | Messerly et al. |
| 7,621,936 B2 | 11/2009 | Cragg et al. |
| 7,628,792 B2 | 12/2009 | Guerra |
| 7,628,797 B2 | 12/2009 | Tieu et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,637,905 B2 | 12/2009 | Saadat et al. |
| 7,645,288 B2 | 1/2010 | McKenna et al. |
| 7,648,457 B2 | 1/2010 | Stefanchik et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,658,738 B2 | 2/2010 | Nobis et al. |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,282 B2 | 3/2010 | Mathis |
| 7,670,336 B2 | 3/2010 | Young et al. |
| 7,670,346 B2 | 3/2010 | Whitfield |
| 7,674,259 B2 | 3/2010 | Shadduck |
| 7,674,275 B2 | 3/2010 | Martin et al. |
| 7,678,043 B2 | 3/2010 | Gilad |
| 7,680,543 B2 | 3/2010 | Azure |
| 7,684,599 B2 | 3/2010 | Horn et al. |
| 7,684,851 B2 | 3/2010 | Miyake et al. |
| 7,686,826 B2 | 3/2010 | Lee et al. |
| 7,691,103 B2 | 4/2010 | Fernandez et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,708,756 B2 | 5/2010 | Nobis et al. |
| 7,710,563 B2 | 5/2010 | Betzig et al. |
| 7,713,189 B2 | 5/2010 | Hanke |
| 7,713,270 B2 | 5/2010 | Suzuki |
| 7,721,742 B2 | 5/2010 | Kalloo et al. |
| 7,722,631 B2 | 5/2010 | Mikkaichi et al. |
| 7,727,242 B2 | 6/2010 | Sepetka et al. |
| 7,727,246 B2 | 6/2010 | Sixto, Jr. et al. |
| 7,727,248 B2 | 6/2010 | Smith et al. |
| 7,727,249 B2 | 6/2010 | Rahmani |
| 7,731,725 B2 | 6/2010 | Gadberry et al. |
| 7,736,374 B2 | 6/2010 | Vaughan et al. |
| 7,744,591 B2 | 6/2010 | Rioux et al. |
| 7,744,613 B2 | 6/2010 | Ewers et al. |
| 7,744,615 B2 | 6/2010 | Couture |
| 7,749,161 B2 | 7/2010 | Beckman et al. |
| 7,749,163 B2 | 7/2010 | Mulac et al. |
| 7,751,866 B2 | 7/2010 | Aoki et al. |
| 7,751,869 B2 | 7/2010 | Rioux et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,758,598 B2 | 7/2010 | Conlon et al. |
| 7,762,949 B2 | 7/2010 | Nakao |
| 7,762,959 B2 | 7/2010 | Bilsbury |
| 7,762,960 B2 | 7/2010 | Timberlake et al. |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,766,896 B2 | 8/2010 | Kornkven Volk et al. |
| 7,770,584 B2 | 8/2010 | Danek et al. |
| 7,771,416 B2 | 8/2010 | Spivey et al. |
| 7,771,437 B2 | 8/2010 | Hogg et al. |
| 7,776,035 B2 | 8/2010 | Rick et al. |
| 7,780,639 B2 | 8/2010 | Van Lue |
| 7,780,683 B2 | 8/2010 | Roue et al. |
| 7,780,691 B2 | 8/2010 | Stefanchik |
| 7,784,663 B2 | 8/2010 | Shelton, IV |
| 7,785,348 B2 | 8/2010 | Kuhns et al. |
| 7,789,825 B2 | 9/2010 | Nobis et al. |
| 7,794,409 B2 | 9/2010 | Damarati |
| 7,794,447 B2 | 9/2010 | Dann et al. |
| 7,794,458 B2 | 9/2010 | McIntyre et al. |
| 7,794,475 B2 | 9/2010 | Hess et al. |
| 7,798,386 B2 | 9/2010 | Schall et al. |
| 7,798,750 B2 | 9/2010 | Clark |
| 7,798,960 B2 | 9/2010 | Jaeger |
| 7,813,590 B2 | 10/2010 | Horn et al. |
| 7,813,789 B2 | 10/2010 | Glukhovsky |
| 7,815,565 B2 | 10/2010 | Stefanchik et al. |
| 7,815,566 B2 | 10/2010 | Stefanchik et al. |
| 7,815,651 B2 | 10/2010 | Skakoon et al. |
| 7,815,659 B2 | 10/2010 | Conlon et al. |
| 7,815,662 B2 | 10/2010 | Spivey et al. |
| 7,819,836 B2 | 10/2010 | Levine et al. |
| 7,828,186 B2 | 11/2010 | Wales |
| 7,828,808 B2 | 11/2010 | Hinman et al. |
| 7,828,809 B2 | 11/2010 | Skakoon et al. |
| 7,833,156 B2 | 11/2010 | Williams et al. |
| 7,833,231 B2 | 11/2010 | Skakoon et al. |
| 7,833,238 B2 | 11/2010 | Nakao |
| 7,837,615 B2 | 11/2010 | Le et al. |
| 7,842,028 B2 | 11/2010 | Lee |

(56) References Cited

U.S. PATENT DOCUMENTS

| | | |
|---|---|---|
| 7,842,050 B2 | 11/2010 | Diduch et al. |
| 7,842,068 B2 | 11/2010 | Ginn |
| 7,846,087 B2 | 12/2010 | Stefanchik et al. |
| 7,846,107 B2 | 12/2010 | Hoffman et al. |
| 7,846,171 B2 | 12/2010 | Kullas et al. |
| 7,850,660 B2 | 12/2010 | Uth et al. |
| 7,850,686 B2 | 12/2010 | Nobis et al. |
| 7,850,712 B2 | 12/2010 | Conlon et al. |
| 7,857,183 B2 | 12/2010 | Shelton, IV |
| 7,857,820 B2 | 12/2010 | Skakoon et al. |
| 7,862,546 B2 | 1/2011 | Conlon et al. |
| 7,862,553 B2 | 1/2011 | Ewaschuk |
| 7,862,572 B2 | 1/2011 | Meade et al. |
| 7,862,582 B2 | 1/2011 | Ortiz et al. |
| 7,867,216 B2 | 1/2011 | Wahr et al. |
| 7,871,371 B2 | 1/2011 | Komiya et al. |
| 7,875,042 B2 | 1/2011 | Martin et al. |
| 7,879,004 B2 | 2/2011 | Seibel et al. |
| 7,883,458 B2 | 2/2011 | Hamel |
| 7,887,530 B2 | 2/2011 | Zemlok et al. |
| 7,887,558 B2 | 2/2011 | Lin et al. |
| 7,892,200 B2 | 2/2011 | Birk et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,905,830 B2 | 3/2011 | Stefanchik et al. |
| 7,909,809 B2 | 3/2011 | Scopton et al. |
| 7,914,513 B2 | 3/2011 | Voorhees, Jr. |
| 7,916,809 B2 | 3/2011 | Tsushima |
| 7,918,783 B2 | 4/2011 | Maseda et al. |
| 7,918,785 B2 | 4/2011 | Okada et al. |
| 7,918,844 B2 | 4/2011 | Byrum et al. |
| 7,918,845 B2 | 4/2011 | Saadat et al. |
| 7,918,848 B2 | 4/2011 | Lau et al. |
| 7,918,869 B2 | 4/2011 | Saadat et al. |
| 7,922,650 B2 | 4/2011 | McWeeney et al. |
| 7,922,717 B2 | 4/2011 | Sugita |
| 7,922,739 B2 | 4/2011 | Downey |
| 7,922,743 B2 | 4/2011 | Heinrich et al. |
| 7,927,271 B2 | 4/2011 | Dimitriou et al. |
| 7,931,624 B2 | 4/2011 | Smith et al. |
| 7,931,661 B2 | 4/2011 | Saadat et al. |
| 7,935,130 B2 | 5/2011 | Williams |
| 7,937,143 B2 | 5/2011 | Demarais et al. |
| 7,945,332 B2 | 5/2011 | Schechter |
| 7,947,000 B2 | 5/2011 | Vargas et al. |
| 7,951,073 B2 | 5/2011 | Freed |
| 7,953,326 B2 | 5/2011 | Farr et al. |
| 7,955,298 B2 | 6/2011 | Carroll et al. |
| 7,955,340 B2 | 6/2011 | Michlitsch et al. |
| 7,955,355 B2 | 6/2011 | Chin |
| 7,959,627 B2 | 6/2011 | Utley et al. |
| 7,959,629 B2 | 6/2011 | Young et al. |
| 7,959,642 B2 | 6/2011 | Nobis et al. |
| 7,963,192 B2 | 6/2011 | Mayenberger et al. |
| 7,963,912 B2 | 6/2011 | Zwolinski et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,967,842 B2 | 6/2011 | Bakos |
| 7,969,473 B2 | 6/2011 | Kotoda |
| 7,972,330 B2 | 7/2011 | Alejandro et al. |
| 7,972,333 B2 | 7/2011 | Nishimura |
| 7,976,458 B2 | 7/2011 | Stefanchik et al. |
| 7,976,552 B2 | 7/2011 | Suzuki |
| 7,985,239 B2 | 7/2011 | Suzuki |
| 7,985,830 B2 | 7/2011 | Mance et al. |
| 7,988,618 B2 | 8/2011 | Mikkaichi et al. |
| 7,988,685 B2 | 8/2011 | Ziaie et al. |
| 7,988,690 B2 | 8/2011 | Chanduszko et al. |
| 7,998,132 B2 | 8/2011 | Gregorich et al. |
| 8,007,474 B2 | 8/2011 | Uth et al. |
| 8,007,495 B2 | 8/2011 | McDaniel et al. |
| 8,021,358 B2 | 9/2011 | Doyle et al. |
| 8,021,362 B2 | 9/2011 | Deem et al. |
| 8,021,378 B2 | 9/2011 | Sixto, Jr. et al. |
| 8,029,504 B2 | 10/2011 | Long |
| 8,034,046 B2 | 10/2011 | Eidenschink |
| 8,037,591 B2 | 10/2011 | Spivey et al. |
| 8,038,596 B2 | 10/2011 | Miyake et al. |
| 8,038,612 B2 | 10/2011 | Paz |
| 8,043,289 B2 | 10/2011 | Behl et al. |
| 8,048,060 B2 | 11/2011 | Griffin et al. |
| 8,048,067 B2 | 11/2011 | Davalos et al. |
| 8,048,108 B2 | 11/2011 | Sibbitt, Jr. et al. |
| 8,052,597 B2 | 11/2011 | Boulais |
| 8,052,699 B1 | 11/2011 | Sherwinter |
| 8,057,462 B2 | 11/2011 | Weitzner et al. |
| 8,057,510 B2 | 11/2011 | Ginn et al. |
| 8,062,306 B2 | 11/2011 | Nobis et al. |
| 8,062,311 B2 | 11/2011 | Litscher et al. |
| 8,066,632 B2 | 11/2011 | Dario et al. |
| 8,066,702 B2 | 11/2011 | Rittman, III et al. |
| 8,070,743 B2 | 12/2011 | Kagan et al. |
| 8,070,759 B2 | 12/2011 | Stefanchik et al. |
| 8,070,804 B2 | 12/2011 | Hyde et al. |
| 8,075,478 B2 | 12/2011 | Campos |
| 8,075,567 B2 | 12/2011 | Taylor et al. |
| 8,075,572 B2 | 12/2011 | Stefanchik et al. |
| 8,075,573 B2 | 12/2011 | Gambale et al. |
| 8,075,587 B2 | 12/2011 | Ginn |
| 8,083,787 B2 | 12/2011 | Korb et al. |
| 8,088,062 B2 | 1/2012 | Zwolinski |
| 8,092,374 B2 | 1/2012 | Smith et al. |
| 8,092,549 B2 | 1/2012 | Hillis et al. |
| 8,096,459 B2 | 1/2012 | Ortiz et al. |
| 8,096,941 B2 | 1/2012 | Fowler et al. |
| 8,096,998 B2 | 1/2012 | Cresina |
| 8,097,001 B2 | 1/2012 | Nakao |
| 8,100,922 B2 | 1/2012 | Griffith |
| 8,105,342 B2 | 1/2012 | Onuki et al. |
| 8,109,872 B2 | 2/2012 | Kennedy, II et al. |
| 8,109,919 B2 | 2/2012 | Kraft et al. |
| 8,109,926 B2 | 2/2012 | Azure |
| 8,114,072 B2 | 2/2012 | Long et al. |
| 8,114,113 B2 | 2/2012 | Becker |
| 8,114,119 B2 | 2/2012 | Spivey et al. |
| 8,115,447 B2 | 2/2012 | Toya et al. |
| 8,118,738 B2 | 2/2012 | Larkin |
| 8,118,821 B2 | 2/2012 | Mouw |
| 8,118,834 B1 | 2/2012 | Goraltchouk et al. |
| 8,118,835 B2 | 2/2012 | Weisel et al. |
| 8,123,677 B2 | 2/2012 | Fujimori |
| 8,131,371 B2 | 3/2012 | Demarals et al. |
| 8,147,424 B2 | 4/2012 | Kassab et al. |
| 8,157,813 B2 | 4/2012 | Ko et al. |
| 8,157,817 B2 | 4/2012 | Bonadio et al. |
| 8,157,834 B2 | 4/2012 | Conlon |
| 8,159,549 B2 | 4/2012 | Glukhovsky et al. |
| 8,167,894 B2 | 5/2012 | Miles et al. |
| 8,172,772 B2 | 5/2012 | Zwolinski et al. |
| 8,182,414 B2 | 5/2012 | Handa et al. |
| 8,187,166 B2 | 5/2012 | Kuth et al. |
| 8,200,334 B1 | 6/2012 | Min et al. |
| 8,202,265 B2 | 6/2012 | Boulais |
| 8,202,295 B2 | 6/2012 | Kaplan |
| 8,206,295 B2 | 6/2012 | Kaul |
| 8,211,119 B2 | 7/2012 | Palmer et al. |
| 8,211,125 B2 | 7/2012 | Spivey |
| 8,216,224 B2 | 7/2012 | Morris et al. |
| 8,216,252 B2 | 7/2012 | Vaughan et al. |
| 8,216,255 B2 | 7/2012 | Smith et al. |
| 8,221,310 B2 | 7/2012 | Saadat et al. |
| 8,221,411 B2 | 7/2012 | Francischelli et al. |
| 8,222,385 B2 | 7/2012 | Yoshizaki et al. |
| 8,241,204 B2 | 8/2012 | Spivey |
| 8,241,309 B2 | 8/2012 | Miles et al. |
| 8,246,633 B2 | 8/2012 | Omori |
| 8,251,068 B2 | 8/2012 | Schnell |
| 8,252,057 B2 | 8/2012 | Fox |
| 8,262,563 B2 | 9/2012 | Bakos et al. |
| 8,262,655 B2 | 9/2012 | Ghabrial et al. |
| 8,262,680 B2 | 9/2012 | Swain et al. |

(56) References Cited

U.S. PATENT DOCUMENTS

| | | |
|---|---|---|
| 8,267,854 B2 | 9/2012 | Asada et al. |
| 8,277,373 B2 | 10/2012 | Maahs et al. |
| 8,282,665 B2 | 10/2012 | Kieturakis et al. |
| 8,298,161 B2 | 10/2012 | Vargas |
| 8,303,581 B2 | 11/2012 | Arts et al. |
| 8,308,682 B2 | 11/2012 | Kramer et al. |
| 8,308,738 B2 | 11/2012 | Nobis et al. |
| 8,308,743 B2 | 11/2012 | Matsuno et al. |
| 8,313,496 B2 | 11/2012 | Sauer et al. |
| 8,317,806 B2 | 11/2012 | Coe et al. |
| 8,317,814 B2 | 11/2012 | Karasawa et al. |
| 8,328,836 B2 | 12/2012 | Conlon et al. |
| 8,333,691 B2 | 12/2012 | Schaaf |
| 8,333,777 B2 | 12/2012 | Schaller et al. |
| 8,337,394 B2 | 12/2012 | Vakharia |
| 8,337,492 B2 | 12/2012 | Kunis et al. |
| 8,337,510 B2 | 12/2012 | Rieber et al. |
| 8,348,827 B2 | 1/2013 | Zwolinski |
| 8,353,487 B2 | 1/2013 | Trusty et al. |
| 8,357,170 B2 | 1/2013 | Stefanchik |
| 8,359,093 B2 | 1/2013 | Wariar |
| 8,361,066 B2 | 1/2013 | Long et al. |
| 8,361,112 B2 | 1/2013 | Carroll, II et al. |
| 8,366,606 B2 | 2/2013 | Watanabe et al. |
| 8,366,733 B2 | 2/2013 | Gabel et al. |
| 8,377,044 B2 | 2/2013 | Coe et al. |
| 8,377,057 B2 | 2/2013 | Rick et al. |
| 8,382,790 B2 | 2/2013 | Uenohara et al. |
| 8,388,653 B2 | 3/2013 | Nobis et al. |
| 8,394,090 B2 | 3/2013 | Ootsubo |
| 8,403,926 B2 | 3/2013 | Nobis et al. |
| 8,409,076 B2 | 4/2013 | Pang et al. |
| 8,409,197 B2 | 4/2013 | Slater |
| 8,409,200 B2 | 4/2013 | Holcomb et al. |
| 8,425,505 B2 | 4/2013 | Long |
| 8,430,811 B2 | 4/2013 | Hess et al. |
| 8,449,452 B2 | 5/2013 | Iddan et al. |
| 8,449,538 B2 | 5/2013 | Long |
| 8,454,594 B2 | 6/2013 | Demarais et al. |
| 8,460,275 B2 | 6/2013 | Taylor et al. |
| 8,465,419 B2 | 6/2013 | Moriyama |
| 8,465,484 B2 | 6/2013 | Davalos et al. |
| 8,469,993 B2 | 6/2013 | Rothberg et al. |
| 8,475,359 B2 | 7/2013 | Asada et al. |
| 8,475,361 B2 | 7/2013 | Barlow et al. |
| 8,475,452 B2 | 7/2013 | Van Wyk et al. |
| 8,480,657 B2 | 7/2013 | Bakos |
| 8,480,689 B2 | 7/2013 | Spivey et al. |
| 8,485,968 B2 | 7/2013 | Weimer et al. |
| 8,496,574 B2 | 7/2013 | Trusty et al. |
| 8,500,697 B2 | 8/2013 | Kurth et al. |
| 8,506,564 B2 | 8/2013 | Long et al. |
| 8,512,335 B2 | 8/2013 | Cheng et al. |
| 8,517,921 B2 | 8/2013 | Tremaglio et al. |
| 8,518,024 B2 | 8/2013 | Williams et al. |
| 8,518,052 B2 | 8/2013 | Burgermeister et al. |
| 8,518,062 B2 | 8/2013 | Cole et al. |
| 8,523,884 B2 | 9/2013 | Stam et al. |
| 8,523,939 B1 | 9/2013 | Hausen |
| 8,529,563 B2 | 9/2013 | Long et al. |
| 8,540,744 B2 | 9/2013 | Spivey et al. |
| 8,545,396 B2 | 10/2013 | Cover et al. |
| 8,545,450 B2 | 10/2013 | Voegele et al. |
| 8,551,058 B2 | 10/2013 | Measamer et al. |
| 8,562,513 B2 | 10/2013 | Yamatani |
| 8,562,602 B2 | 10/2013 | Azure |
| 8,568,410 B2 | 10/2013 | Vakharia et al. |
| 8,579,176 B2 | 11/2013 | Smith et al. |
| 8,579,897 B2 | 11/2013 | Vakharia et al. |
| 8,602,970 B2 | 12/2013 | Muyari et al. |
| 8,603,138 B2 | 12/2013 | Faller et al. |
| 8,608,652 B2 | 12/2013 | Voegele et al. |
| 8,617,156 B2 | 12/2013 | Werneth et al. |
| 8,623,011 B2 | 1/2014 | Spivey |
| 8,632,534 B2 | 1/2014 | Pearson et al. |
| 8,632,563 B2 | 1/2014 | Nagase et al. |
| 8,636,648 B2 | 1/2014 | Gazdzinski |
| 8,636,650 B2 | 1/2014 | Lee |
| 8,636,730 B2 | 1/2014 | Keppel |
| 8,640,940 B2 | 2/2014 | Ohdaira |
| 8,641,728 B2 | 2/2014 | Stokes et al. |
| 8,652,150 B2 | 2/2014 | Swain et al. |
| 8,657,174 B2 | 2/2014 | Yates et al. |
| 8,663,236 B2 | 3/2014 | Chen et al. |
| 8,668,686 B2 | 3/2014 | Govari et al. |
| 8,679,003 B2 | 3/2014 | Spivey |
| 8,684,967 B2 | 4/2014 | Engel et al. |
| 8,685,058 B2 | 4/2014 | Wilk |
| 8,704,923 B2 | 4/2014 | Ogasawara et al. |
| 8,715,281 B2 | 5/2014 | Barlow et al. |
| 8,721,658 B2 | 5/2014 | Kahle et al. |
| 8,723,936 B2 | 5/2014 | Amling et al. |
| 8,727,967 B2 | 5/2014 | Weitzner |
| 8,747,401 B2 | 6/2014 | Gonzalez et al. |
| 8,753,262 B2 | 6/2014 | Sugiyama et al. |
| 8,753,335 B2 | 6/2014 | Moshe et al. |
| 8,764,735 B2 | 7/2014 | Coe et al. |
| 8,771,173 B2 | 7/2014 | Fonger et al. |
| 8,771,260 B2 | 7/2014 | Conlon et al. |
| 8,774,913 B2 | 7/2014 | Demarais et al. |
| 8,784,436 B2 | 7/2014 | Ho et al. |
| 8,795,161 B2 | 8/2014 | Carter |
| 8,821,520 B2 | 9/2014 | Schwemberger et al. |
| 8,821,532 B2 | 9/2014 | Schaeffer |
| 8,828,031 B2 | 9/2014 | Fox et al. |
| 8,834,461 B2 | 9/2014 | Werneth et al. |
| 8,845,656 B2 | 9/2014 | Skakoon et al. |
| 8,858,590 B2 | 10/2014 | Shelton, IV et al. |
| 8,876,701 B2 | 11/2014 | Surti et al. |
| 8,876,772 B2 | 11/2014 | Weber et al. |
| 8,880,185 B2 | 11/2014 | Hastings et al. |
| 8,882,786 B2 | 11/2014 | Bearinger et al. |
| 8,888,792 B2 | 11/2014 | Harris et al. |
| 8,906,035 B2 | 12/2014 | Zwolinski et al. |
| 8,911,452 B2 | 12/2014 | Skakoon et al. |
| 8,920,442 B2 | 12/2014 | Sibbitt, Jr. et al. |
| 8,926,606 B2 | 1/2015 | Davalos et al. |
| 8,932,208 B2 | 1/2015 | Kendale et al. |
| 8,939,897 B2 | 1/2015 | Nobis |
| 8,956,352 B2 | 2/2015 | Mauch et al. |
| 8,974,374 B2 | 3/2015 | Schostek et al. |
| 8,986,199 B2 | 3/2015 | Weisenburgh, II et al. |
| 8,992,517 B2 | 3/2015 | Davalos et al. |
| 9,005,198 B2 | 4/2015 | Long et al. |
| 9,011,431 B2 | 4/2015 | Long et al. |
| 9,028,483 B2 | 5/2015 | Long et al. |
| 9,036,015 B2 | 5/2015 | Verburgh et al. |
| 9,049,987 B2 | 6/2015 | Conlon et al. |
| 9,060,782 B2 | 6/2015 | Daniel et al. |
| 9,066,655 B2 | 6/2015 | Stefanchik et al. |
| 9,078,662 B2 | 7/2015 | Bakos et al. |
| 9,084,621 B2 | 7/2015 | Weitzner et al. |
| 9,089,323 B2 | 7/2015 | Bonutti et al. |
| 9,125,557 B2 | 9/2015 | Lien et al. |
| 9,125,631 B2 | 9/2015 | Smith et al. |
| 9,125,639 B2 | 9/2015 | Mathis et al. |
| 9,149,172 B2 | 10/2015 | Iddan et al. |
| 9,155,587 B2 | 10/2015 | Willis et al. |
| 9,186,203 B2 | 11/2015 | Spivey et al. |
| 9,198,733 B2 | 12/2015 | Neal, II et al. |
| 9,220,526 B2 | 12/2015 | Conlon |
| 9,226,772 B2 | 1/2016 | Fox |
| 9,233,241 B2 | 1/2016 | Long |
| 9,248,278 B2 | 2/2016 | Crosby et al. |
| 9,254,169 B2 | 2/2016 | Long et al. |
| 9,265,407 B2 | 2/2016 | Goldfarb et al. |
| 9,271,796 B2 | 3/2016 | Buysse et al. |
| 9,277,957 B2 | 3/2016 | Long et al. |
| 9,295,485 B2 | 3/2016 | Conlon et al. |
| 9,308,049 B2 | 4/2016 | Dejima |
| 9,314,620 B2 | 4/2016 | Long et al. |
| 9,339,328 B2 | 5/2016 | Ortiz et al. |
| 9,345,462 B2 | 5/2016 | Weitzner et al. |
| 9,352,152 B2 | 5/2016 | Lindenthaler et al. |

(56) References Cited

U.S. PATENT DOCUMENTS

| | | |
|---|---|---|
| 9,370,341 B2 | 6/2016 | Ceniccola et al. |
| 9,375,268 B2 | 6/2016 | Long |
| 9,427,255 B2 | 8/2016 | Griffith et al. |
| 9,486,241 B2 | 11/2016 | Zeiner et al. |
| 9,492,148 B2 | 11/2016 | Ginn et al. |
| 9,545,290 B2 | 1/2017 | Tellio et al. |
| 9,549,719 B2 | 1/2017 | Shohat et al. |
| 9,566,126 B2 | 2/2017 | Weitzner et al. |
| 9,572,623 B2 | 2/2017 | Long |
| 9,598,691 B2 | 3/2017 | Davalos |
| 9,627,120 B2 | 4/2017 | Scott et al. |
| 9,668,725 B2 | 6/2017 | Beaven |
| 9,694,175 B2 | 7/2017 | Tyson, Jr. |
| 9,700,334 B2 | 7/2017 | Hinman et al. |
| 9,788,885 B2 | 10/2017 | Long et al. |
| 9,788,888 B2 | 10/2017 | Bakos et al. |
| 9,788,890 B2 | 10/2017 | Toth et al. |
| 9,808,597 B2 | 11/2017 | Vargas et al. |
| 9,833,282 B2 | 12/2017 | Jun |
| 9,833,595 B2 | 12/2017 | Gonzalez |
| 9,861,272 B2 | 1/2018 | Pell et al. |
| 9,883,910 B2 | 2/2018 | Conlon et al. |
| 9,974,944 B2 | 5/2018 | Sudam et al. |
| 10,004,558 B2 | 6/2018 | Long et al. |
| 2001/0023333 A1 | 9/2001 | Wise et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0068945 A1 | 6/2002 | Sixto et al. |
| 2002/0082551 A1 | 6/2002 | Yachia et al. |
| 2002/0095164 A1 | 7/2002 | Andreas et al. |
| 2002/0133115 A1 | 9/2002 | Gordon et al. |
| 2002/0138086 A1 | 9/2002 | Sixto et al. |
| 2002/0165592 A1 | 11/2002 | Glukhovsky et al. |
| 2003/0014090 A1 | 1/2003 | Abrahamson |
| 2003/0018373 A1 | 1/2003 | Eckhardt et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0187351 A1 | 10/2003 | Franck et al. |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2004/0002683 A1 | 1/2004 | Nicholson et al. |
| 2004/0024414 A1 | 2/2004 | Downing |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0133089 A1 | 7/2004 | Kilcoyne et al. |
| 2004/0136779 A1 | 7/2004 | Bhaskar |
| 2004/0138529 A1 | 7/2004 | Wiltshire et al. |
| 2004/0138587 A1 | 7/2004 | Lyons |
| 2004/0138747 A1 | 7/2004 | Kaladelfos |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0225186 A1 | 11/2004 | Horne et al. |
| 2004/0243108 A1 | 12/2004 | Suzuki |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260315 A1 | 12/2004 | Dell et al. |
| 2004/0260337 A1 | 12/2004 | Freed |
| 2005/0004515 A1 | 1/2005 | Hart et al. |
| 2005/0043690 A1 | 2/2005 | Todd |
| 2005/0059963 A1 | 3/2005 | Phan et al. |
| 2005/0059964 A1 | 3/2005 | Fitz |
| 2005/0065509 A1 | 3/2005 | Coldwell et al. |
| 2005/0070947 A1* | 3/2005 | Franer ............... A61B 17/3462 606/185 |
| 2005/0080435 A1 | 4/2005 | Smith et al. |
| 2005/0085693 A1 | 4/2005 | Belson et al. |
| 2005/0085832 A1 | 4/2005 | Sancoff et al. |
| 2005/0090837 A1 | 4/2005 | Sixto et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131457 A1 | 6/2005 | Douglas et al. |
| 2005/0137454 A1 | 6/2005 | Saadat et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0165272 A1 | 7/2005 | Okada et al. |
| 2005/0165378 A1 | 7/2005 | Heinrich et al. |
| 2005/0165411 A1 | 7/2005 | Orban |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192602 A1 | 9/2005 | Manzo |
| 2005/0209624 A1 | 9/2005 | Vijay |
| 2005/0215858 A1 | 9/2005 | Vail |
| 2005/0216036 A1 | 9/2005 | Nakao |
| 2005/0228224 A1 | 10/2005 | Okada et al. |
| 2005/0228406 A1 | 10/2005 | Bose |
| 2005/0240249 A1 | 10/2005 | Tu et al. |
| 2005/0250987 A1 | 11/2005 | Ewers et al. |
| 2005/0251176 A1 | 11/2005 | Swanstrom et al. |
| 2005/0261711 A1 | 11/2005 | Okada et al. |
| 2005/0267492 A1 | 12/2005 | Poncet et al. |
| 2005/0272977 A1 | 12/2005 | Saadat et al. |
| 2005/0274935 A1 | 12/2005 | Nelson |
| 2005/0277956 A1 | 12/2005 | Francese et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0025654 A1 | 2/2006 | Suzuki et al. |
| 2006/0025781 A1 | 2/2006 | Young et al. |
| 2006/0025812 A1 | 2/2006 | Shelton |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0064083 A1 | 3/2006 | Khalaj et al. |
| 2006/0069424 A1 | 3/2006 | Acosta et al. |
| 2006/0069429 A1 | 3/2006 | Spence et al. |
| 2006/0074413 A1 | 4/2006 | Behzadian |
| 2006/0089528 A1 | 4/2006 | Tartaglia et al. |
| 2006/0095031 A1 | 5/2006 | Ormsby |
| 2006/0100687 A1 | 5/2006 | Fahey et al. |
| 2006/0111210 A1 | 5/2006 | Hinman |
| 2006/0111703 A1 | 5/2006 | Kunis et al. |
| 2006/0111704 A1 | 5/2006 | Brenneman et al. |
| 2006/0129166 A1 | 6/2006 | Lavelle |

(56) References Cited

U.S. PATENT DOCUMENTS

| | | |
|---|---|---|
| 2006/0135962 A1 | 6/2006 | Kick et al. |
| 2006/0135971 A1 | 6/2006 | Swanstrom et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149129 A1 | 7/2006 | Watts et al. |
| 2006/0149131 A1 | 7/2006 | Or |
| 2006/0149132 A1 | 7/2006 | Iddan |
| 2006/0161190 A1 | 7/2006 | Gadberry et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0217665 A1 | 9/2006 | Prosek |
| 2006/0217742 A1 | 9/2006 | Messerly et al. |
| 2006/0237023 A1 | 10/2006 | Cox et al. |
| 2006/0241570 A1 | 10/2006 | Wilk |
| 2006/0241691 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0253004 A1 | 11/2006 | Frisch et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0287644 A1 | 12/2006 | Inganas et al. |
| 2006/0287666 A1 | 12/2006 | Saadat et al. |
| 2007/0000550 A1 | 1/2007 | Osinski |
| 2007/0005019 A1 | 1/2007 | Okishige |
| 2007/0015965 A1 | 1/2007 | Cox et al. |
| 2007/0032701 A1 | 2/2007 | Fowler et al. |
| 2007/0051375 A1 | 3/2007 | Milliman |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0078439 A1 | 4/2007 | Grandt et al. |
| 2007/0083192 A1 | 4/2007 | Welch |
| 2007/0100375 A1 | 5/2007 | Mikkaichi et al. |
| 2007/0100376 A1 | 5/2007 | Mikkaichi et al. |
| 2007/0106113 A1 | 5/2007 | Ravo |
| 2007/0106317 A1 | 5/2007 | Shelton et al. |
| 2007/0112251 A1 | 5/2007 | Nakhuda |
| 2007/0112342 A1 | 5/2007 | Pearson et al. |
| 2007/0112385 A1 | 5/2007 | Conlon |
| 2007/0112417 A1 | 5/2007 | Shanley et al. |
| 2007/0118115 A1 | 5/2007 | Artale et al. |
| 2007/0123840 A1 | 5/2007 | Cox |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142779 A1 | 6/2007 | Duane et al. |
| 2007/0156028 A1 | 7/2007 | Van Lue et al. |
| 2007/0161855 A1 | 7/2007 | Mikkaichi et al. |
| 2007/0167901 A1 | 7/2007 | Herrig et al. |
| 2007/0173686 A1 | 7/2007 | Lin et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0191904 A1 | 8/2007 | Libbus et al. |
| 2007/0198057 A1 | 8/2007 | Gelbart et al. |
| 2007/0203398 A1 | 8/2007 | Bonadio et al. |
| 2007/0208336 A1 | 9/2007 | Kim et al. |
| 2007/0208407 A1 | 9/2007 | Gerdts et al. |
| 2007/0213754 A1 | 9/2007 | Mikkaichi et al. |
| 2007/0225552 A1 | 9/2007 | Segawa et al. |
| 2007/0233040 A1 | 10/2007 | Macnamara et al. |
| 2007/0244356 A1 | 10/2007 | Carrillo et al. |
| 2007/0244358 A1 | 10/2007 | Lee |
| 2007/0255303 A1 | 11/2007 | Bakos et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0265494 A1 | 11/2007 | Leanna et al. |
| 2007/0270629 A1 | 11/2007 | Charles |
| 2007/0270907 A1 | 11/2007 | Stokes et al. |
| 2007/0282165 A1 | 12/2007 | Hopkins et al. |
| 2008/0004650 A1 | 1/2008 | George |
| 2008/0015413 A1 | 1/2008 | Barlow et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033244 A1 | 2/2008 | Matsui et al. |
| 2008/0058586 A1 | 3/2008 | Karpiel |
| 2008/0065169 A1 | 3/2008 | Colliou et al. |
| 2008/0082108 A1 | 4/2008 | Skakoon et al. |
| 2008/0091068 A1 | 4/2008 | Terliuc |
| 2008/0097159 A1 | 4/2008 | Ishiguro |
| 2008/0097472 A1 | 4/2008 | Agmon et al. |
| 2008/0103527 A1 | 5/2008 | Martin et al. |
| 2008/0114384 A1 | 5/2008 | Chang et al. |
| 2008/0125765 A1 | 5/2008 | Berenshteyn et al. |
| 2008/0125774 A1 | 5/2008 | Palanker et al. |
| 2008/0125796 A1 | 5/2008 | Graham |
| 2008/0140069 A1 | 6/2008 | Filloux et al. |
| 2008/0140071 A1 | 6/2008 | Vegesna |
| 2008/0147056 A1 | 6/2008 | van der Weide et al. |
| 2008/0150754 A1 | 6/2008 | Quendt |
| 2008/0171907 A1 | 7/2008 | Long et al. |
| 2008/0188710 A1 | 8/2008 | Segawa et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0214890 A1 | 9/2008 | Motai et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0243148 A1 | 10/2008 | Mikkaichi et al. |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0275474 A1 | 11/2008 | Martin et al. |
| 2008/0287801 A1 | 11/2008 | Magnin et al. |
| 2008/0300461 A1 | 12/2008 | Shaw et al. |
| 2008/0300571 A1 | 12/2008 | LePivert |
| 2008/0306493 A1 | 12/2008 | Shibata et al. |
| 2008/0309758 A1 | 12/2008 | Karasawa et al. |
| 2009/0030278 A1 | 1/2009 | Minakuchi |
| 2009/0054728 A1 | 2/2009 | Trusty |
| 2009/0062788 A1 | 3/2009 | Long et al. |
| 2009/0062795 A1 | 3/2009 | Vakharia et al. |
| 2009/0078736 A1 | 3/2009 | Van Lue |
| 2009/0082627 A1 | 3/2009 | Karasawa et al. |
| 2009/0093690 A1 | 4/2009 | Yoshizawa |
| 2009/0112059 A1 | 4/2009 | Nobis |
| 2009/0112063 A1 | 4/2009 | Bakos et al. |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0163770 A1 | 6/2009 | Torrie et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198212 A1 | 8/2009 | Timberlake et al. |
| 2009/0198231 A1 | 8/2009 | Esser et al. |
| 2009/0210000 A1 | 8/2009 | Sullivan et al. |
| 2009/0221873 A1 | 9/2009 | McGrath |

(56) References Cited

U.S. PATENT DOCUMENTS

| | | |
|---|---|---|
| 2009/0228001 A1 | 9/2009 | Pacey |
| 2009/0259105 A1 | 10/2009 | Miyano et al. |
| 2009/0281559 A1 | 11/2009 | Swain et al. |
| 2009/0287236 A1 | 11/2009 | Bakos et al. |
| 2009/0292167 A1 | 11/2009 | Kimoto |
| 2009/0306470 A1 | 12/2009 | Karasawa et al. |
| 2009/0322864 A1 | 12/2009 | Karasawa et al. |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0023032 A1 | 1/2010 | Granja Filho |
| 2010/0036198 A1 | 2/2010 | Tacchino et al. |
| 2010/0048990 A1 | 2/2010 | Bakos |
| 2010/0049223 A1 | 2/2010 | Granja Filho |
| 2010/0056862 A1 | 3/2010 | Bakos |
| 2010/0076451 A1 | 3/2010 | Zwolinski et al. |
| 2010/0081875 A1* | 4/2010 | Fowler ............ A61B 1/00149 600/114 |
| 2010/0087705 A1* | 4/2010 | Byers ............ A61B 1/00128 600/104 |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrial et al. |
| 2010/0152725 A1 | 6/2010 | Pearson et al. |
| 2010/0160906 A1 | 6/2010 | Jarrard |
| 2010/0191050 A1 | 7/2010 | Zwolinski |
| 2010/0191267 A1 | 7/2010 | Fox |
| 2010/0198248 A1 | 8/2010 | Vakharia |
| 2010/0210906 A1 | 8/2010 | Wendlandt |
| 2010/0217367 A1 | 8/2010 | Belson |
| 2010/0249700 A1 | 9/2010 | Spivey |
| 2010/0268025 A1 | 10/2010 | Belson |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2011/0077476 A1 | 3/2011 | Rofougaran et al. |
| 2011/0087224 A1 | 4/2011 | Cadeddu et al. |
| 2011/0093009 A1 | 4/2011 | Fox |
| 2011/0098694 A1 | 4/2011 | Long |
| 2011/0098704 A1 | 4/2011 | Long et al. |
| 2011/0112434 A1 | 5/2011 | Ghabrial et al. |
| 2011/0112527 A1 | 5/2011 | Hamilton, Jr. et al. |
| 2011/0115891 A1 | 5/2011 | Trusty |
| 2011/0152610 A1 | 6/2011 | Trusty et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190764 A1 | 8/2011 | Long et al. |
| 2011/0245619 A1 | 10/2011 | Holcomb |
| 2011/0284014 A1 | 11/2011 | Cadeddu et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0101331 A1 | 4/2012 | Gilad et al. |
| 2012/0101413 A1 | 4/2012 | Beetel et al. |
| 2012/0109122 A1 | 5/2012 | Arena et al. |
| 2012/0116155 A1 | 5/2012 | Trusty |
| 2012/0116266 A1 | 5/2012 | Houser et al. |
| 2012/0149981 A1 | 6/2012 | Khait et al. |
| 2012/0191075 A1 | 7/2012 | Trusty |
| 2012/0191076 A1 | 7/2012 | Voegele et al. |
| 2012/0197246 A1 | 8/2012 | Mauch |
| 2013/0030430 A1 | 1/2013 | Stewart et al. |
| 2013/0090666 A1 | 4/2013 | Hess et al. |
| 2013/0158348 A1 | 6/2013 | Nobis et al. |
| 2013/0245356 A1 | 9/2013 | Fernandez et al. |
| 2013/0267834 A1 | 10/2013 | McGee |
| 2013/0331649 A1 | 12/2013 | Khait et al. |
| 2014/0039491 A1 | 2/2014 | Bakos et al. |
| 2014/0052216 A1 | 2/2014 | Long et al. |
| 2014/0121678 A1 | 5/2014 | Trusty et al. |
| 2014/0243597 A1 | 8/2014 | Weisenburgh, II et al. |
| 2015/0032132 A1 | 1/2015 | Harris et al. |
| 2015/0100064 A1 | 4/2015 | Skakoon et al. |
| 2015/0230858 A1 | 8/2015 | Long et al. |
| 2016/0074056 A1 | 3/2016 | Conlon |
| 2016/0100879 A1 | 4/2016 | Long |
| 2016/0128759 A1 | 5/2016 | Long et al. |
| 2016/0296280 A1 | 10/2016 | Long |
| 2017/0049508 A1 | 2/2017 | Long et al. |
| 2017/0086937 A1 | 3/2017 | Tellio et al. |
| 2017/0119465 A1 | 5/2017 | Long et al. |
| 2018/0042661 A1 | 2/2018 | Long et al. |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0499491 A2 | 8/1992 |
| EP | 0589454 A2 | 3/1994 |
| EP | 0464479 B1 | 3/1995 |
| EP | 0529675 B1 | 2/1996 |
| EP | 0773003 A1 | 5/1997 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 1477104 B1 | 1/2009 |
| EP | 0723462 B1 | 3/2009 |
| EP | 1769749 B1 | 11/2009 |
| EP | 2135545 A2 | 12/2009 |
| EP | 1769766 B1 | 2/2010 |
| EP | 1493397 B1 | 9/2011 |
| EP | 2659847 A1 | 11/2013 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | S63309252 A | 12/1988 |

(56) References Cited

FOREIGN PATENT DOCUMENTS

| | | | |
|---|---|---|---|
| JP | H0438960 A | 2/1992 |
| JP | H06269460 A | 9/1994 |
| JP | H0829699 A | 2/1996 |
| JP | H0975365 A | 3/1997 |
| JP | H1024049 A | 1/1998 |
| JP | 3007713 B2 | 2/2000 |
| JP | 2000107197 A | 4/2000 |
| JP | 2000245683 A | 9/2000 |
| JP | 2001526072 A | 12/2001 |
| JP | 2002369791 A | 12/2002 |
| JP | 2003088494 A | 3/2003 |
| JP | 2003235852 A | 8/2003 |
| JP | 2004033525 A | 2/2004 |
| JP | 2004065745 A | 3/2004 |
| JP | 2005121947 A | 5/2005 |
| JP | 2005261514 A | 9/2005 |
| JP | 2005296063 A | 10/2005 |
| JP | 2006517843 A | 8/2006 |
| JP | 2006297005 A | 11/2006 |
| JP | 2006343510 A | 12/2006 |
| JP | 2007020806 A | 2/2007 |
| JP | 2007125264 A | 5/2007 |
| JP | 2007516792 A | 6/2007 |
| JP | 2010503496 A | 2/2010 |
| JP | 2012515018 A | 7/2012 |
| JP | 5646674 B2 | 12/2014 |
| NL | 1021295 C2 | 2/2004 |
| SU | 194230 | 5/1967 |
| SU | 980703 A1 | 12/1982 |
| WO | WO-8401707 A1 | 5/1984 |
| WO | WO-8607543 A1 | 12/1986 |
| WO | WO-9213494 A1 | 8/1992 |
| WO | WO-9310850 A1 | 6/1993 |
| WO | WO-9320760 A1 | 10/1993 |
| WO | WO-9320765 A1 | 10/1993 |
| WO | WO-9422383 A1 | 10/1994 |
| WO | WO-9509666 A1 | 4/1995 |
| WO | WO-9622056 A1 | 7/1996 |
| WO | WO-9627331 A1 | 9/1996 |
| WO | WO-9639946 A1 | 12/1996 |
| WO | WO-9712557 A1 | 4/1997 |
| WO | WO-9801080 A1 | 1/1998 |
| WO | WO-9900060 A1 | 1/1999 |
| WO | WO-9909919 A1 | 3/1999 |
| WO | WO-9917661 A1 | 4/1999 |
| WO | WO-9930622 A2 | 6/1999 |
| WO | WO-0022996 A1 | 4/2000 |
| WO | WO-0035358 A1 | 6/2000 |
| WO | WO-0068665 A1 | 11/2000 |
| WO | WO-0110319 A1 | 2/2001 |
| WO | WO-0126708 A1 | 4/2001 |
| WO | WO-0141627 A2 | 6/2001 |
| WO | WO-0158360 A2 | 8/2001 |
| WO | WO-0211621 A2 | 2/2002 |
| WO | WO-0234122 A2 | 5/2002 |
| WO | WO-02094082 A2 | 11/2002 |
| WO | WO-03045260 A1 | 6/2003 |
| WO | WO-03047684 A2 | 6/2003 |
| WO | WO-03059412 A1 | 7/2003 |
| WO | WO-03078721 A2 | 9/2003 |
| WO | WO-03081761 A2 | 10/2003 |
| WO | WO-03082129 A2 | 10/2003 |
| WO | WO-2004006789 A1 | 1/2004 |
| WO | WO-2004028613 A2 | 4/2004 |
| WO | WO-2004037123 A1 | 5/2004 |
| WO | WO-2004037149 A1 | 5/2004 |
| WO | WO-2004052221 A1 | 6/2004 |
| WO | WO-2004086984 A1 | 10/2004 |
| WO | WO-2005009211 A2 | 2/2005 |
| WO | WO-2005018467 A2 | 3/2005 |
| WO | WO-2005037088 A2 | 4/2005 |
| WO | WO-2005048827 A1 | 6/2005 |
| WO | WO-2005065284 A2 | 7/2005 |
| WO | WO-2005097019 A2 | 10/2005 |
| WO | WO-2005097234 A2 | 10/2005 |
| WO | WO-2005112810 A2 | 12/2005 |
| WO | WO-2005120363 A1 | 12/2005 |
| WO | WO-2005122866 A1 | 12/2005 |
| WO | WO-2006007399 A1 | 1/2006 |
| WO | WO-2006012630 A2 | 2/2006 |
| WO | WO-2006040109 A1 | 4/2006 |
| WO | WO-2006041881 A2 | 4/2006 |
| WO | WO-2006060405 A2 | 6/2006 |
| WO | WO-2006110733 A2 | 10/2006 |
| WO | WO-2006113216 A2 | 10/2006 |
| WO | WO-2007013059 A2 | 2/2007 |
| WO | WO-2007014063 A2 | 2/2007 |
| WO | WO-2007035537 A2 | 3/2007 |
| WO | WO-2007048085 A2 | 4/2007 |
| WO | WO-2007063550 A2 | 6/2007 |
| WO | WO-2007100067 A1 | 9/2007 |
| WO | WO-2007109171 A2 | 9/2007 |
| WO | WO-2007135577 A2 | 11/2007 |
| WO | WO-2007143200 A2 | 12/2007 |
| WO | WO-2007144004 A1 | 12/2007 |
| WO | WO-2008005433 A1 | 1/2008 |
| WO | WO-2008033356 A2 | 3/2008 |
| WO | WO-2008034103 A2 | 3/2008 |
| WO | WO-2008041225 A2 | 4/2008 |
| WO | WO-2008076337 A1 | 6/2008 |
| WO | WO-2008076800 A2 | 6/2008 |
| WO | WO-2008079440 A2 | 7/2008 |
| WO | WO-2008080062 A2 | 7/2008 |
| WO | WO-2008101075 A2 | 8/2008 |
| WO | WO-2008101086 A2 | 8/2008 |
| WO | WO-2008102154 A2 | 8/2008 |
| WO | WO-2008108863 A2 | 9/2008 |
| WO | WO-2008151237 A1 | 12/2008 |
| WO | WO-2009021030 A2 | 2/2009 |
| WO | WO-2009027065 A1 | 3/2009 |
| WO | WO-2009029065 A1 | 3/2009 |
| WO | WO-2009032623 A2 | 3/2009 |
| WO | WO-2009036457 A1 | 3/2009 |
| WO | WO-2009121017 A1 | 10/2009 |
| WO | WO-2009132190 A2 | 10/2009 |
| WO | WO-2010027688 A1 | 3/2010 |
| WO | WO-2010056716 A2 | 5/2010 |
| WO | WO-2010080974 A1 | 7/2010 |
| WO | WO-2010088481 A1 | 8/2010 |
| WO | WO-2012031204 A2 | 3/2012 |
| WO | WO-2012068505 A1 | 5/2012 |
| WO | WO-2012071526 A2 | 5/2012 |
| WO | WO-2013044378 A1 | 4/2013 |

OTHER PUBLICATIONS

"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

B. Rubinsky, Ph.D., "Irreversible Electroporation in Medicine," Technology in Cancer Research and Treatment, vol. 6, No. 4, Aug. 2007, pp. 255-259.

Bewlay et al., "Spinning" in ASM Handbook, vol. 14B, Metalworking: Sheet Forming (2006).

C. Cope et al., "Long Term Patency of Experimental Magnetic Compression Gastroenteric Anastomoses Achieved with Covered Stents," Gastrointest Endosc, (2001), vol. 53, pp. 780-784.

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

Castellvi et al., "Hybrid Transvaginal NOTES Sleeve Gastrectomy in a Porcine Model Using a Magnetically Anchored Camera and

(56) References Cited

OTHER PUBLICATIONS

Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
CRE™ Pulmonary Balloon Dilator; [online] URL: http://www.bostonscientific.com/Device.bsci?page=HCP_Overview&navRe1Id=1000.1003&method=D . . . , accessed Jul. 18, 2008 (4 pages).
D. Wilhelm et al., "An Innovative, Safe and Sterile Sigmoid Access (ISSA) for NOTES," Endoscopy 2007, vol. 39, pp. 401-406.
D.B. Nelson, MD et al., "Endoscopic Hemostatic Devices," Gastrointestinal Endoscopy, vol. 54, No. 6, 2001, pp. 833-840.
D.G. Fong et al., "Transcolonic Ventral Wall Hernia Mesh Fixation in a Porcine Model," Endoscopy 2007; 39: 865-869.
Davalos, et al., "Tissue Ablation with Irreversible Electroporation," Annals of Biomedical Engineering, 33.2 (2005): 223-231.
Edd, et al., "In Vivo Results of a New Focal Tissue Ablation Technique: Irreversible Electroporation," IEEE Trans Biomed Eng, vol. 53, pp. 1409-1415, 2006.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
Ethicon, Inc., "Wound Closure Manual: Chapter 3 (The Surgical Needle)," 15 pages, (1994).
Evans, "Ablative and cathether-delivered therapies for colorectal liver metastases (CRLM)," EJSO, 33, pp. S64-S75 (2007).
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Fevrier 1826. Recueil De La Societe Royale De Medecin De Marseille. Marseille: lmpr. D'Achard, 1826; 1:127-31. (with English translation).
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
G.A. Hallenbeck, M.D. et al., "An Instrument for Colorectal Anastomosis Without Sutrues," Dis Col Rectum, (1963), vol. 5, pp. 98-101.
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Guyton et al., "Contraction of Skeletal Muscle," Textbook of Medical Physiology, pp. 82-84 (2000).
Guyton et al., "Membrane Potentials and Action Potentials," W.B. Sanders, ed. Textbook of Medical Physiology, p. 56 (2000).
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
H. Seifert, et al., "Retroperitoneal Endoscopic Debridement for Infected Peripancreatic Necrosis," The Lancet, Research Letters, vol. 356, Aug. 19, 2000, pp. 653-655.
Hakko Retractors, obtained Aug. 25, 2009 (5 pages).
Heller et al., "Electrically mediated plasmid DNA delivery to hepatocellular carcinomas in vivo," Gene Therapy, 7, pp. 826-829 (2000).
How Stuff Works "How Smart Structures Will Work," http://science.howstuffworks.com/engineering/structural/smart-structure1.htm; accessed online Nov. 1, 2011 (3 pages).
I. Fraser, "An Historical Perspective on Mechanical Aids in Intestinal Anastamosis," Surg. Gynecol. Obstet. (Oct. 1982), vol. 155, pp. 566-74.

Instant Armor: Science Videos—Science News—ScienCentral; http://www.sciencentral.com/articles./view.php3?article_id=218392121; accessed online Nov. 1, 2011 (2 pages).
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
J.D. Paulson, M.D., et al., "Development of Flexible Culdoscopy," The Journal of the American Association of Gynecologic Laparoscopists, Nov. 1999, vol. 6, No. 4, pp. 487-490.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
Jolly et al., Properties and Applications of Commercial Magneto rheological Fluids. SPIE 5th Annual Int. Symposium on Smart Structures and Materials, 1998 (18 pages).
K. Sumiyama et al., "Endoscopic Caps," Tech. Gastrointest. Endosc., vol. 8, pp. 28-32, 2006.
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
Kennedy, et al., "High-Burst-Strength, Feedback-Controlled Bipolar Vessel Sealing," Surgical Endoscopy, vol. 12, pp. 876-878 (1998).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
Maxim Integrated Application Note 3977: Class D Amplifiers: Fundamentals of Operation and Recent Developments, Jan. 31, 2007.
Michael S. Kavic, M.D., "Natural Orifice Translumenal Endoscopic Surgery: "NOTES"", JSLS, vol. 10, pp. 133-134 (2006).
Miklavcic et al., "A validated model of in vivo electric field distribution in tissues for electrochemotherapy and for DNA electrotransfer for gene therapy," Biochimica et Biophysica Acta, 1523, pp. 73-83 (2000).
Mulier et al., "Radiofrequency Ablation Versus Resection for Resectable Colorectal Liver Metastases: Time for a Randomized Trial?" Annals of Surgical Oncology, 15(1), pp. 144-157 (2008).
N. Chopita et al., "Endoscopic Gastroenteric Anastamosis Using Magnets," Endoscopy, (2005), vol. 37(4), pp. 313-317.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Ogando, "Prototype Tools That Go With the Flow," Design News, 2 pages, Jul. 17, 2006.
P. O'Neill, M.D. et al., "Nonsuture Intestinal Anastomosis," Am J. Surg, (1962), vol. 104, pp. 761-767.
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Rutala et al. "Guideline for Disinfection and Sterilization in Healthcare Facilities, 2008" (available at http://www.cdc.gov/hicpac/Disinfection_Sterilization/13_11sterilizingPractices.html).

(56) References Cited

OTHER PUBLICATIONS

Schoenbach et al. "Bacterial Decontamination of Liquids with Pulsed Electric Fields" IEEE Transactions on Dielectrics and Electrical Insulation. vol. 7 No. 5. Oct. 2000, pp. 637-645.

Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).

T. Hardy, Jr., M.D. et al., "A Biofragmentable Ring for Sutureless Bowel Anastomosis. An Experimental Study," Dis Col Rectum, (1985), vol. 28, pp. 484-490.

USGI® EndoSurgical Operating System—g-Prox® Tissue Grasper/Approximation Device; [online] URL: http://www.usgimedical.com/eos/components-gprox.htm—accessed May 30, 2008 (2 pages).

Weaver et al., "Theory of electroporation: A review," Bioelectrochemistry and Bioenergetics, 41, pp. 135-160 (1996).

Widera et al., "Increased DNA Vaccine Delivery and Immunogenicity by Electroporation In Vivo," The Journal of Immunology, 164, pp. 4635-4640 (2000).

Wong et al., "Combined Percutaneous Radiofrequency Ablation and Ethanol Injection for Hepatocellular Carcinoma in High-Risk Locations," AJR, 190, pp. W187-W195 (2008).

Z-Offset Technique Used in the Introduction of Trocar During Laparoscopic Surgery, M.S. Hershey NOTES Presentation to EES NOTES Development Team, Sep. 27, 2007.

Zadno et al., "Linear Superelasticity in Cold-Worked NI-TI," Engineering Aspects of Shape Memory Alloys, pp. 414-419 (1990).

\* cited by examiner

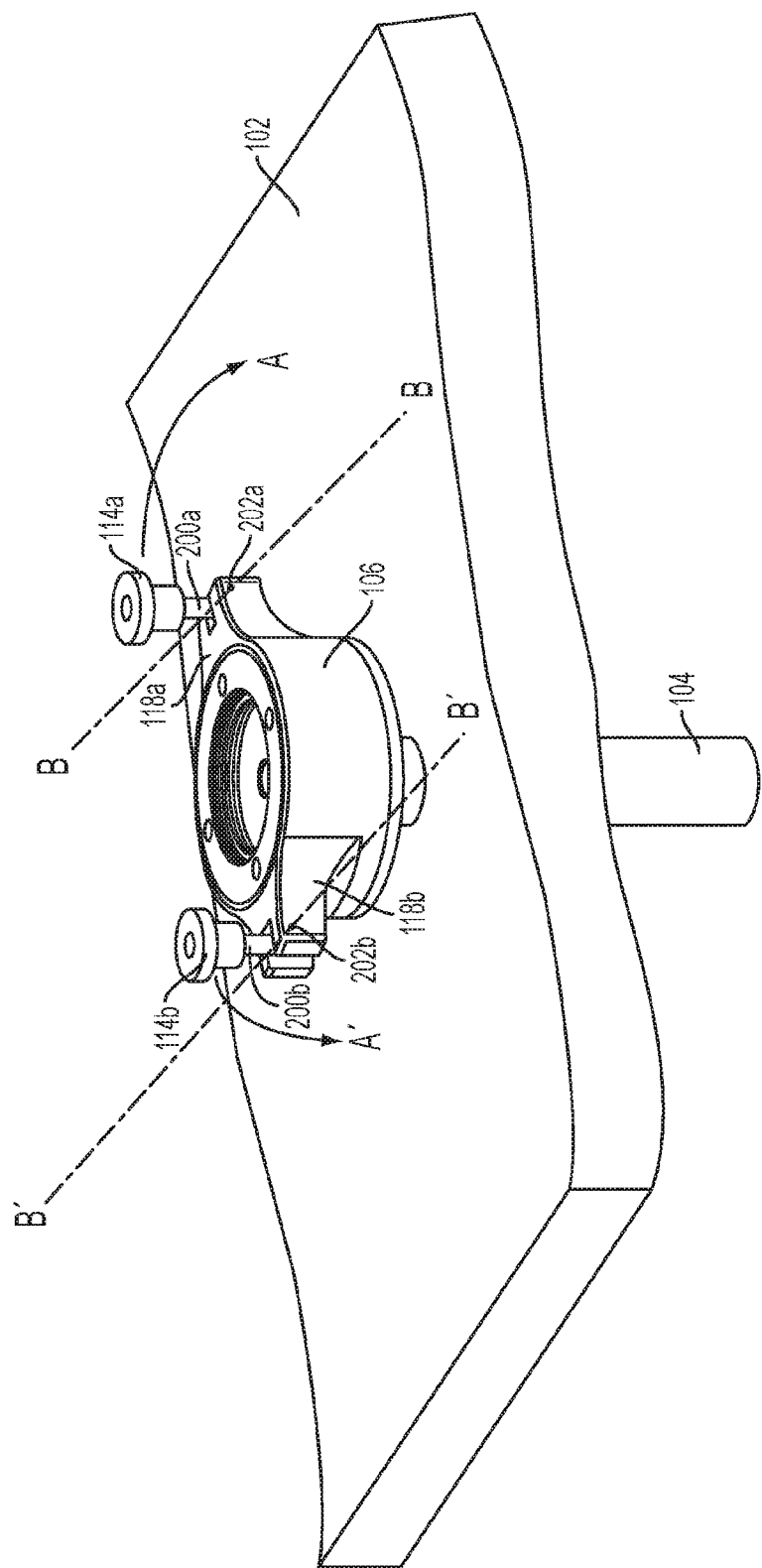

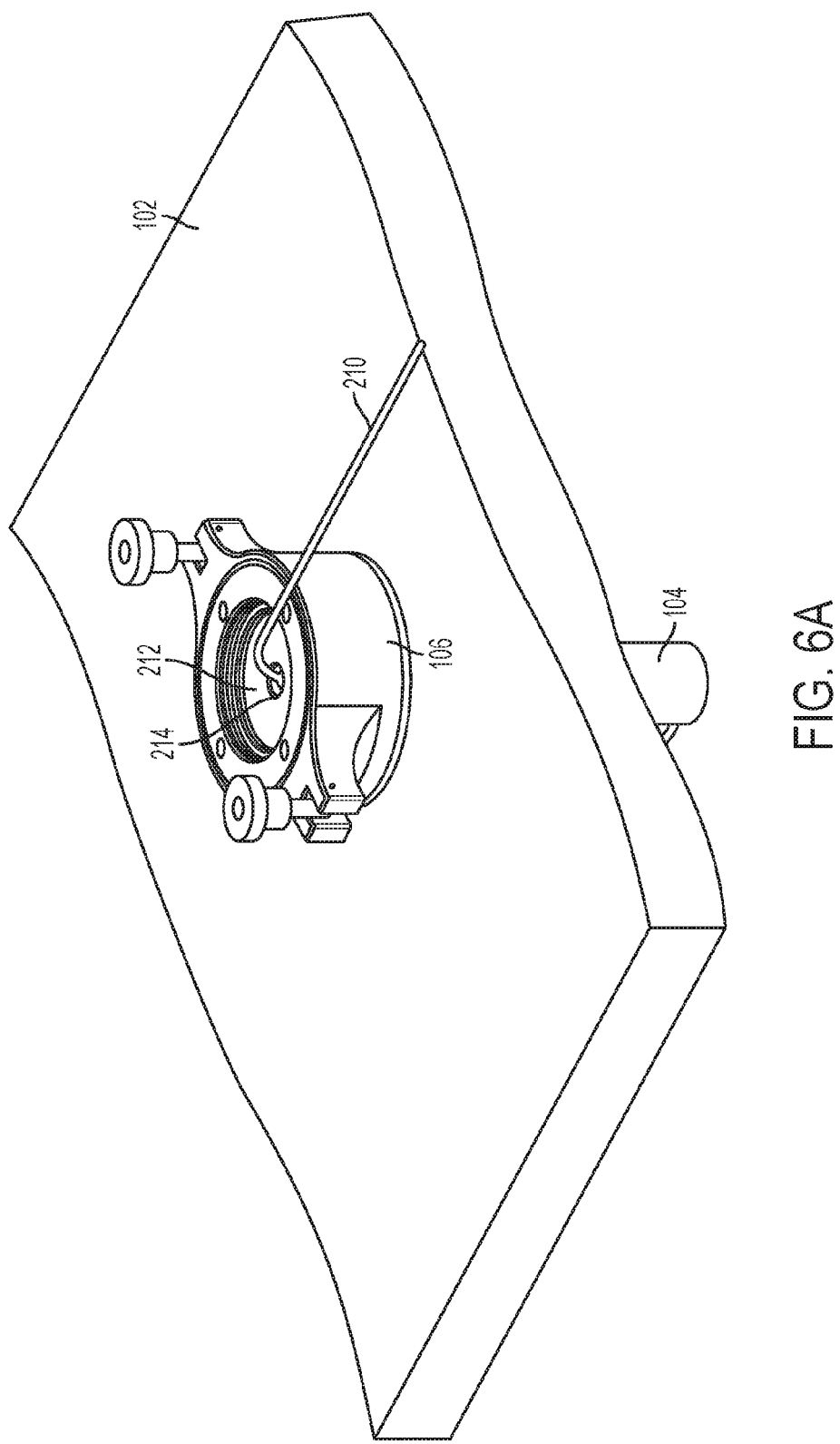

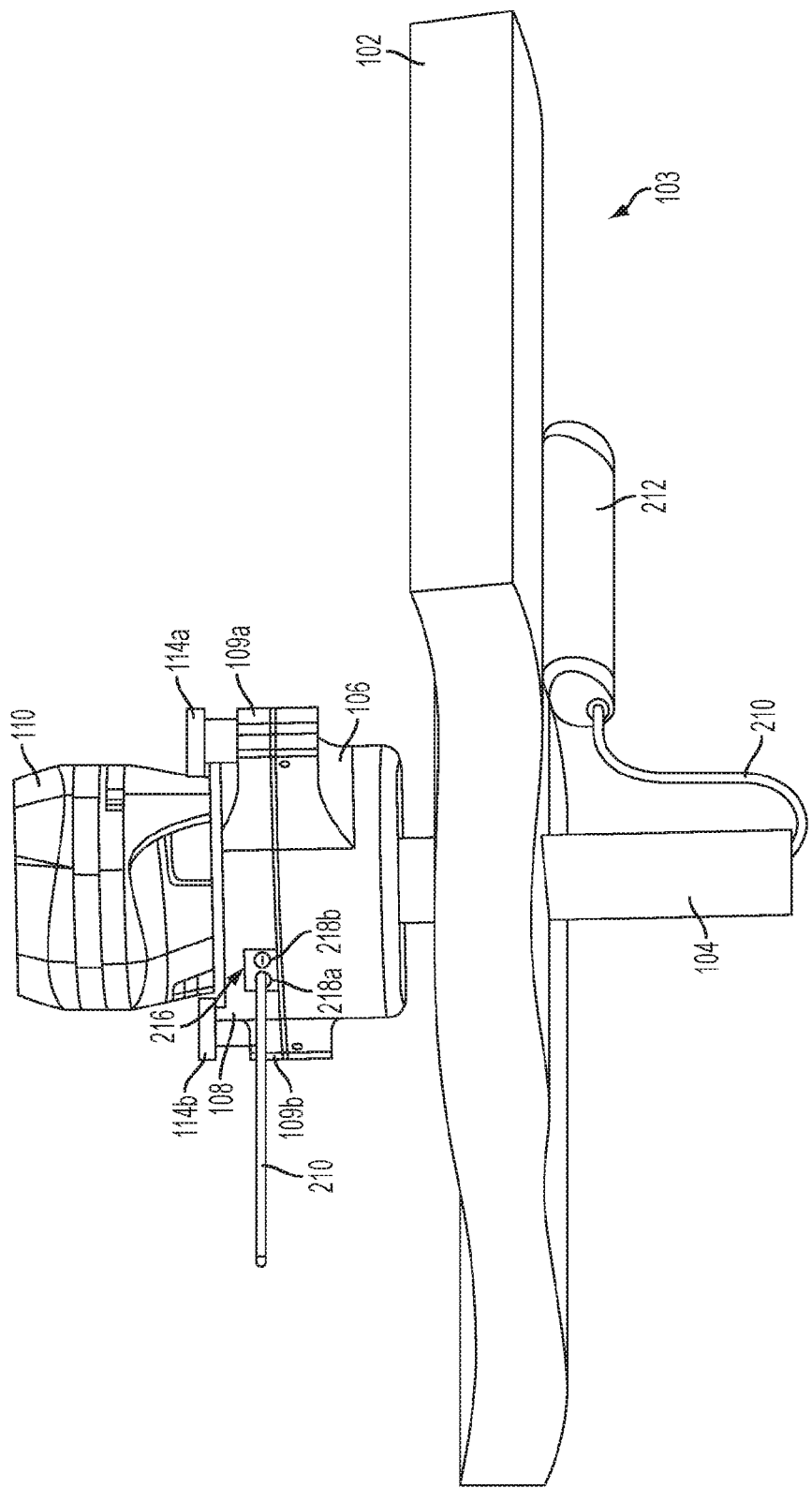

APPARATUS FOR INTRODUCING AN OBJECT INTO A PATIENT

CROSS-REFERENCE TO RELATED APPLICATIONS

This application is a divisional application claiming priority under 35 U.S.C. § 121 to U.S. patent application Ser. No. 13/470,781, filed May 14, 2012, entitled "APPARATUS FOR INTRODUCING A STEERABLE CAMERA ASSEMBLY INTO A PATIENT," which issued on Aug. 30, 2016 as U.S. Pat. No. 9,427,255, the entire disclosure of which is hereby incorporated by reference herein.

BACKGROUND

Endoscopic surgery in the abdominal cavity of an animal, such as, for example, a human, may include insufflating the abdomen to create a space in which surgeons may introduce endoscopic surgical instruments. Access to the abdomen may be created with a trocar assembly, which may include a hollow cannula and a solid shaft passing through the cannula. The solid shaft may include a sharp tip that pierces the abdominal wall to form an otomy and that guides the cannula partially into the insufflated abdominal cavity. After the cannula is in place in the otomy, the solid shaft may be withdrawn from the cannula, leaving a passage through the cannula that the surgeon may use to access the abdominal cavity using endoscopic surgical devices. The cannula may include a seal, such as a duck bill seal, at its distal end that is biased in a closed position to prevent or retard the escape of gases insufflating the abdomen. A surgeon chooses a trocar size that closely fits the endoscopic tools he intends to introduce therethrough. For example, if the endoscopic tool to be used has a diameter of 14 millimeters, then a cannula having an inner diameter of slightly more than 14 millimeters would be used. The endoscopic tool passes through the cannula and opens the seal on the cannula. The close sizing between the endoscopic tool and the cannula prevents or retards the escape of the gasses insufflating the abdomen that would otherwise pass through the open seal.

Magnetic anchoring and guidance systems (MAGS) have been developed for use in minimally invasive procedures. MAGS include an internal device attached in some manner to a surgical instrument, laparoscope or other camera or viewing device, and an external hand held device or external control unit ("ECU") for controlling the movement of the internal device. Each of the external and internal devices has magnets which are magnetically coupled to each other across, for example, a patient's abdominal wall. In the current systems, the external magnet may be adjusted by varying the height of the external magnet.

The camera is attached to one or more tethers that provide power to the camera's electronics, image date, and, optionally, water or gases. The tethers lead out through the cannula and pass through the seal on the cannula. The presence of the tether prevents the seal on currently-available cannulas from closing, thereby creating a leak that enables the insufflation gases to escape when other endoscopic surgical instruments are not placed in the cannula.

The foregoing discussion is intended only to illustrate various aspects of the related art in the field of the invention at the time, and should not be taken as a disavowal of claim scope.

SUMMARY OF THE INVENTION

Embodiments described herein provide a cannula assembly with a seal for a tether of an internal magnetic camera. The cannula assembly may include a housing that includes a distal opening and a proximal opening with a passage therebetween. The housing may be configured to have a cannula tube attached in a manner that the cannula tube is in fluid communication with the distal opening. A plurality of compliant membranes may be arranged as a stack anywhere in the passage or in the proximal or distal openings. The compliant membranes may be made of any compliant material, such as, for example, silicone, latex, or rubber. In various embodiments, the stack may include two compliant membranes. In various other embodiments, the stack may include three compliant membranes. Each membrane includes an aperture that may open to accommodate an internal magnetic camera or its tether, or any other endoscopic device that is passed through the membranes. The apertures may be arranged such that, when the compliant membranes are stacked, each aperture does not overlap with remaining apertures.

In certain embodiments in which the stack includes at least three compliant membranes, one of the apertures may comprise a slit, and the compliant membrane in which the slit is formed is sandwiched between two membranes having apertures of a different configuration, such as, for example, apertures having circular shapes. In certain other embodiments in which the stack includes at least three compliant membranes, each aperture may comprise a wedge-shaped gap formed in its respective compliant membrane, and, the compliant membranes may be arranged such that, when they are arranged in a stack, each wedge-shaped gap does not overlap with remaining wedge-shaped gaps.

In various embodiments, the membranes may include a plurality of engagement members that are configured to couple to engagement members in the passage or one of the proximal and distal openings of the cannula housing. In certain embodiments, coupling of the respective membranes may result in each of the compliant membranes being stretched in a region between its engagement members. In certain embodiments, the engagement members of the cannula housing may comprise a plurality of posts around a periphery of the passage or one of the proximal or distal openings, and the engagement members on each of the compliant membranes may comprise a plurality of holes around the periphery each membrane that fit over the posts. A retaining ring may be placed on the membranes to retain them in the passage or in the proximal or distal openings.

In various embodiments, the cannula housing may be configured include an upper housing in fluid communication with the proximal opening. The upper housing may include a port or several ports configured to receive tethers of the camera, and the ports are distinct from an opening in the upper housing that is configured to receive other endoscopic instruments. The ports may include gaskets that provide a tight seal against the tethers.

In various embodiments, the cannula housing may include a first face and a second face, and each of the first and second faces includes a proximate opening. Each of the two proximate openings has a plurality of compliant membranes and apertures. The two proximate openings are at an angle relative to each other, and each of the two openings is in fluid communication with the passage in the cannula housing. The housing is configured to rotate in a bracket between a first position and a second position. In the first position, a first of the two proximate openings is aligned with the distal opening via the passage. In the second position, a second of the proximate openings is aligned with the distal opening via the passage.

In various embodiments, a cannula assembly includes a cannula tube and the seal comprises a sleeve encasing at least a portion of the tube. The sleeve may include a seal at its distal end, such as, for example, a duck bill seal or a clam shell seal. The sleeve also may include a channel on its periphery and substantially parallel to a longitudinal axis of the cannula tube. The channel is configured to receive a tether for an internal magnetic camera. The channel may include open distal and proximal ends such that the tether bypasses the seal. In use, after the surgeon inserts the cannula tube into a body cavity through an otomy, the cannula tube may be removed, leaving the sleeve positioned in the otomy. The seal at the distal end of the sleeve inhibits the escape of insufflation gases from the body cavity. The surgeon may then push the camera into the body cavity through the sleeve. After the camera is positioned in the body cavity, the camera tether may be pushed into the tether such that it is out of the way for additional endoscopic instruments that may be placed in the sleeve.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 5 is a perspective view of a cannula housing positioned in tissue according to an embodiment of the present invention;

FIG. 6A is a perspective view of a cannula housing according to an embodiment of the present invention with a tether disposed therethrough;

FIG. 7 is an embodiment of a cannula and trocar assembly according to an embodiment of the present invention showing a tether passing through a port on the cannula housing and an internally positioned camera;

FIG. 9I is a third perspective view of the cannula tube and housing of FIG. 9H with the tether passing therethrough, wherein the housing is moved to a rotated positioned;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION OF THE INVENTION

Figure 1A:
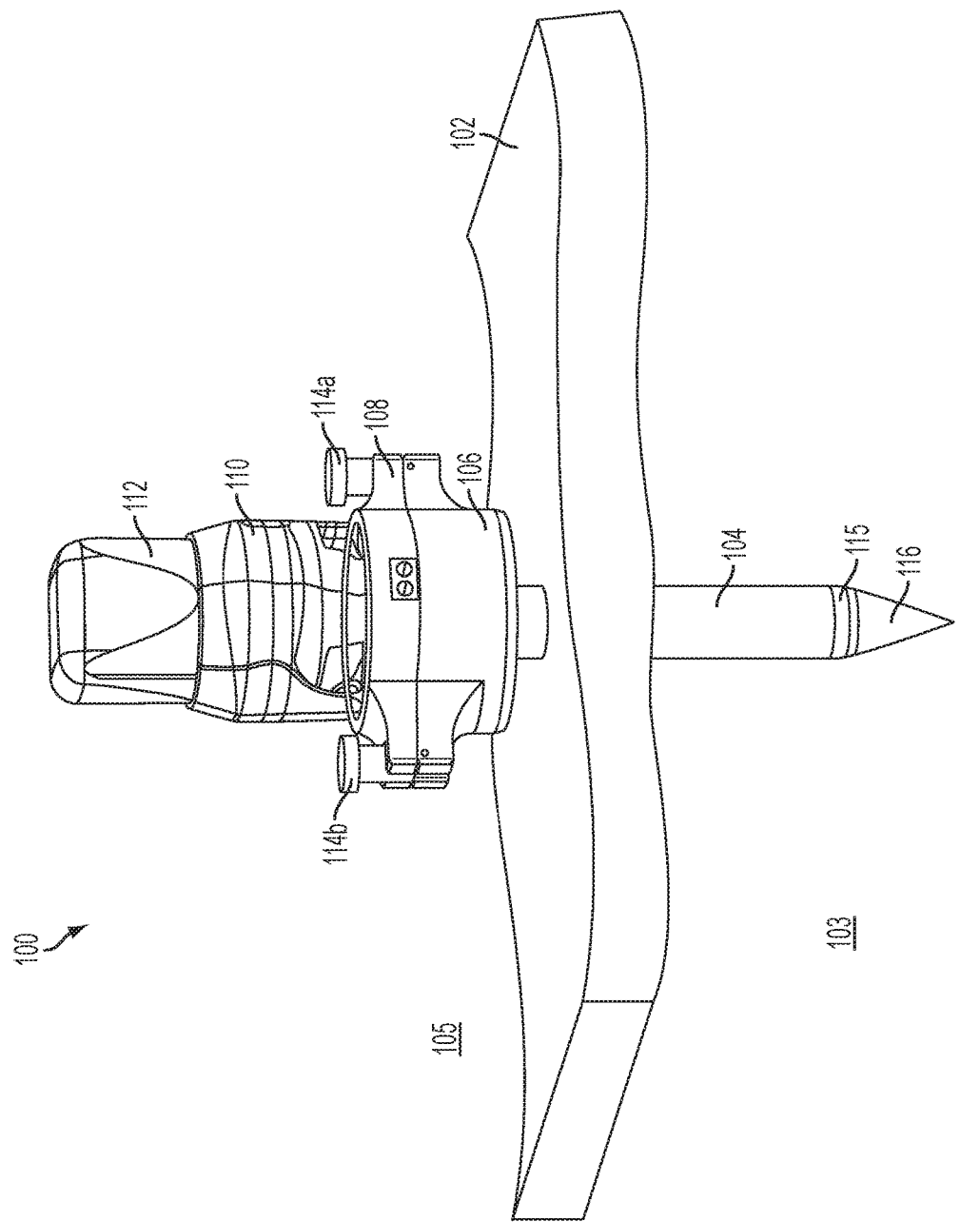
FIG. 1A is a perspective view of a trocar and obturator assembly according to an embodiment of the present invention.

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

In describing and claiming the present invention, the following terminology will be used in accordance with the definitions set out below.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located farthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

As used herein, the term "biocompatible" includes any material that is compatible with the living tissues and system(s) of a patient by not being substantially toxic or injurious and not known to cause immunological rejection. "Biocompatibility" includes the tendency of a material to be biocompatible.

As used herein, the term "patient" refers to any human or animal on which a suturing procedure may be performed. As used herein, the term "internal site" of a patient means a lumen, body cavity or other location in a patient's body including, without limitation, sites accessible through natural orifices or through incisions.

Figure 1B:
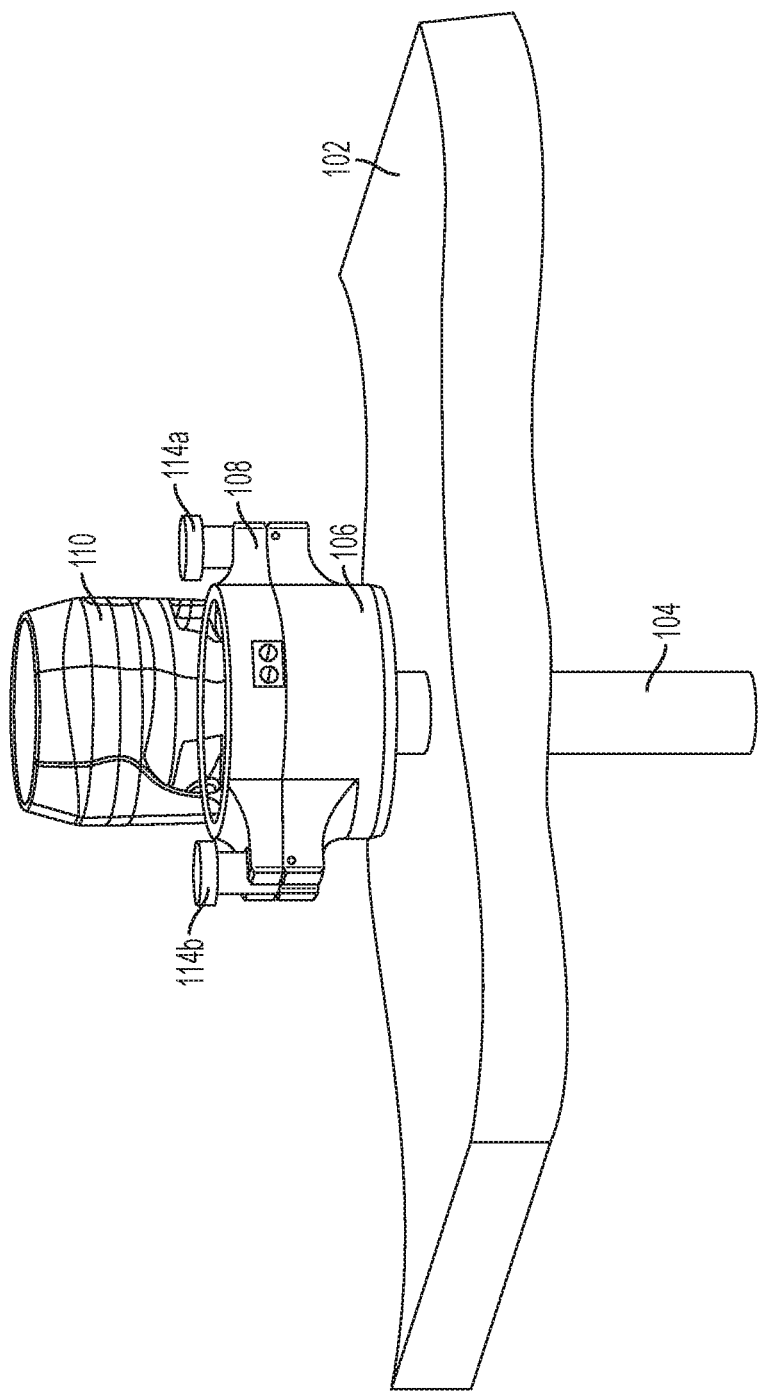
FIG. 1B is a perspective view of the trocar assembly of FIG. 1A with an obturator assembly removed.

FIG. 1A is a perspective view of a surgical trocar assembly 100, such as the trocar assembly described in U.S. Pat. No. 5,817,061, the relevant portions of which are incorporated by reference, modified to incorporate an embodiment of the present invention, passing through tissue 102 of an animal, such as, for example, a human. The surgical trocar assembly 100 includes a cannula tube 104 attached to a lower cannula housing 106. An upper cannula housing 108 is mounted on top of the lower cannula housing 106 and is held in place by thumb screws 114a and 114b. A cannula head 110 is attached to the top of the upper cannula housing 108. The cannula head 110 may be permanently attached to the upper cannula housing 108, for example, by glue, epoxy, or other bonding agents, or by welding, such as ultrasonic welding. Alternatively, the cannula head 110 may be removably attached to the upper cannula housing 108, for example, by screws, bolts, clips, or the like. The cannula tube 104 is hollow, and the lower cannula housing 106, upper cannula housing 108, and cannula head 110 each include an aperture aligned with the hollow cannula tube 104 such that an obturator shaft 115 may pass therethrough. The obturator shaft 115 may terminate at a distal end with an obturator tip 116. The obturator shaft 115 is attached at its proximal end to an obturator grip 112. The obturator grip 112 may be attachable to the cannula head 110, for example, by a spring-loaded clip (not shown), such that the trocar assembly 100 may be manipulated as a whole. In FIG. 1A, a substantial portion of the cannula tube 104, and the obturator shaft 115, and the obturator tip 116 have penetrated the tissue 102 and have passed into an interior body cavity 103, such as, for example, an abdominal cavity. The lower cannula housing 106, upper cannula housing 108, cannula head 110, and obturator grip 112 remain in an exterior space 105. When the trocar assembly 100 is positioned as shown in FIG. 1A, the obturator shaft 115 may be removed from the cannula tube 104. FIG. 1B is a perspective view of the surgical trocar subassembly 100 with the obturator shaft 115 and obturator grip 112 so removed.

Figure 2A:
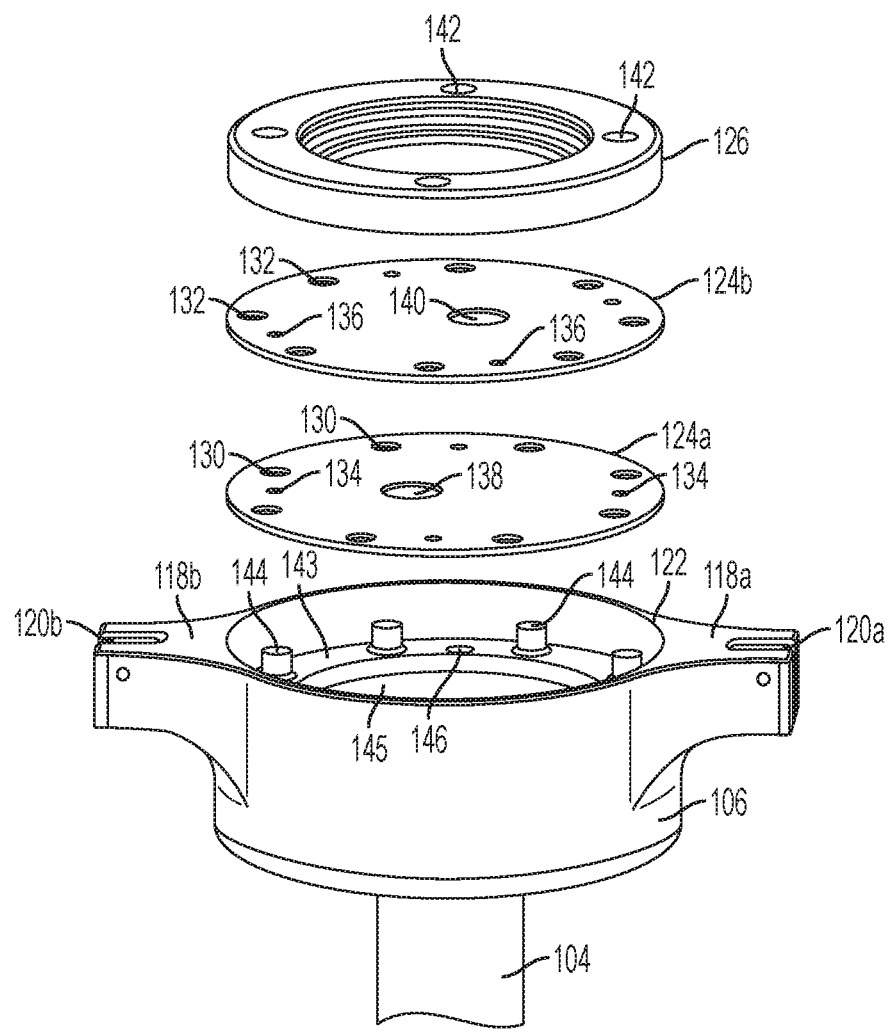
FIG. 2A is a perspective exploded view of a cannula housing and compliant membranes according to an embodiment of the present invention.

FIG. 2A is a perspective exploded view of the lower cannula housing 106 and sealing membranes 124a and 124b disposed therein. The lower cannula housing 106 may be hollow, including a proximal opening 122 that communicates with the upper cannula housing 108 (not shown in FIG. 2A) and a passage 145 that communicates with the hollow cannula tube 104. An engagement surface 143 in the passage 145 includes several engagement members, such as pins, clips, or anchors 144. For example, the engagement members 144 may be posts, such as, for example, cylindrical posts around the periphery of the engagement surface 143. A plurality of membranes 124a and 124b (in the embodiment shown in FIG. 2A, two membranes) may be placed in the passage and secured to the engagement surface 143. The membranes at least partially block fluid communication between the proximal opening 122 and the passage 145. Each membrane preferably may be made of a compliant material, such as, for example, silicone, latex, or rubber. Membrane 124a may include engagement members 130 on its periphery that compliment the engagement members 144 on the engagement surface. Membrane 124b may include engagement members 132 on its periphery that compliment the engagement members 144 on the engagement surface. For example, each of the engagement members 130, 132 may comprise a series of holes arranged on the periphery of respective membranes 124a and 124b. The engagement members 130, 132 on respective membranes 124a and 124b align with the engagement members 144 on the engagement surface 143, and placement of the engagement members 130, 132 over the anchors result in each membrane 124a and 124b being aligned in a fixed facing relationship relative to remaining membranes. Placement of the engagement members 130, 132 over the engagement members 144 also may result in the membranes 124a and 124b being stretched. A retaining ring 126 may be placed on top of the membranes 124a and 124b to hold the membranes 124a and 124b in place. The retaining ring 126 may include holes 142 sized to accommodate screws or other fasteners (not shown). The fasteners also may pass through holes 136 in membrane 124b and holes 134 in membrane 124a to anchor in holes 146 in the engagement surface 143. Membrane 124a includes an aperture 138 and membrane 124b includes an aperture 140. When the membranes 124a and 124b are installed in the lower cannula housing 106, the apertures 138 and 140 preferably are not aligned, i.e., the apertures 138 and 140 do not overlap. For example, the apertures 138, 140 may be disposed proximate to centers of the membranes 124a and 124b, but each membrane's aperture is offset from the membrane's center such that the aperture 138 of the first membrane 124a does not overlap with the aperture 140 of the second membrane 124b.

Figure 2B:
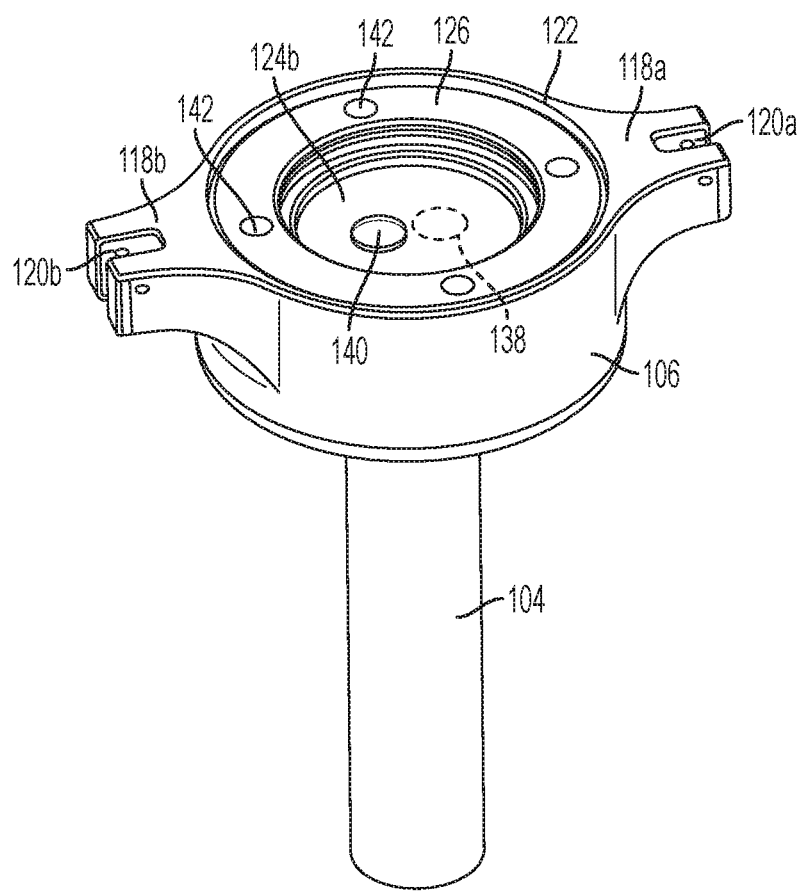
FIG. 2B is a perspective view of the cannula housing and compliant membranes of FIG. 2A.
Figure 2C:
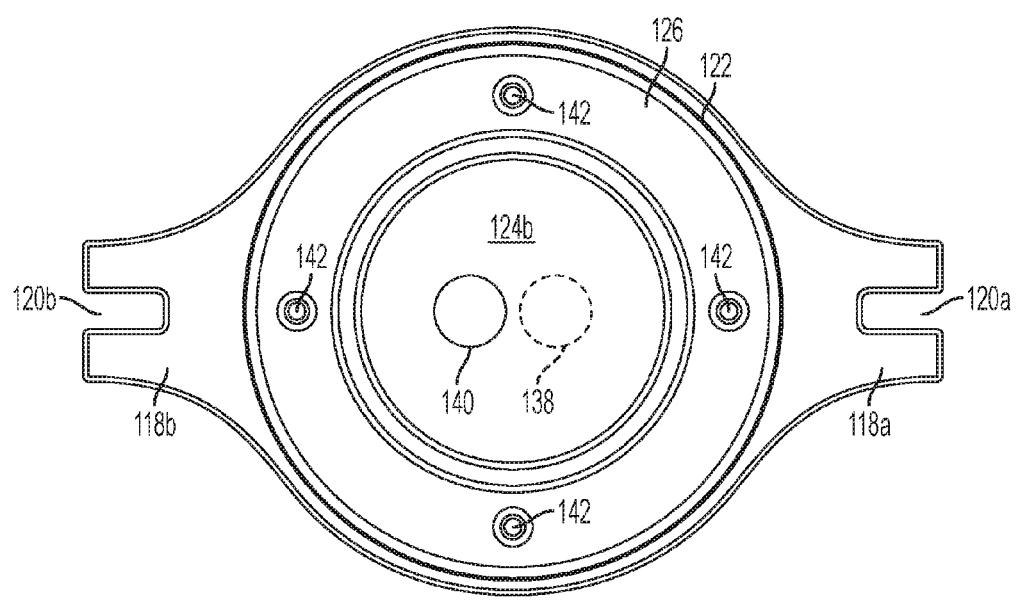
FIG. 2C is a top view of the cannula housing and compliant membranes of FIG. 2B.

FIGS. 2B and 2C are perspective and top views, respectively, of the lower cannula housing of FIG. 2A showing the membranes 124a and 124b and the retaining ring 126 installed. In the installed configuration, the membranes 124a and 124b block the passage 145, and the apertures 138 and 140 in membranes 124a and 124b do not overlap. The lack of an overlap between apertures 138 and 140 provides a torturous path for gases or fluids between the passage 145 and the proximal opening 122 in the lower cannula housing 106. To escape from the cannula tube 104 to the proximal opening 122 in the lower cannula housing 106, gas (generally, an insufflation gas, such as carbon dioxide) must pass through the aperture 138 in the first membrane 124a (which is pressed against the second membrane 124b), travel through the space between the two sandwiched membranes 124a and 124b, and then pass through the aperture 140 in the second membrane. Because the membranes 124a and 124b are stacked on top of each other and because each membrane 124a and 124b is stretched across the anchors 144, the membranes are in close contact with each other. Also, the differential pressure of the insufflation gases in the cannula tube 104 over atmospheric pressure at the proximal opening 122 in the lower cannula housing 106 presses membrane 124a into membrane 124b, thereby maintaining membrane 124a in contact with membrane 124b. This tight path between the membranes 124a and 124b through which the insufflation gases must pass to get from aperture 138 to aperture 140 is a torturous path that inhibits leakage of the insufflation gases.

The membranes 124a and 124b preferably may be made of compliant materials, described above, which enable endoscopic tools to be pushed through the apertures 138, 140 without requiring alignment of a distal end of a tool with the apertures 138, 140. For example, if the obturator shaft 115 and obturator tip 116 are reinserted into the cannula tube, they must pass through the membranes 124a and 124b. The obturator tip 116 pressing on the membranes 124a and 124b will cause the membranes 124a and 124b to stretch, and the stretching will cause the apertures 138, 140 to shift towards the obturator tip 116. Thus, by pushing the obturator tip 116 into the membranes 124a and 124b, the apertures 138, 140 in the membranes 124a and 124b automatically align with the obturator tip 116, thereby enabling the obturator tip 116 and the obturator shaft 115 to pass therethrough.

Figure 3A:
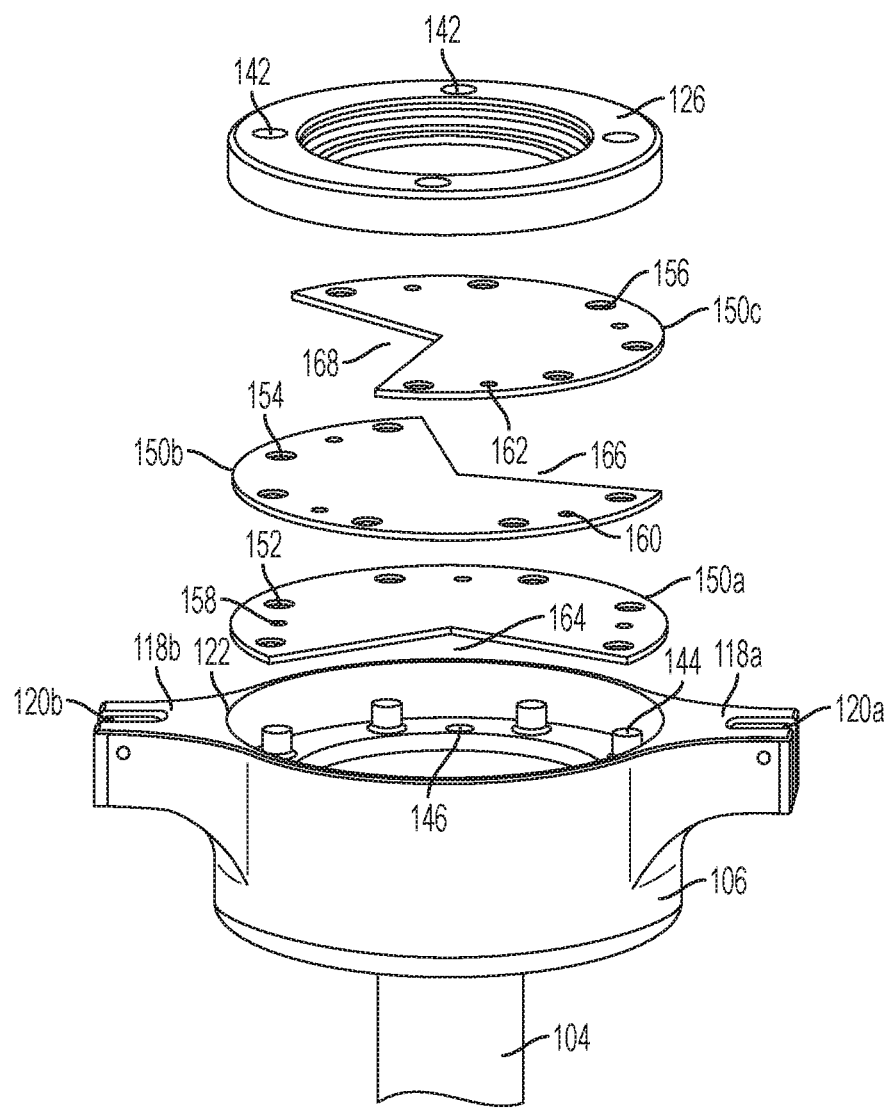
FIG. 3A is a perspective exploded view of a cannula housing and compliant membranes according to another embodiment of the present invention.
Figure 3B:
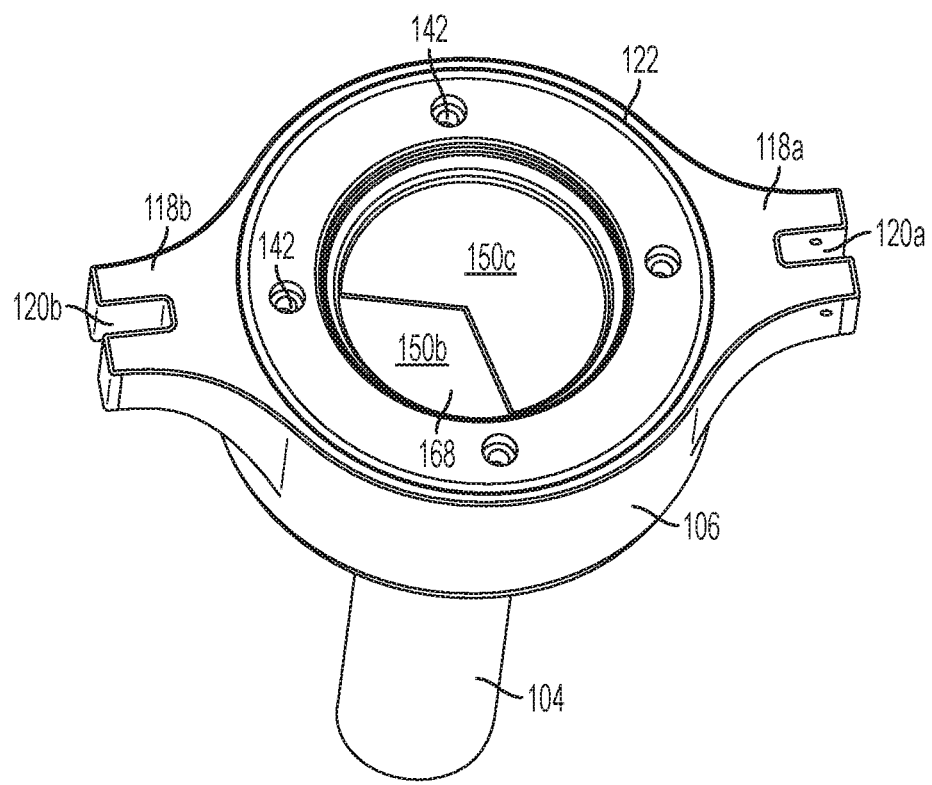
FIG. 3B is a perspective view of the top of the assembled cannula housing and compliant membranes of FIG. 3A.

FIG. 3A is a perspective exploded view of a second embodiment in which there are more than two, for example, three membranes 150a-c. In certain embodiments, such as that shown in FIG. 3A, the membranes have wedge-shaped apertures 164, 166, and 168, respectively. FIG. 3B is a perspective view of the embodiment in FIG. 3A in an installed configuration. Each wedge-shaped aperture 164, 166, 168 does not overlap apertures of adjacent layers and may not overlap the apertures 164, 166, 168 of any other membrane layer. Thus, insufflation gases from the cannula tube 104 must pass between the first membrane 150a and the second membrane 150b, and then between the second membrane 150b and the third membrane 150 to escape to the proximal opening 122 in the lower cannula housing 106 through the apertures 164, 166, and 168. Furthermore, the wedge-shaped apertures 164, 166, 168 preferably do not extend over the center point of the respective membranes 150a-c so that the wedge-shaped apertures 164, 166, 168 do not overlap in any way to form a direct path through which insufflation gases may escape.

Figure 4A:
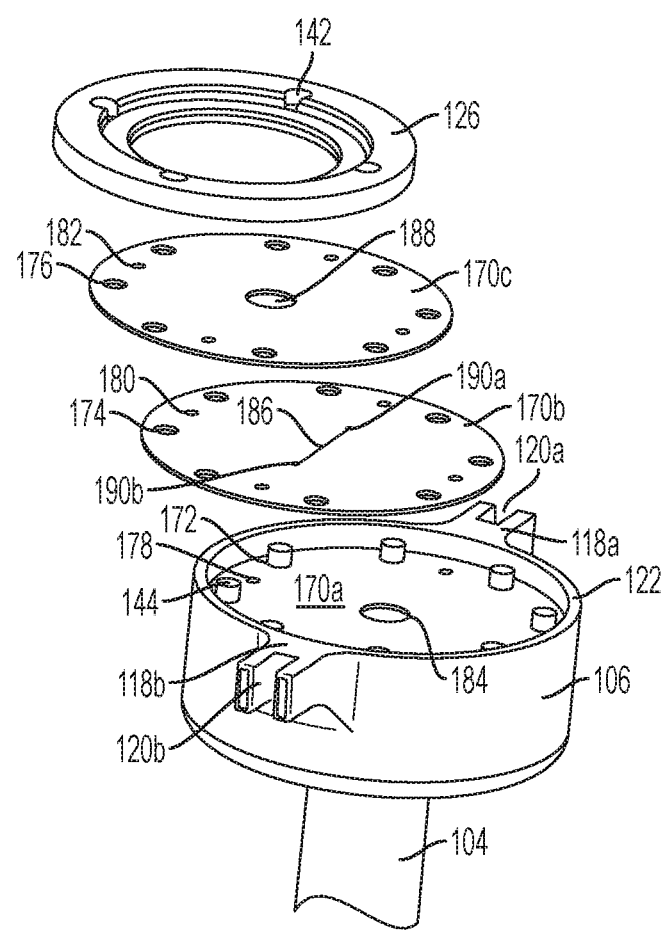
FIG. 4A is a perspective exploded view of a cannula housing and compliant membranes according to another embodiment of the present invention.

FIG. 4A is a perspective partially-exploded view of another embodiment in which there are three membranes 170a (shown installed), 170b, and 170c. Membrane 170a has a circular aperture 184 proximate to its center and membrane 170c also has a circular aperture 188 proximate to its middle. Membrane 170b has a slit 186 as an aperture. For clarity, the slit 186 is shown with a gap between its sides. However, the slit may be formed by cutting a line in the membrane 170b, removing no membrane material or a negligible amount of membrane material such that the slit 186 has no gap when the membrane 170b is not deformed. Additionally, the slit 186 may include relief cuts 190a and 190b at its ends. The relief cuts 190a,b provide for stress relief at ends of the slit 186 when the slit is stretched and enables the slit 186 to stretch to a larger shape without tearing the membrane. FIG. 4D shows a slit 186 without relief cuts 190a and 190b stretched open, e.g., by an endoscopic tool. The size of the opening of slit 186 is limited by the ends. FIG. 4E shows the slit 186 with relief cuts 190a and 190b at end. The relief cuts 190a and 190b enable the slit 186 to open to a larger size.

Figure 4B:
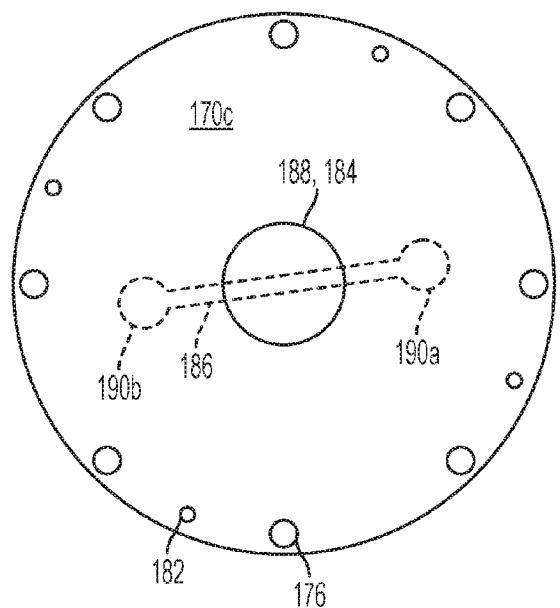
FIG. 4B is a top view of compliant membranes according to another embodiment of the present invention, showing apertures in respective membranes in broken line.
Figure 4C:
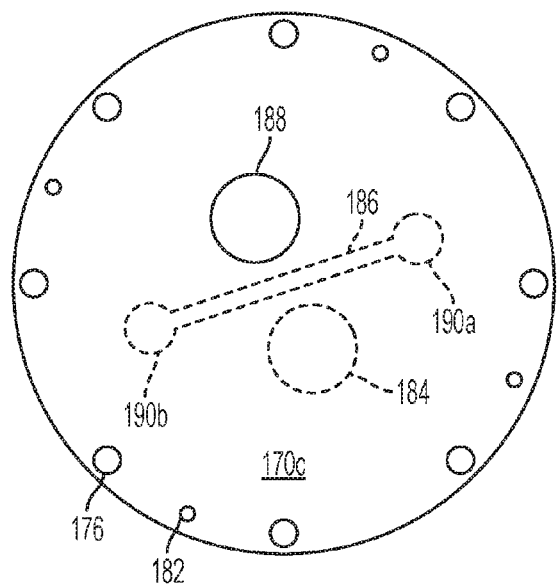
FIG. 4C is a top view of compliant membranes according to another embodiment of the present invention, showing apertures in respective membranes in broken line.
Figure 4D:
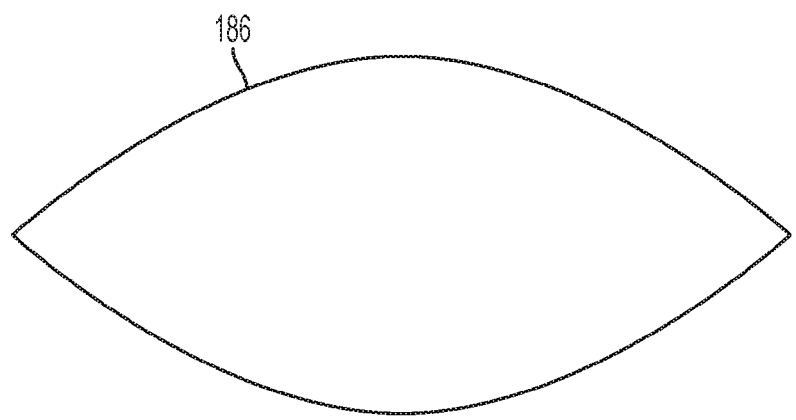
FIG. 4D is a top view of a slit aperture in a compliant membrane with no relief cuts at its ends in a stretched open configuration.
Figure 4E:
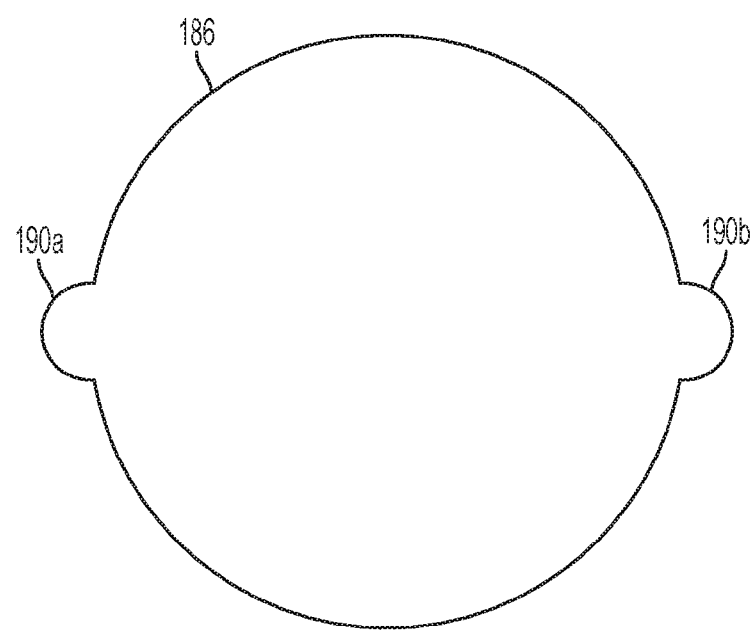
FIG. 4E is a top view of a slit aperture in a compliant membrane with relief cuts at its ends in a stretched open configuration.

In certain embodiments, such as that shown in FIG. 4B, the apertures 184, 186, and 188 may be arranged on their respective membranes 170a, 170b, and 170c such that the apertures 184, 186, and 188 overlap when the membranes 170a, 170b, and 170c are stacked in the lower cannula housing 106. In certain embodiments, such as that shown in FIG. 4C, the apertures 184, 186, and 188 may be arranged on their respective membranes 170a, 170b, and 170c such that the apertures do not overlap when the membranes 170a, 170b, and 170c are stacked in the lower cannula housing 106. In certain embodiments, the apertures 184, 186, and 188 may be arranged on their respective membranes 170a, 170b, and 170c such that the apertures partially overlap when the membranes 170a, 170b, and 170c are stacked in the lower cannula housing 106. As described above, differential pressure of the insufflation gas over atmospheric pressure presses the membranes against each other. The slit 186 in membrane 170b is assisted in remaining closed by being sandwiched between membranes 170a and 170c.

Figure 6B:
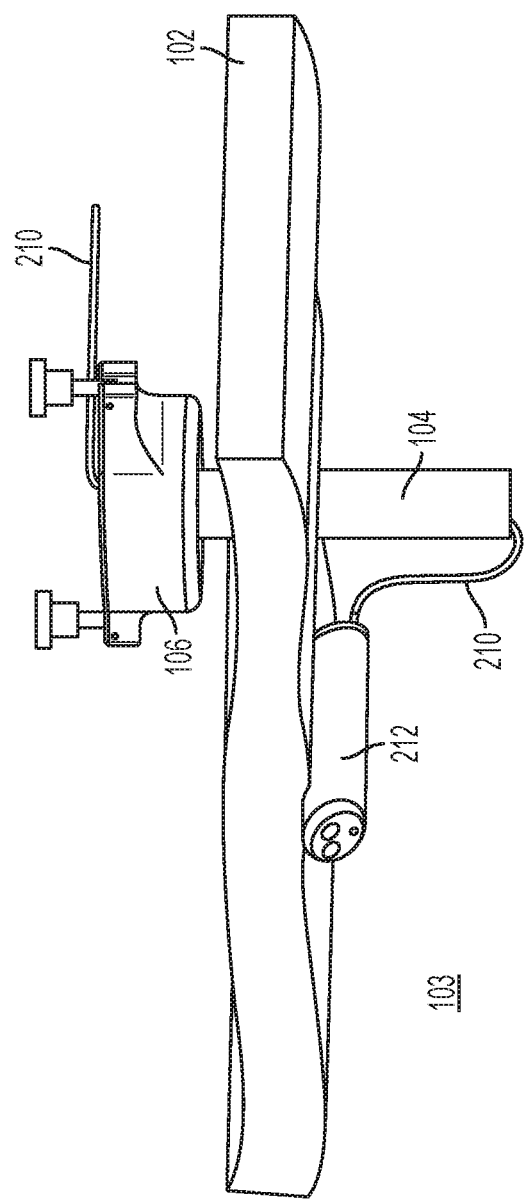
FIG. 6B is a perspective view of the cannula housing of FIG. 6A showing a camera in an internal site of a patient attached to the tether.

FIG. 5 shows a cannula tube 104 inserted through tissue 102 with membranes, such as any of the membranes described above in FIGS. 2A-4C, installed in the lower cannula housing 106. FIGS. 6A-B show a magnetic camera 212 placed in the abdominal cavity 103 through the lower cannula housing 106 and the cannula tube 104. The camera 212 may be attached to a tether 210. The tether includes one or more strands, for example, one strand may carry power to the camera, another strand carries image data from the camera, and another strand possibly carries gases or fluids to ports attached to the camera. The tether 210 runs from the camera 212 through the cannula tube 104 and the lower cannula housing 106. The tether 210 also passes through apertures 214 in membranes 212, such as, for example, the membranes 124a-b, 150a-c, and 170a-c described above. FIGS. 5 and 6A-B also show thumb screws 114a and 114b mounted on respective posts 200a and 200b. The posts 200a and 200b include threaded ends (not shown) onto which the thumb screws 114a and 114b are mounted. The posts 200a and 200b are connected to respective buttresses 118a and 118b by pins 202a and 202b. When the thumb screws are in a loose position, the thumb screws 114a and 114b may be rotated about pins 202a and 202b in the direction of arrows labeled "A" and "A'" about axes of rotation "B-B" and "B'-B'", respectively, in FIG. 5, to be out of the way of the upper cannula housing 108 being placed on top of the lower cannula housing 106. After the upper cannula housing 108 is placed on top of the lower cannula housing 106, the thumb screws 114a and 114b may be rotated in directions opposite to arrows "A" and "A'". Then, the thumb screws 114a and 114b may be turned on their respective posts 200a and 200b such the thumb screws 114a and 114b clamp down on respective buttresses 109a and 109b of the upper cannula housing 108.

FIG. 7 shows the upper cannula housing 108 and the cannula head 110 mounted on top of the lower cannula housing 106. The upper cannula housing 108 includes a port housing 216 that includes one or more ports 218a and 218b. The ports 218a and 218b provide a path for the tether 210 to exit the cannula tube 104 and the cannula housing 106, 108. The number of ports may correspond to the number of strands making up the tether 210, wherein each strand may pass through a distinct port. The ports 218a and 218b are sized to accommodate the tether 210. The ports 218a and 218b may be sized such that the tether 210 fits snugly therethrough or the ports 218a and 218b may include an additional gasket through which the tether 210 runs. For example, the gasket may be a compliant membrane that covers a port, such as, for example, port 218a, and the compliant membrane may include an aperture through which the tether may pass. The gasket also may be an o-ring positioned within a port, such as, for example, port 218a, that snugly fits with a tether passing therethrough. The snug fit of the gasket further retards leakage of insufflation gases. When the tether 210 is drawn through the ports 218a and 218b, the tether 210 is biased to a side of the cannula tube 104, i.e., away from the center of the cannula tube 104 nearest to the ports 218a and 218b. Consequently, the tether 210 is out of the way of any additional endoscopic tools passing through the cannula tube 104.

Figure 8:
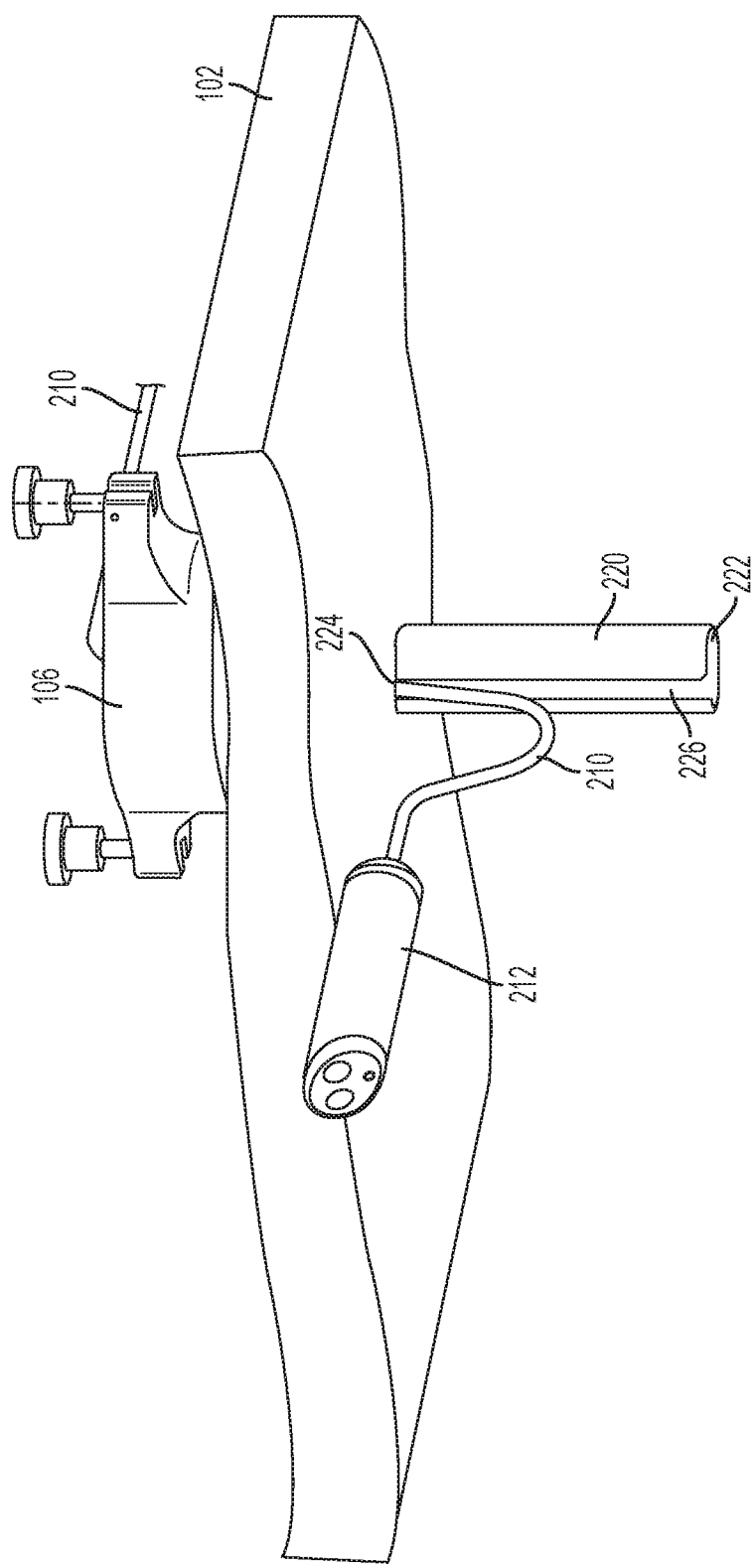
FIG. 8 is an embodiment of a cannula and tethered housing from the perspective of an internal site of the patient.

FIG. 8 shows another embodiment of a cannula tube 220 having a slot 226 defining an opening running along the length of the cannula tube 220, generally, and preferably substantially parallel to its longitudinal axis. The slot 226 enables the tether 220 to exit the cannula tube 220 at a more proximal point 224 than the distal end 222 of the cannula tube 220. Removing the tether 210 from the cannula tube 220 at the more proximal point 224 minimizes interactions between the tether 210 and other endoscopic devices (not shown) in the cannula tube 220, which may cause tugging on the tether 210 (and inadvertent movement of the camera 212) or cause inadvertent movement of endoscopic tools.

In various embodiments, the cannula housing may be structured for movement to reposition the openings to the passage. For example, FIGS. 9A-9I show an embodiment of a cannula including a bracket 230 and a rotating housing 233. The rotating housing 233 includes a passage 276 (FIG. 9B) that is in fluid communication with a bracket opening 270 (FIG. 9D) in the bracket 230. The rotating housing 233 may also include a first opening 272 and a second opening 274, each of which can be in fluid communication with the passage 276. The first opening 272 may include first membranes 236 and respective apertures 238. The second opening 274 may include second membranes 244 and respective apertures 246. In certain embodiments, the first membranes 236 and the second membranes 244 can include a plurality of membranes, similar to the membranes shown in FIGS. 2A-4E. The apertures 238 and 246 can be in fluid communication with the passage 276. The bracket 230 may be coupled to a hollow cannula tube 220 and the bracket opening 270 may be in fluid communication with the cannula tube 220. The cannula tube 220 may include a longitudinal slot 226. Alternatively, the cannula tube 220 can be similar to those shown above with respect to FIGS. 1A-7, for example. The rotating housing 233 is rotationally coupled to the cannula bracket 230 by bearings 240. The bearings 240 may be any type of bearings, such as ball bearings, planar bearings, and/or journal bearings, for example.

A seal housing 260 can be positioned intermediate the bracket 230 and the rotating housing 233. Referring particularly to FIG. 9E, the seal housing 260 can include an interior surface 262 that includes a slightly larger profile than an exterior cylindrical surface of the rotating housing 233. The seal housing 260 also includes a seal passage 266 in fluid communication with the bracket opening 270 and the passage 276 in the rotating housing 233. When assembled, the close fit between the rotating housing 233 and the seal housing 260 provides a seal for the passage 276 and/or the first and second openings 272 and 274 that can inhibit the escape of gases. For example, in use, insufflation gases in a patient's abdomen can be inhibited from escaping through the cannula tube 220 and the passage 276 by the interior surface 262 of the seal housing 260. The interior surface 262 of the seal housing 260 can also inhibit the escape of insufflation gases through the first opening 272 when the rotating housing 233 is rotated such that the first opening 272 is aligned with a portion of the interior surface 262, an example of which is illustrated in FIG. 9H. The interior surface 262 of the seal housing 260 can also inhibit the escape of insufflation gases through the second opening 274 when the rotating housing 233 is rotated such that the second opening 274 is aligned with a portion of the interior surface 262, an example of which is illustrated in FIG. 9D.

Referring to FIG. 9H, the aperture 238 is shown as a slit that is aligned with a slit 264 in the seal housing 260. The slit 264 in the seal housing 260 can accommodate the tether 210 of the camera. In certain embodiments, the aperture 238 may not be aligned with the slit 264 in the seal housing 260 to further inhibit the escape of insufflation gases. For example, if the aperture 238 is a slit, such as the slit shown in FIG. 9H, then the aperture 238 may be rotated ninety degrees relative to the slit 264 in the seal housing 260. As another example, if the aperture 238 is a circular hole, then the hole may be offset from the slit 264 in the seal housing 260.

Figure 9A:
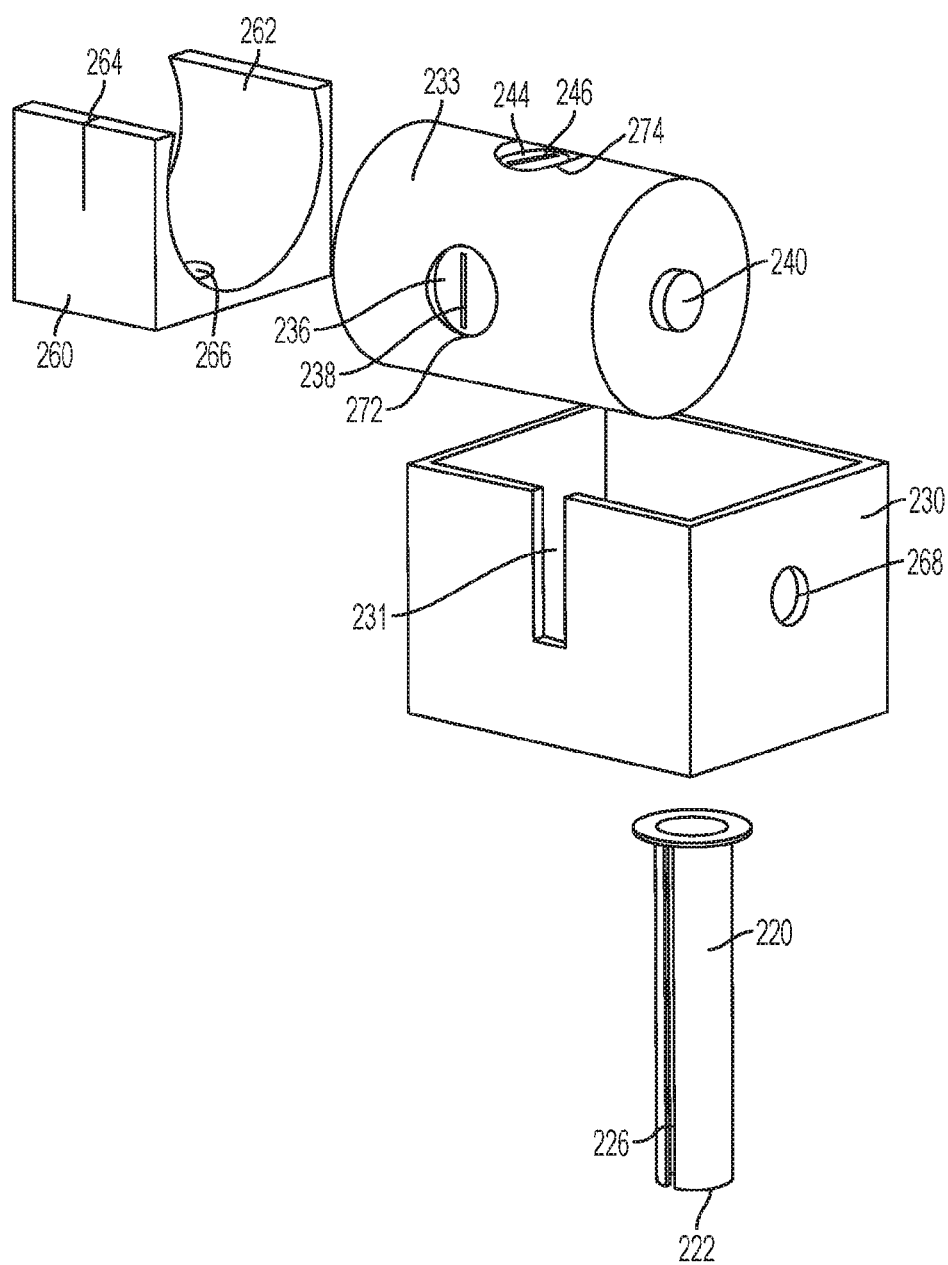
FIG. 9A is a front exploded view of a cannula tube and housing according to an alternative embodiment of the present invention.
Figure 9B:
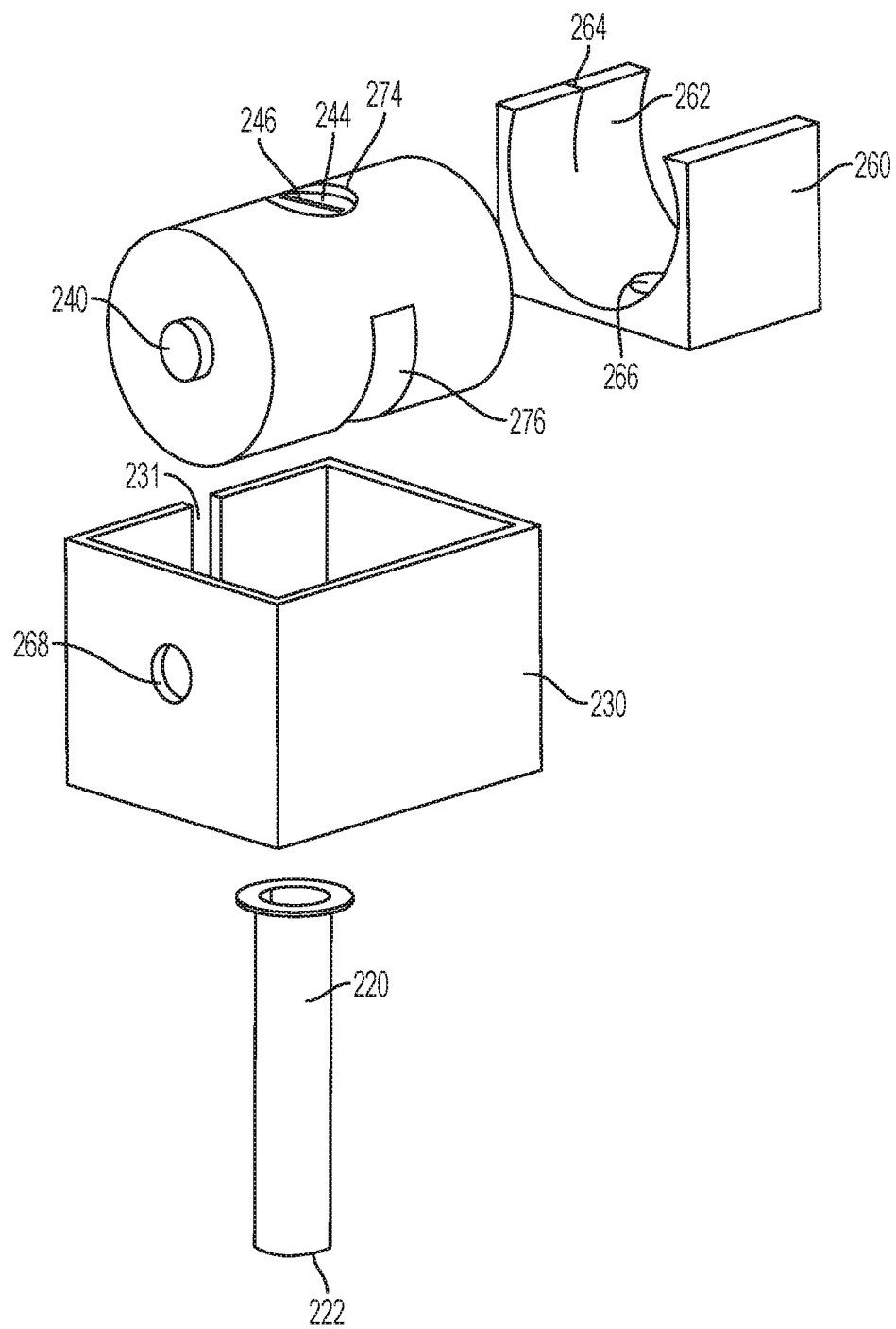
FIG. 9B is a rear exploded view of the cannula tube and housing of FIG. 9A.
Figure 9C:
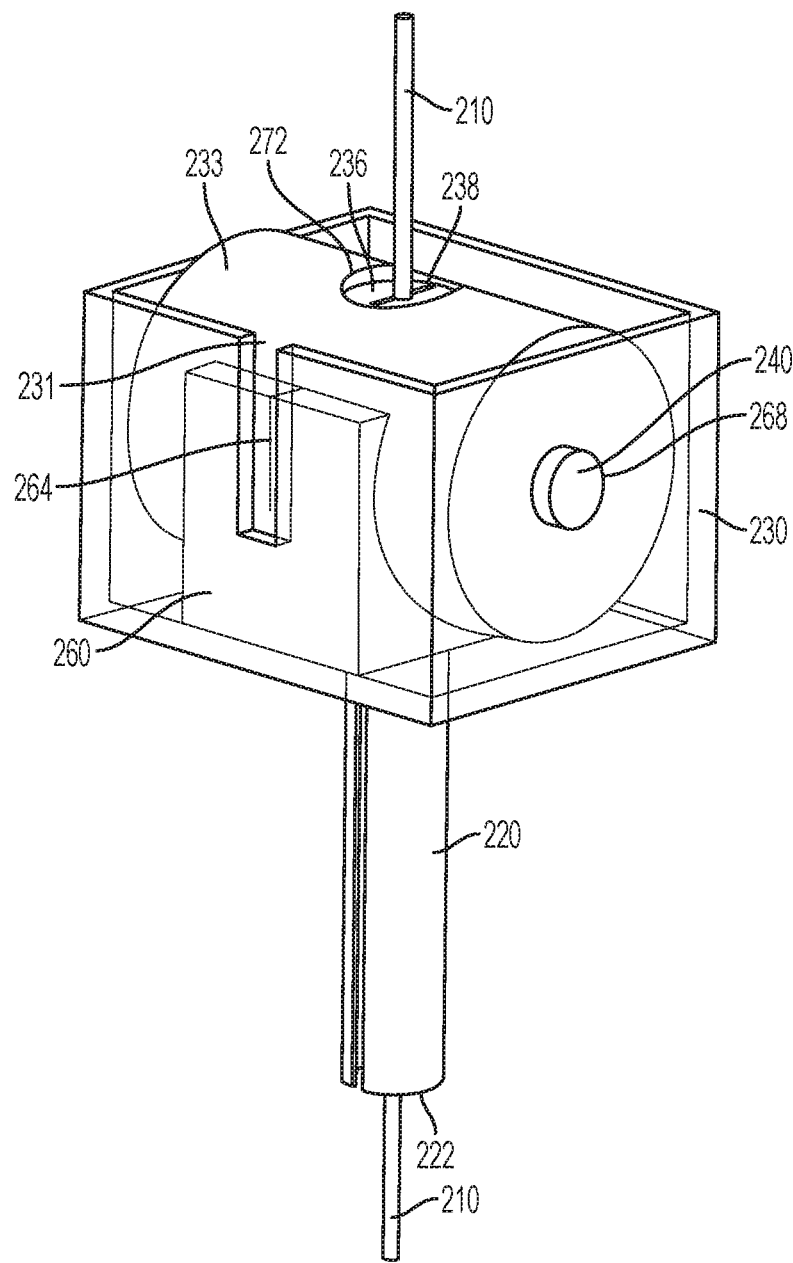
FIG. 9C is a front perspective view of the cannula tube and housing of FIG. 9A with a tether passing therethrough, wherein the bracket is shown as clear for visibility of the housing.
Figure 9D:
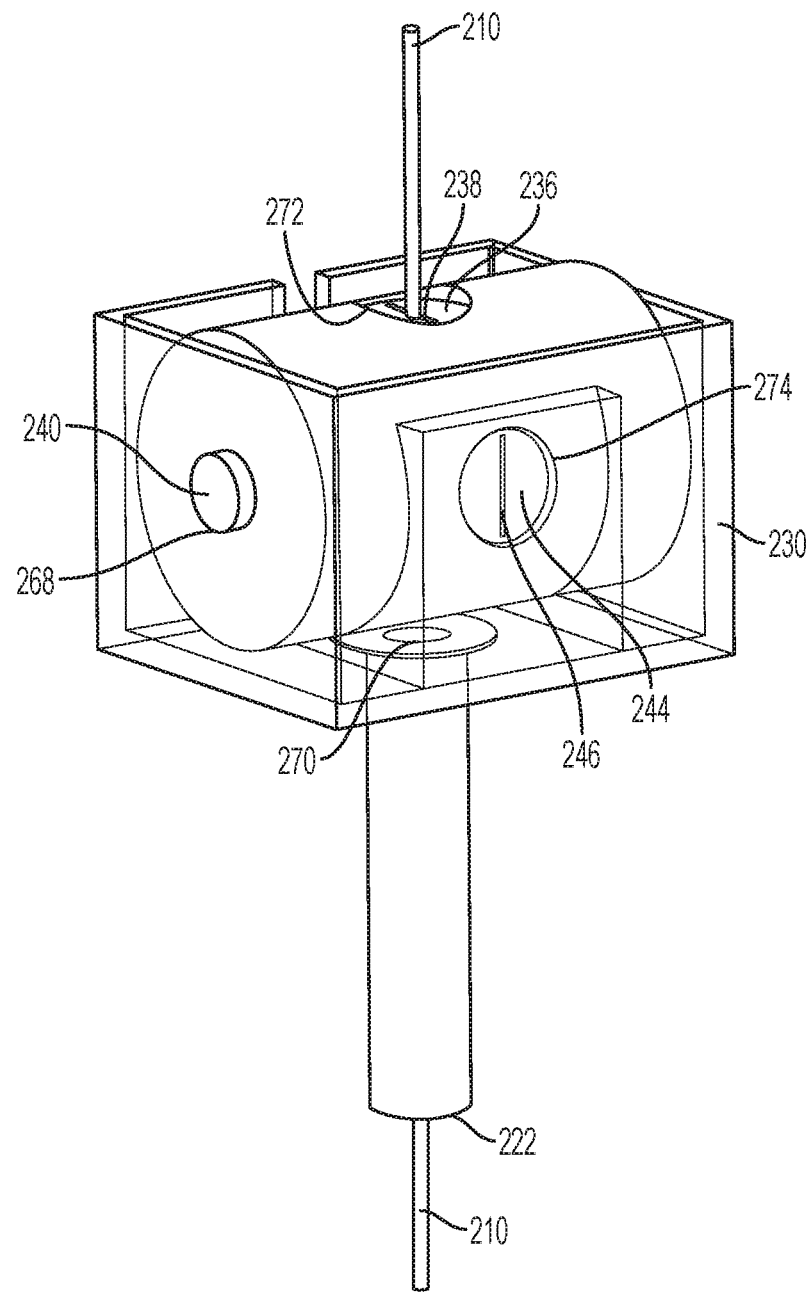
FIG. 9D is a rear perspective view of the cannula tube and housing of FIG. 9A with the tether passing therethrough, wherein the bracket is shown as clear for visibility of the housing.
Figure 9E:
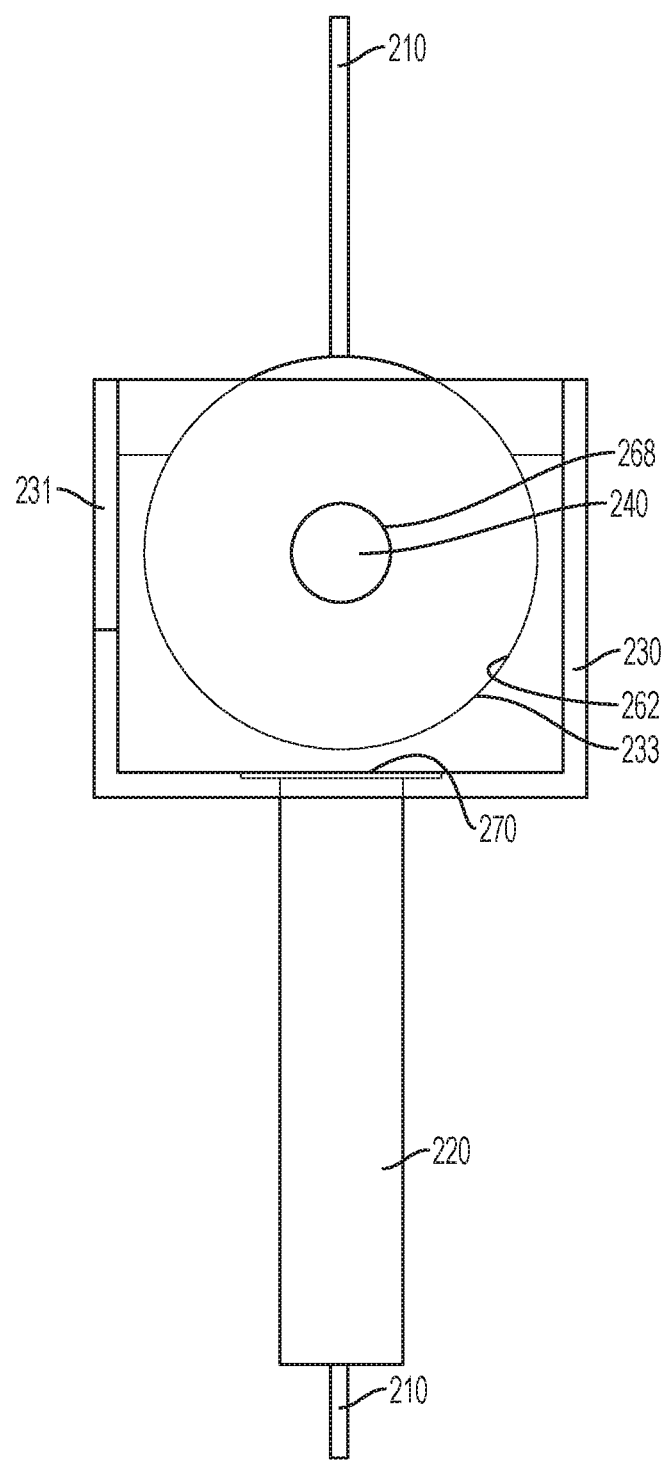
FIG. 9E is a side view of the cannula tube and housing of FIG. 9A with the tether passing therethrough, wherein the bracket is shown as clear for visibility of the housing.
Figure 9F:
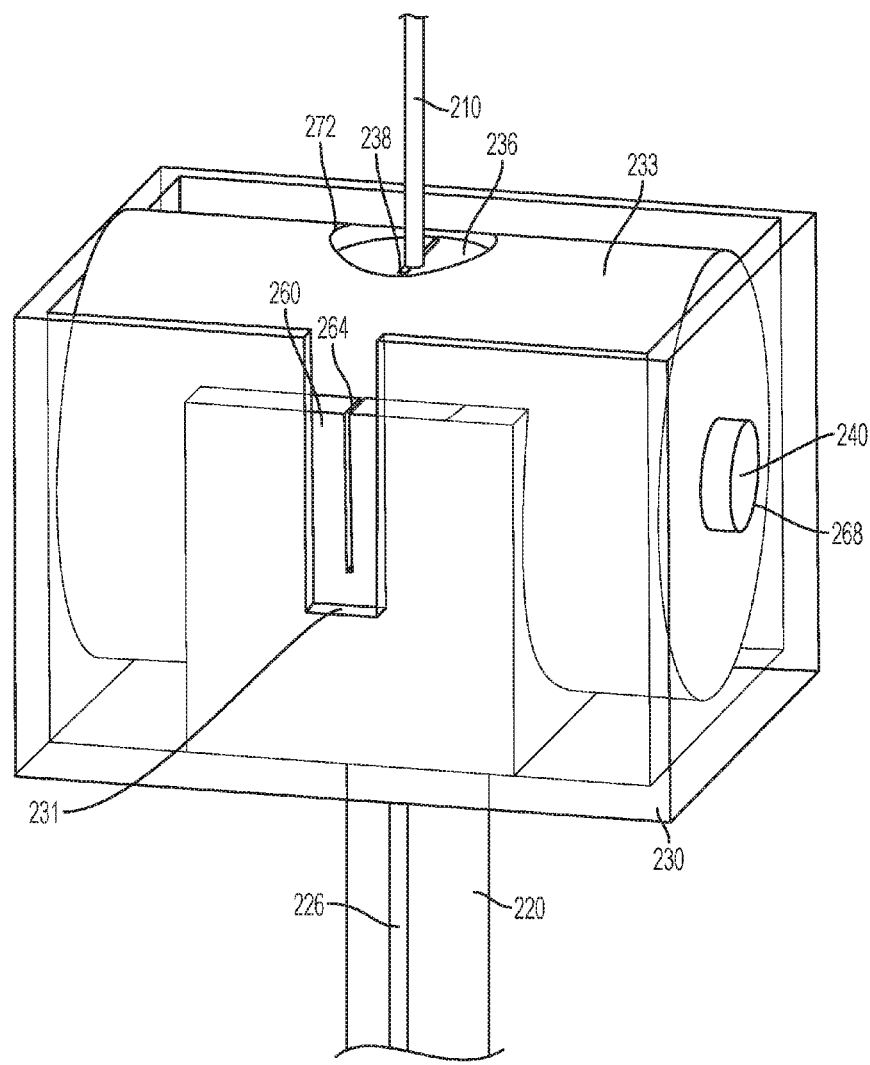
FIG. 9F is a front perspective view of the cannula tube and housing of FIG. 9A with the tether passing therethrough, wherein the bracket is shown as clear for visibility of the housing.

Referring to FIG. 9C, in use, the rotating housing 233 can be oriented such that the first opening 272 is aligned with a longitudinal axis of the cannula tube 220 and the bracket opening 270. An obturator shaft and tip, such as obturator shaft 115 and obturator tip 116, shown in FIG. 1A, may be inserted through the first opening 272 and the apertures 238 in the membranes 236 therein such that the obturator top 116 protrudes from the distal end of the cannula tube 220. An obturator grip, such as obturator grip 112, may be attached to a proximal end of the obturator shaft 115, and may couple to the cannula housing 233 and/or the bracket 230. The obturator tip 116 may guide the cannula tube 220 through an otomy in a patient. Then, the obturator shaft 115 and obturator tip 116 can be removed from the cannula tube 220, bracket 230, and rotating housing 233. As illustrated in FIG. 9I, the close spacing between the seal housing 260 and the rotating housing 233 can inhibit the escape of insufflation gases through the passage 276 in the rotating housing. A camera can be passed through the apertures 238 in the first membranes 236 and through the cannula tube 220 and into a body cavity. Referring to FIGS. 9C-9F, a tether 210 of the camera is shown passing through the first apertures 238 and out through the cannula tube 220.

Figure 9G:
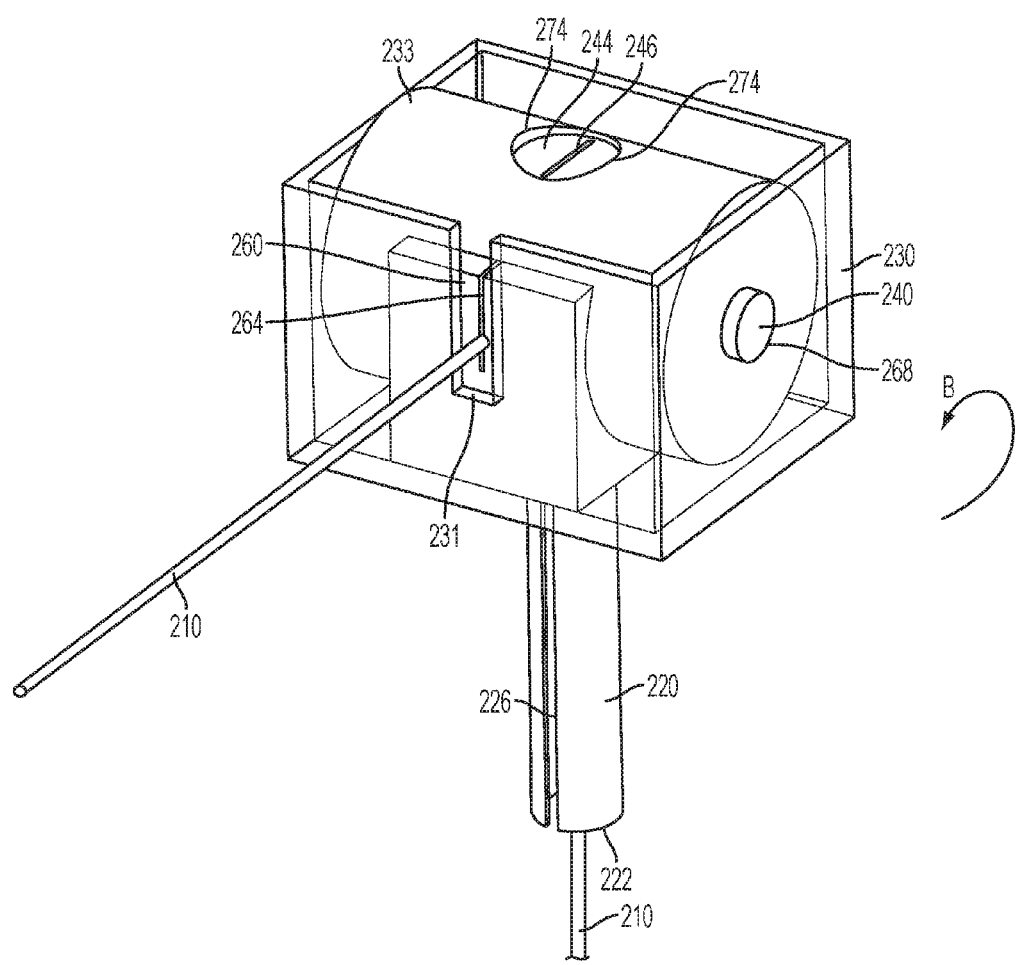
FIG. 9G is a perspective view of the cannula tube and housing of FIG. 9F with the tether passing therethrough, wherein the housing is moved to a rotated positioned.
Figure 9H:
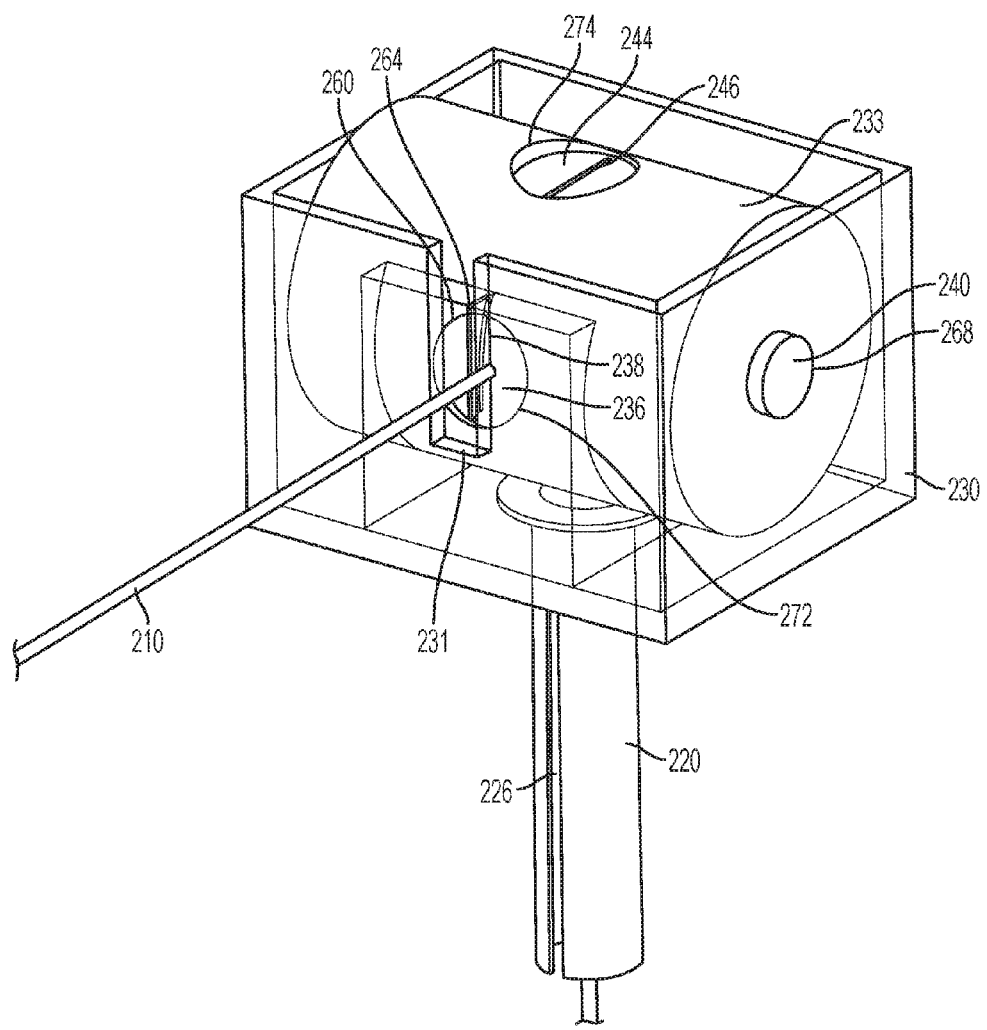
FIG. 9H is a second perspective view of the cannula tube and housing of FIG. 9F with the tether passing therethrough, wherein the housing is moved to a rotated positioned.
Figure 91:
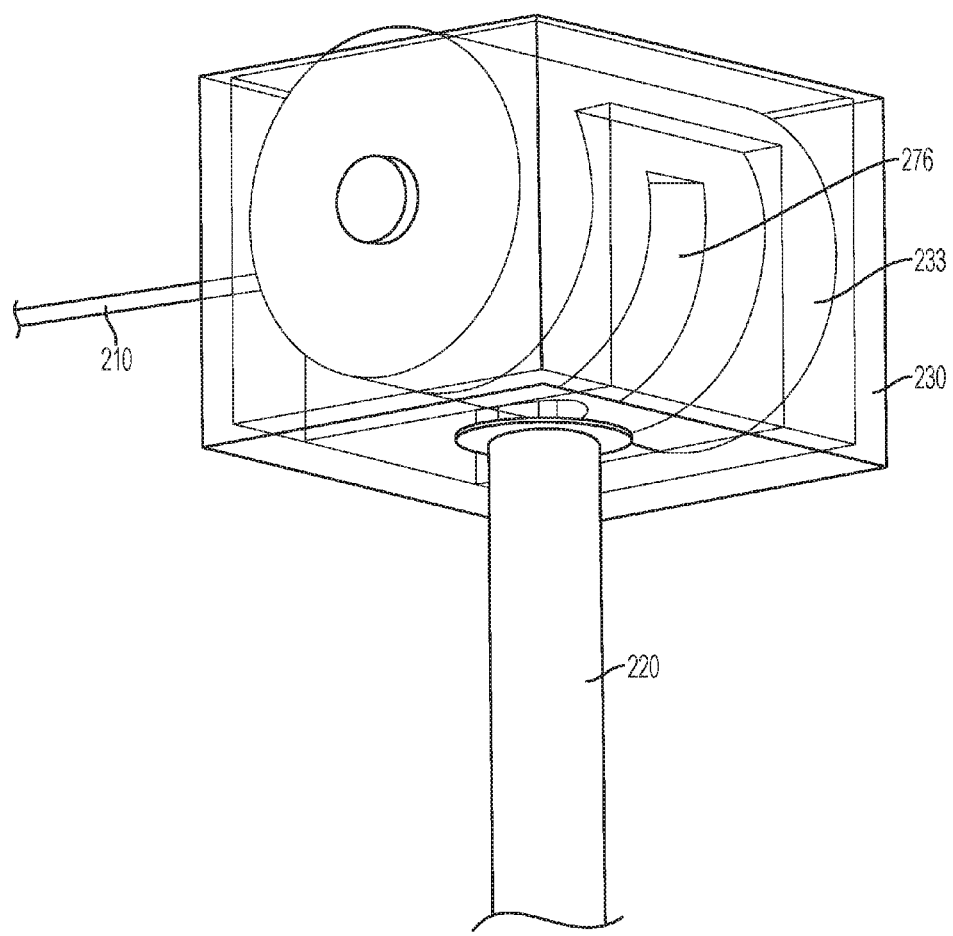

Referring to FIG. 9G, after the camera is positioned in the body cavity and the tether 210 passes through the cannula tube 220 and the first opening 272 in the rotating housing 233, the rotating housing 233 can be rotated in the direction of arrow B. In the rotated configuration, the first opening 272 is not aligned with the longitudinal axis of the cannula tube 220. As a result, the tether 210 is biased toward a perimeter of the cannula tube 220. If the cannula tube 220 includes a longitudinal slot 226, then it can be advantageous for the tether 210 to be biased toward a side of the cannula tube 220 on which the longitudinal slot 226 is located. With the tether 210 biased towards the perimeter of the cannula tube 220, additional surgical instruments can be inserted through the apertures 246 in the second membranes 244 and the cannula tube 220 while minimizing interference between the tether 210 and the surgical instrument. Any interference can cause tugging of the tether, which may cause undesired movement of the camera in the patient. Any interference can also cause unwanted movement of the surgical instrument. In the rotated configuration, the first opening 272 is adjacent to the interior surface 262 of the seal housing 260. The slit 264 or similar opening in the seal housing 260 can accommodate the tether 210 of the camera as shown in FIGS. 9G and 9H.

Figure 10A:
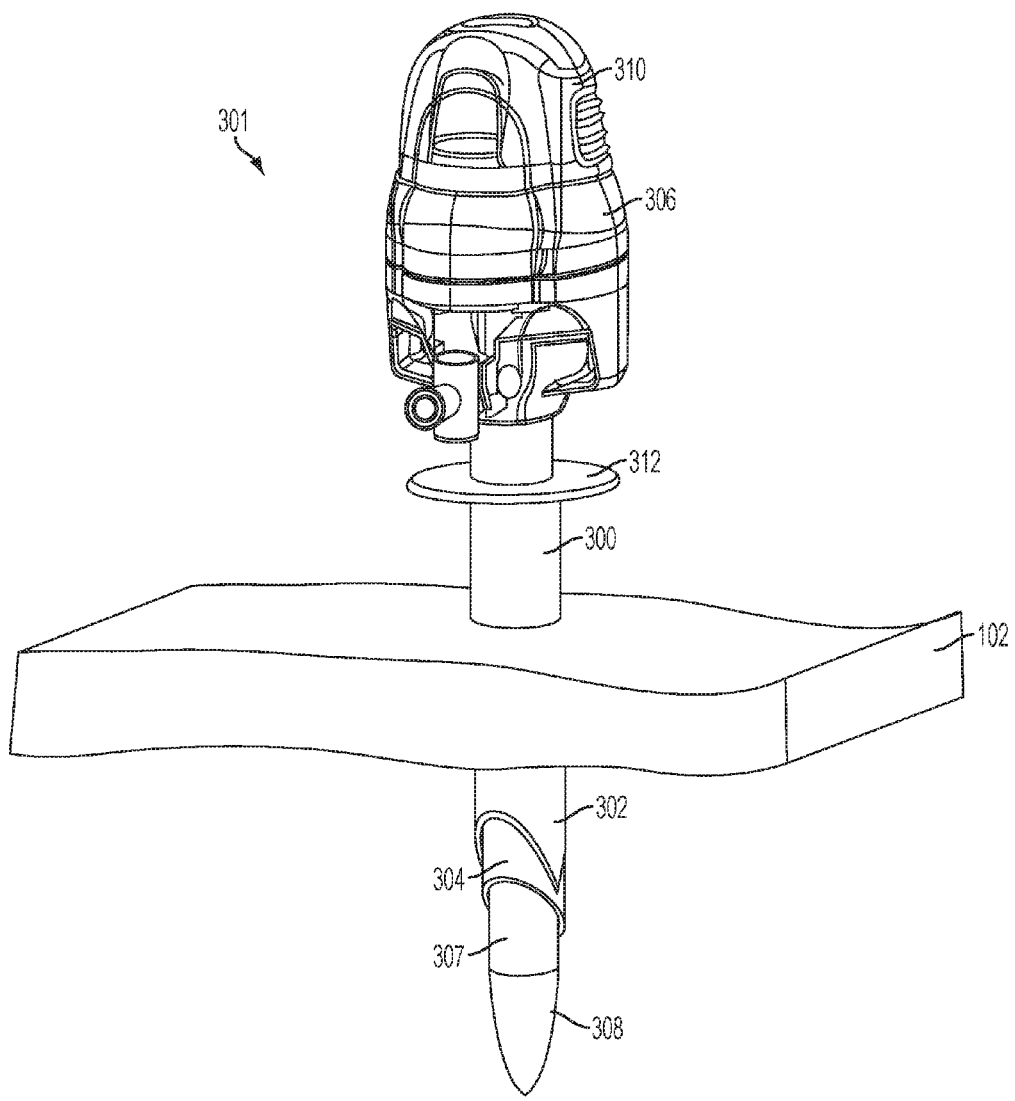
FIG. 10A is a perspective view of a trocar and obturator assembly according to an embodiment of the present invention.

In various embodiments, a cannula sleeve may be provided for enhanced sealing. Referring to FIG. 10A, a perspective view of another embodiment of a trocar assembly 301 passing through a cannula sleeve is shown. The trocar assembly 301 includes a cannula head 306 attached to a cannula tube 304. An obturator shaft 307 and obturator tip 308 are attached to an obturator grip 310, and the obturator shaft 307 and obturator grip 308 pass through the cannula head 306 and cannula tube 304. A cannula sleeve 300 surrounds or encases the cannula tube 304. The cannula sleeve 300 includes a seal 302 at its distal end. When the trocar assembly 301 penetrates tissue 102, the cannula sleeve 300 also penetrates the tissue 102.

Figure 10B:
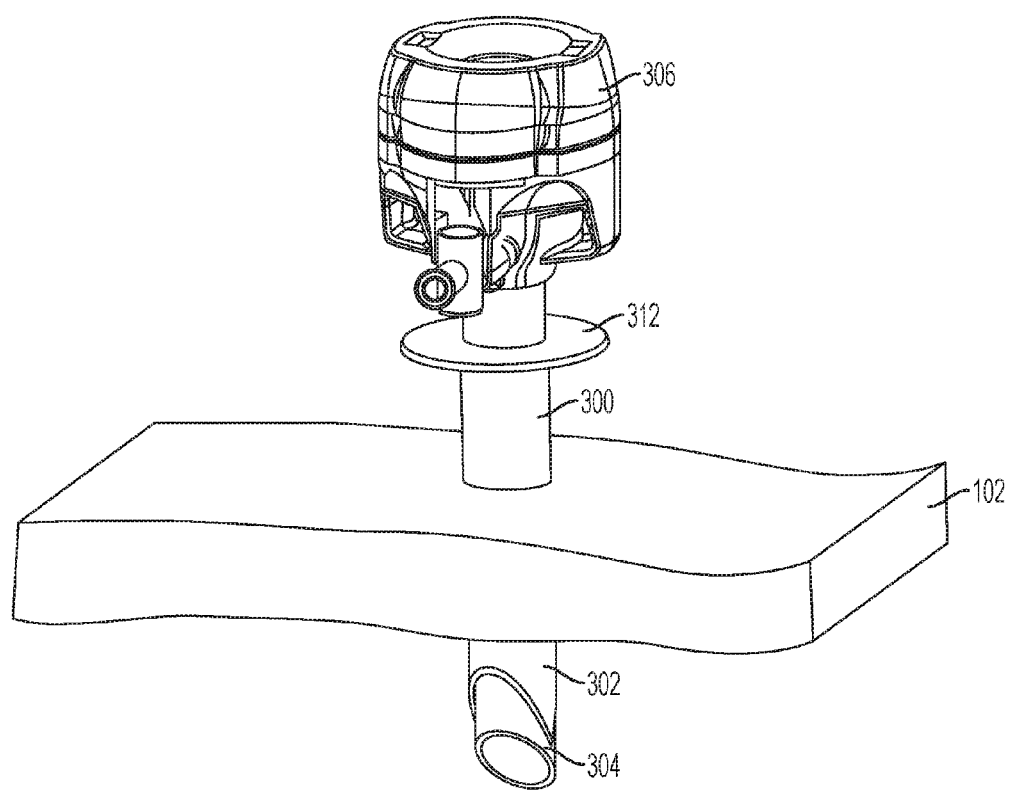
FIG. 10B is a perspective view of the trocar assembly of FIG. 10A wherein an obturator assembly is removed.
Figure 10C:
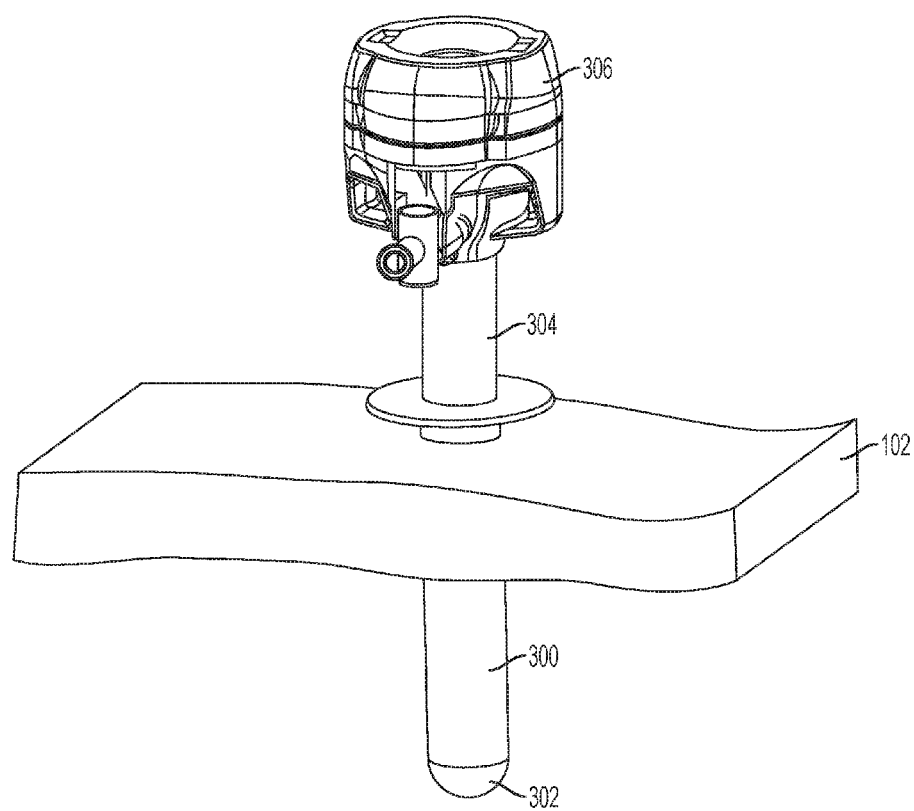
FIG. 10C is a perspective view of the trocar assembly of FIG. 10B wherein a cannula assembly is partially removed from an embodiment of a cannula sleeve, showing a seal on the sleeve in a closed position.
Figure 10D:
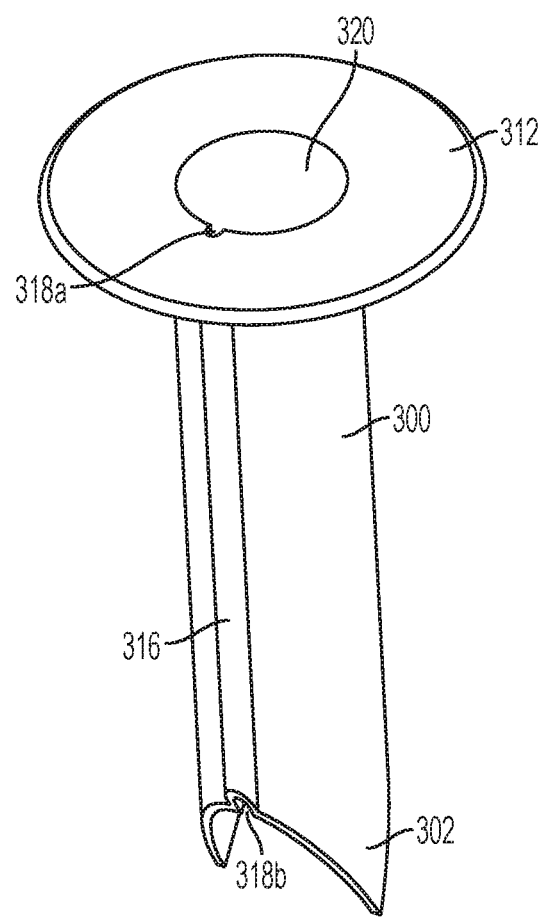
FIG. 10D is a perspective view of an embodiment of a cannula sleeve of the trocar assembly of FIG. 10A, showing the seal on the sleeve in an open position.
Figure 10E:
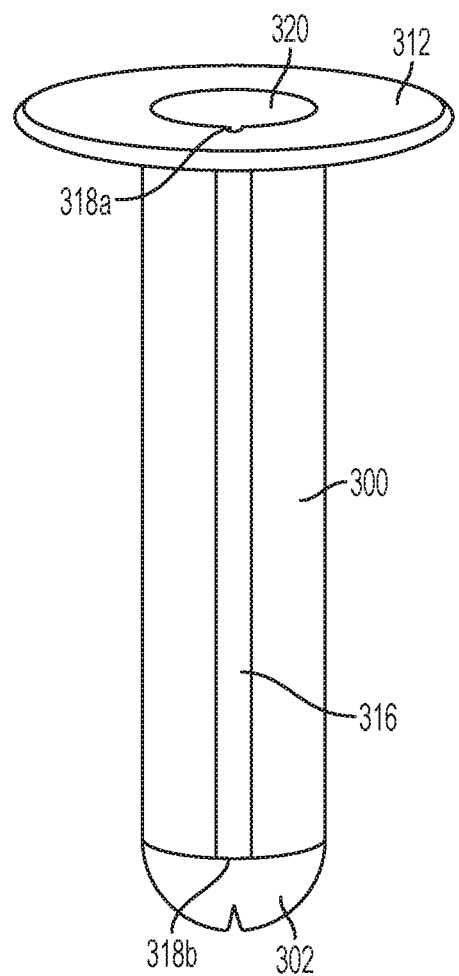
FIG. 10E is a perspective view of the cannula sleeve of FIG. 10D showing the seal on the sleeve in the closed position.
Figure 10F:
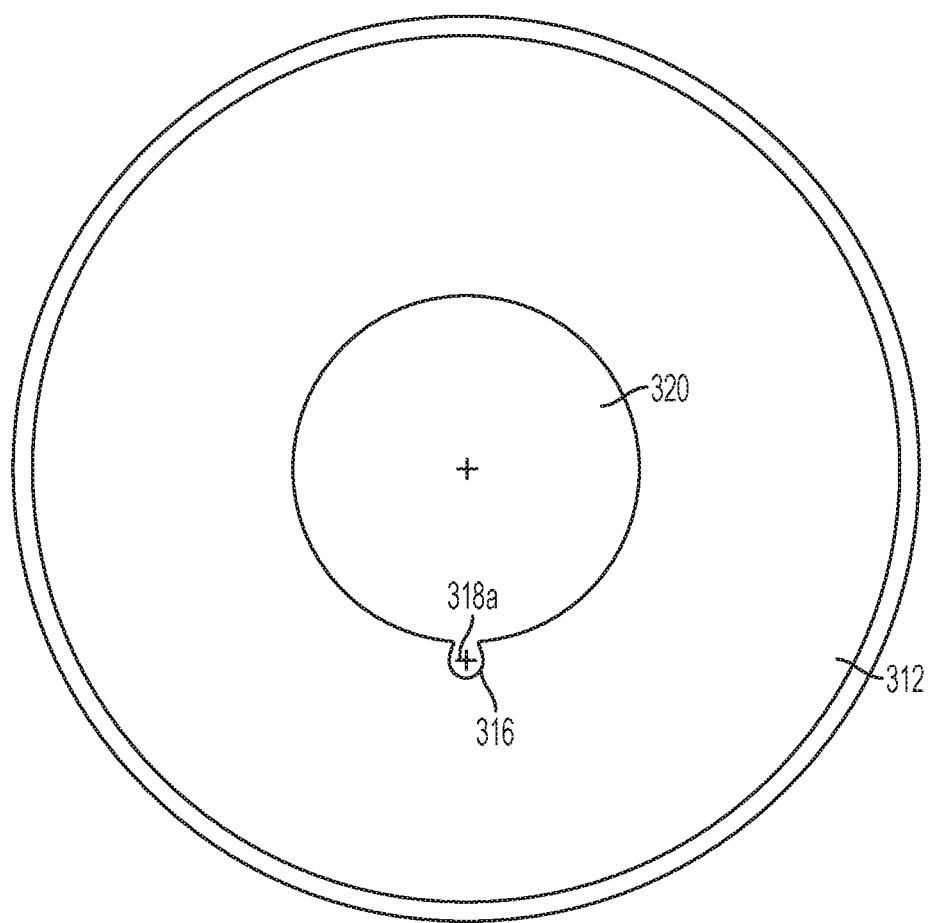
FIG. 10F is a top view of the cannula sleeve of FIG. 10D.
Figure 10G:
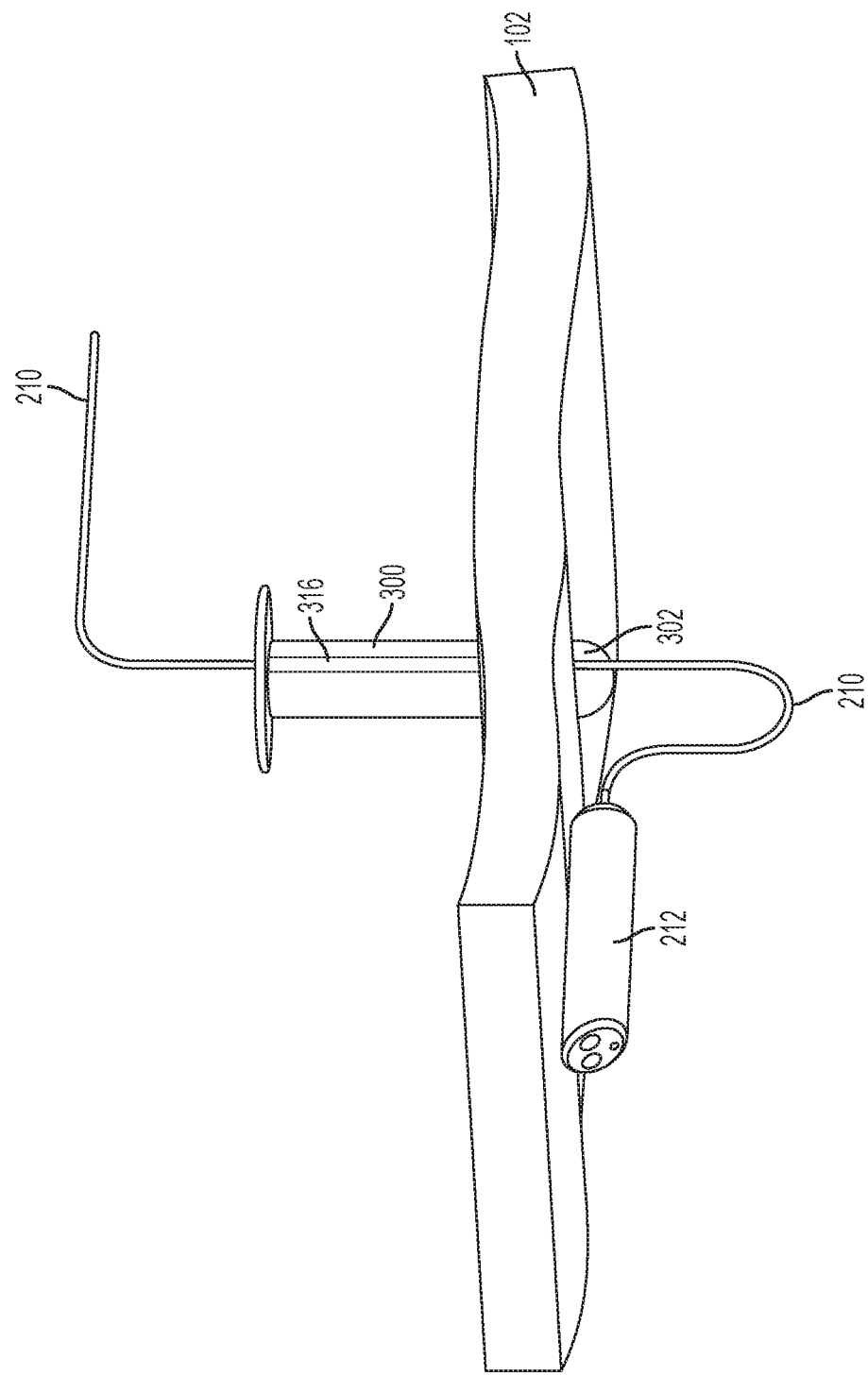
FIG. 10G is a perspective view of the cannula sleeve of FIG. 10D with a camera and tether.

FIG. 10D shows the cannula sleeve 300 alone. The cannula sleeve 300 includes a sleeve seal 302 at its distal end. In FIG. 10D, the sleeve seal 302 is shown in its open configuration. The sleeve seal 302 preferably is biased in a closed position (as shown in FIG. 10E). The sleeve seal 302 may be a duckbill seal, a clamshell seal, or any other type of seal. The cannula sleeve 300 generally comprises a substantially rigid or semi-rigid material, such as, for example, plastic or stainless steel. The sleeve seal 302 comprises a compliant material, such as, for example, silicone or rubber. The sleeve seal 302 may be attached to the cannula sleeve 300 by, for example, overmolding, adhesives, fasteners, welding, or the like. The cannula sleeve 300 may include a sleeve flange 312. The sleeve flange 312 provides a surface that can stops the cannula sleeve 300 from accidentally passing completely through an otomy in tissue. The cannula sleeve 300 also includes a tether channel 316. As shown in FIGS. 10D and 10G, the tether channel 316 may be outside of the periphery of the cannula tube 300 but also is in fluid communication with the hollow interior of the cannula tube 300. The tether channel 316 may include an open end 318a at its proximal end and an open end 318b at its distal end. The tether channel 316 and the open ends 318a and 318b can receive a camera tether, enabling the camera tether to pass through the cannula sleeve 300 without intruding on the hollow interior of the cannula tube 300. The open end 318b at the distal end of the cannula tube 300 also enables a camera tether to bypass the sleeve seal 302. As shown in FIG. 10E, when the sleeve seal 302 is closed, the hollow interior of the cannula tube 300 substantially is not in fluid communication with a body cavity into which it is inserted. The open end 318 is outside of the sleeve seal 302 and enables the camera tether to bypass the sleeve seal 302.

In use, after the obturator shaft 307 and obturator tip 308, cannula tube 304, and sleeve seal 300 have been inserted through tissue 102, the obturator tip 308 and shaft 307 may be removed, as shown in FIG. 10B. The cannula tube 304 still extends through the cannula sleeve 300, and the sleeve seal 302 therefore remains open.

In FIG. 10C, the cannula tube 304 has been partially withdrawn from the tissue 102 and from the cannula sleeve 300. The cannula sleeve 300 remains inserted in the body cavity through the tissue 102. Because the cannula tube 304 has been withdrawn from the distal end of the cannula sleeve 300, the sleeve seal 302 is able to close. The closed sleeve seal 302 inhibits the escape of insufflation gases. As described above, the sleeve seal 302 may be biased in a closed position such that it closes in the absence of the cannula tube 304 or other endoscopic device passing through the cannula tube 304. Because the cannula sleeve 300 is made of a rigid or semi-rigid material, it maintains its shape (in other words, the cannula sleeve 300 does not collapse) when the cannula tube 304 is removed.

Figure 10H:
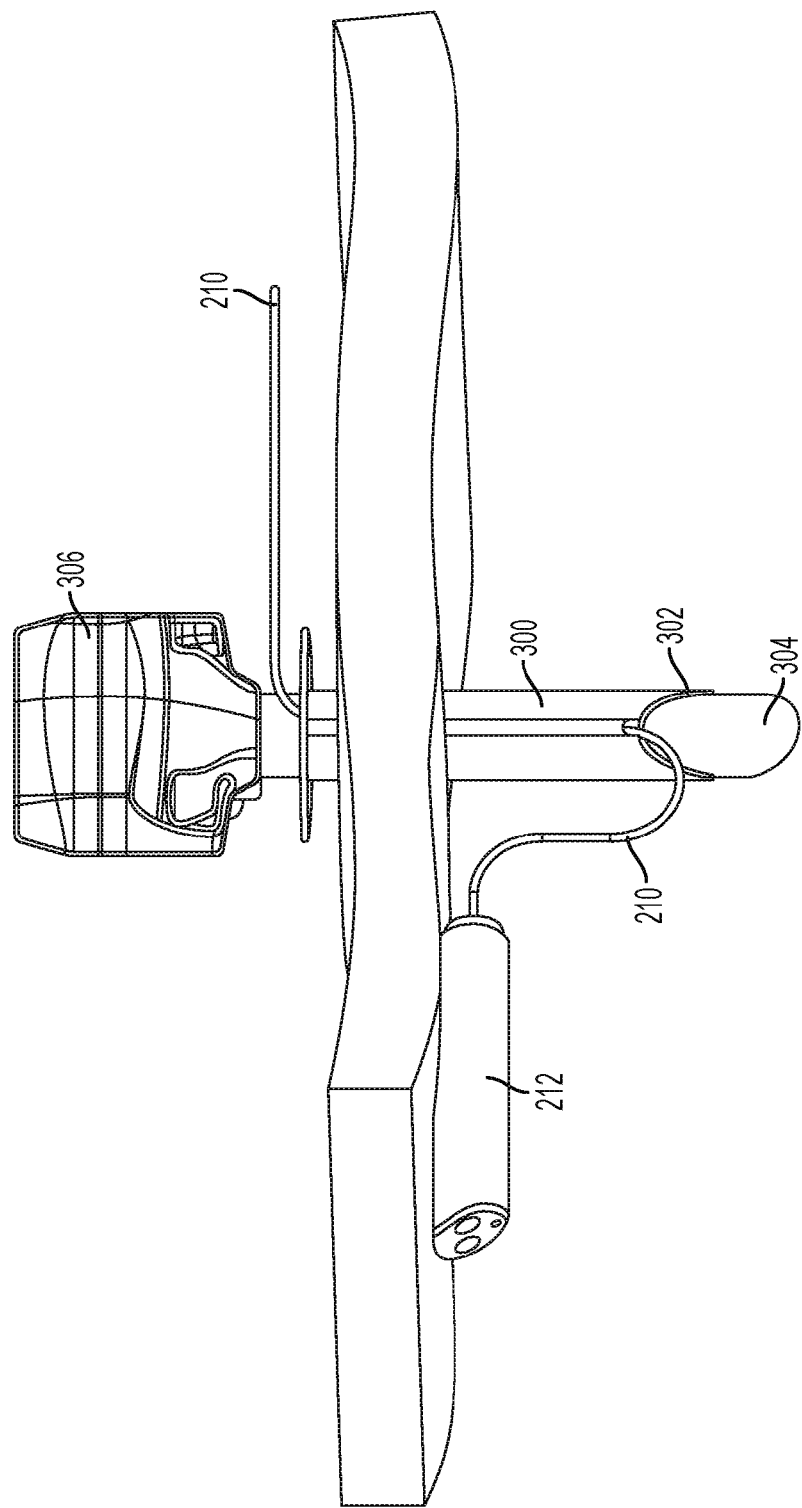
FIG. 10H is a perspective view of the trocar assembly of FIG. 10B with a camera and a tether.

FIG. 10H shows the cannula sleeve 300 with the camera 212 inserted therethrough. In addition, the cannula tube 304 has been reinserted into the cannula sleeve 300. Because the tether 210 is in the tether channel 316 outside of the passage 320 in the cannula sleeve 300, the cannula tube 304 can pass through the passage 320, and the cannula tube 304 does not pull on the tether 210.

Figure 11:
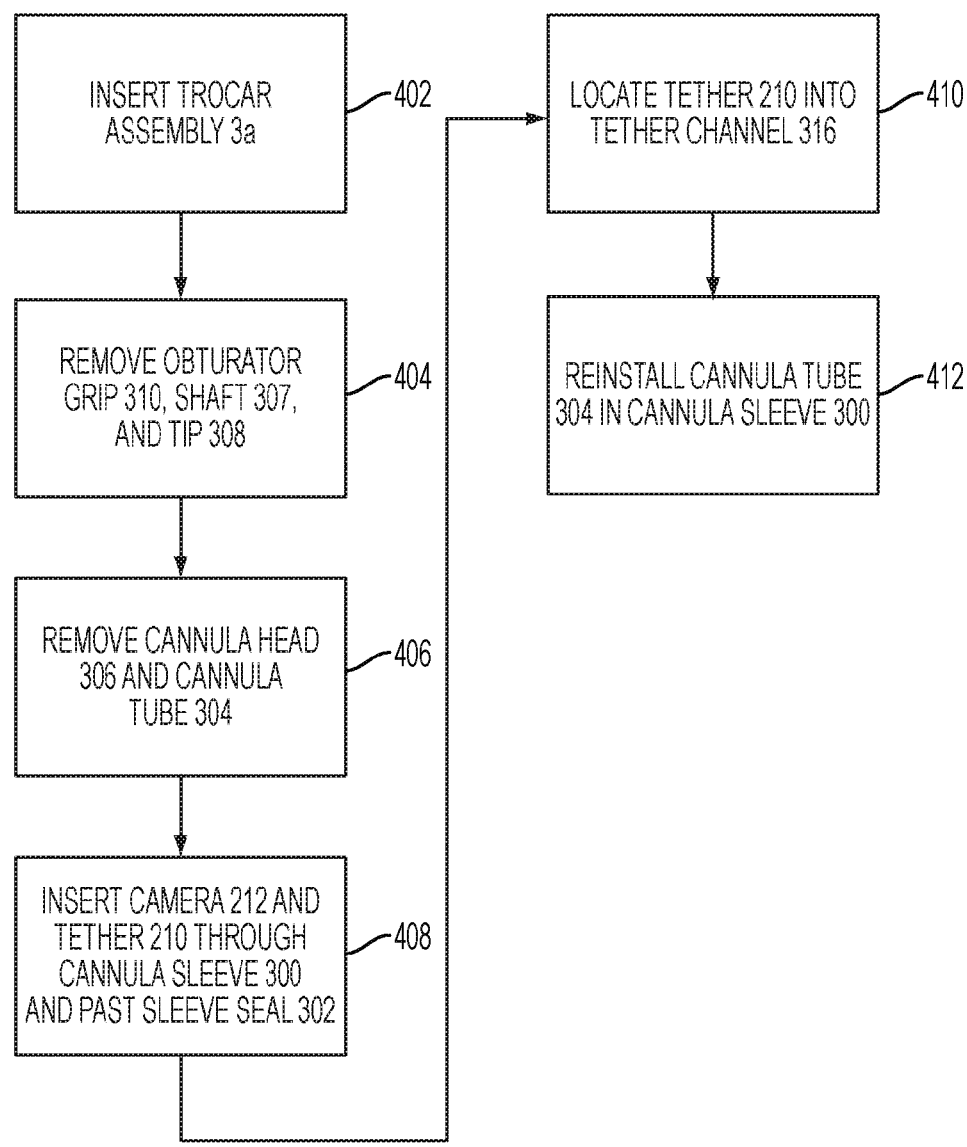
FIG. 11 is a flow chart of method steps for using the trocar assembly of FIG. 10A with a camera and tether.

FIG. 11 shows the steps performed by a surgeon to insert and use the trocar assembly 301 shown in FIGS. 10A-10H. In step 402, the surgeon inserts the trocar assembly 301 through the patient's tissue 102. After the trocar assembly 301 is inserted and properly positioned, in step 404, the obturator grip 310, shaft 307, and tip 308 are removed. Then, in step 406, the cannula head 306 and tube 304 are removed, leaving the cannula sleeve 300. Alternatively, steps 404 and 406 may be combined such that the obturator 310 and cannula 304 are removed from the cannula sleeve 300 simultaneously. In step 408, the surgeon inserts the camera 212 into the passage 320 of the cannula sleeve 300. The surgeon pushes the camera 212 past the sleeve seal 302 so that the camera 212 and a portion of the camera's tether 210 are in the interior body cavity 103. Then, in step 410, the surgeon locates the portion of the tether 210 passing through the cannula sleeve 300 into the tether channel 316. Then, in step 412, the surgeon reinserts the cannula tube 304 or another endoscopic surgical instrument into the cannula sleeve 300.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, nose, anus, and/or vagina) or via a trocar through a relatively small—keyhole—incision incisions (usually 0.5-2.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

All materials used that are in contact with a patient are preferably made of biocompatible materials.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention claimed is:

1. A cannula assembly, comprising:
    a housing, comprising:
        a distal end defining a distal opening, wherein the distal end is configured to couple to a cannula tube aligned with the distal opening; and
        a proximal end defining a proximal opening;
    a rotatable member positioned within the housing, wherein the rotatable member defines a passage in fluid communication with the distal opening, a first opening in fluid communication with the passage, and a second opening in fluid communication with the passage;
    a first plurality of membranes arranged as a stack at the first opening, wherein each of the first plurality of membranes defines an aperture; and
    a second plurality of membranes arranged as a stack at the second opening, wherein each of the second plurality of membranes defines an aperture;
    wherein the rotatable member is configured to rotate within the housing between a first position and a second position, wherein in the first position, the first opening aligns with the distal opening of the housing, and wherein in the second position, the second opening aligns with the distal opening of the housing.

2. The cannula assembly of claim 1, further comprising a hollow cannula tube coupled to the distal end of the housing, wherein the hollow cannula tube is in fluid communication with the distal opening.

3. The cannula assembly of claim 2, wherein the hollow cannula tube defines a longitudinal slot.

4. The cannula assembly of claim 1, further comprising a housing seal positioned intermediate the rotatable member and the housing, wherein the housing seal defines a seal passage in fluid communication with the passage defined by the rotatable member and the distal opening.

5. The cannula assembly of claim 4, wherein the housing seal is configured to supplementally seal the second opening in the first position and the first opening in the second position.

6. The cannula assembly of claim 5, wherein the housing seal is further configured to seal at least a portion of the passage defined by the rotatable member.

7. The cannula assembly of claim 1, wherein the respective apertures at the first opening and the respective apertures at the second opening are each configured for at least one surgical tool to pass therethrough.

8. The cannula assembly of claim 7, wherein the at least one surgical tool comprises at least one of an obturator or a tethered camera.

9. The cannula assembly of claim 7, wherein the first plurality of membranes are arranged to substantially seal the first opening irrespective of the at least one surgical tool passing therethrough, and wherein the second plurality of membranes are arranged to substantially seal the second opening irrespective of the at least one surgical tool passing therethrough.

10. The cannula assembly of claim 9, wherein the respective apertures of the first plurality of membranes do not overlap.

11. The cannula assembly of claim 10, wherein the respective apertures of the second plurality of membranes do not overlap.

12. A cannula assembly, comprising:
    a bracket that defines a distal opening;
    a cannula tube coupled to the bracket, wherein the cannula tube defines a longitudinal axis, and wherein the distal opening defined by the bracket is aligned with the longitudinal axis;
    a first seal component rotatably coupled to the bracket, wherein the first seal component defines a first passage fluidically coupleable with the distal opening defined by the bracket, wherein a first opening is fluidically coupled to the first passage, and wherein a second opening is fluidically coupled to the first passage;

a first plurality of compliant membranes arranged at the first opening, wherein each of the first plurality of compliant membranes defines an aperture;

a second plurality of compliant membranes arranged at the second opening, wherein each of the second plurality of compliant membranes defines an aperture; and a second seal component rotatably interfaced with the first seal component and coupled to the bracket, wherein the second seal component defines a second passage fluidically coupleable with the first passage, and wherein the second passage is fluidically coupled to the distal opening defined by the bracket;

wherein the first seal component is configured to rotate within the bracket between a first position and a second position, wherein in the first position, the first opening is aligned with the longitudinal axis of the cannula tube, and wherein in the second position, the second opening is aligned with the longitudinal axis of the cannula tube.

13. The cannula assembly of claim 12, wherein:
in the first position, a first fluid flow path is defined from a distal end of the cannula tube to the respective apertures at the first opening; and
in the second position, a second fluid flow path is defined from the distal end of the cannula tube to the respective apertures at the second opening.

14. The cannula assembly of claim 13, wherein the first plurality of compliant membranes and the second plurality of compliant membranes are arranged to substantially seal the first fluid flow path and the second fluid flow path respectively.

15. The cannula assembly of claim 13, wherein the first fluid flow path is configured for a tethered camera to be removably inserted therethrough, and wherein the second fluid flow path is configured for a surgical instrument to be removably inserted therethrough.

16. The cannula assembly of claim 15, wherein the first seal component is configured to rotate from the first position to the second position with the tethered camera inserted through the first fluid flow path, and wherein the second seal component is configured to supplementally seal the first opening in the second position.

17. The cannula assembly of claim 16, wherein the second seal component defines a slit for a tether of the tethered camera to pass therethrough.

18. The cannula assembly of claim 16, wherein the cannula tube defines a longitudinal slot parallel to the longitudinal axis, and wherein the longitudinal slot is configured for a tether of the tethered camera to pass therethrough.

19. A cannula system, comprising:
a cannula assembly, comprising:
a housing that defines a distal opening;
a tube coupled to and extending distally from the housing, wherein the tube is aligned with the distal opening;
a rotatable cylinder positioned within the housing, wherein the rotatable cylinder defines a first passage fluidically coupled to the distal opening and a first opening fluidically coupled to the first passage;
a plurality of seal membranes arranged at the first opening, wherein each of the plurality of seal membranes defines an aperture; and
a cylinder seal component interfaced with the rotatable cylinder and coupled to the housing, wherein the cylinder seal component defines a second passage fluidically coupled to the first passage and the distal opening;
wherein, in a first rotated position of the rotatable cylinder, the first opening aligns with the distal opening to define a first fluid path from a distal end of the tube to the first opening; and
a surgical instrument removably positioned within the first fluid path.

20. The cannula system of claim 19, wherein the plurality of seal membranes are arranged to substantially seal the first opening with the surgical instrument positioned therein, and wherein the cylinder seal component is configured to seal at least a portion of the first passage.

\* \* \* \* \*